United States Patent
Armani et al.

(10) Patent No.: US 10,117,860 B2
(45) Date of Patent: Nov. 6, 2018

(54) AMINOESTER DERIVATIVES

(71) Applicant: CHIESI FARMACEUTICI S.P.A., Parma (IT)

(72) Inventors: Elisabetta Armani, Parma (IT); Gabriele Amari, Parma (IT); Carmelida Capaldi, Parma (IT); Wesley Blackaby, Saffron Walden (GB); Ian Linney, Saffron Walden (GB); Hervé Van De Poël, Saffron Walden (GB); Charles Baker-Glenn, Saffron Walden (GB); Naimisha Trivedi, Saffron Walden (GB)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

(21) Appl. No.: 15/673,710

(22) Filed: Aug. 10, 2017

(65) Prior Publication Data
US 2017/0340616 A1    Nov. 30, 2017

Related U.S. Application Data

(63) Continuation of application No. 14/723,964, filed on May 28, 2015, now Pat. No. 9,763,924.

(30) Foreign Application Priority Data

Jun. 5, 2014 (EP) .................................... 14171266

(51) Int. Cl.
| | |
|---|---|
| A61K 31/444 | (2006.01) |
| A61K 31/4545 | (2006.01) |
| A61K 31/4436 | (2006.01) |
| C07D 453/02 | (2006.01) |
| C07D 409/12 | (2006.01) |
| C07D 409/14 | (2006.01) |

(52) U.S. Cl.
CPC ........ *A61K 31/444* (2013.01); *A61K 31/4436* (2013.01); *A61K 31/4545* (2013.01); *C07D 409/12* (2013.01); *C07D 409/14* (2013.01); *C07D 453/02* (2013.01); *H05K 999/99* (2013.01)

(58) Field of Classification Search
CPC .............. A61K 31/444; A61K 31/4436; A61K 31/4545; C07D 409/12; C07D 453/02; C07D 409/14

See application file for complete search history.

(56) References Cited

U.S. PATENT DOCUMENTS

| | | |
|---|---|---|
| 9,090,606 B2 | 7/2015 | Armani et al. |
| 9,133,185 B2 | 9/2015 | Amari |
| 2009/0203657 A1 | 8/2009 | Callahan et al. |
| 2014/0155373 A1 | 6/2014 | Armani et al. |
| 2014/0155427 A1 | 6/2014 | Armani et al. |
| 2014/0155428 A1 | 6/2014 | Armani |
| 2015/0158857 A1 | 6/2015 | Amari et al. |
| 2015/0158858 A1 | 6/2015 | Amari et al. |

FOREIGN PATENT DOCUMENTS

| | | |
|---|---|---|
| WO | 2009/018909 | 2/2009 |
| WO | 2009/018909 A2 | 2/2009 |
| WO | 2010/089107 | 8/2010 |
| WO | 2014/086849 | 6/2014 |

OTHER PUBLICATIONS

Albertson, T. E., "Pharmacotherapy of critical asthma syndrome: current and emerging therapies." Clinical reviews in allergy & immunology 48.1 (2015): 7-30.*
Gordon, J.A., "Lung Cancer and Mesothelioma." (2015) University of Massachusetts, p. 1-9.*
Rumrich, I.K., "Environmental Reduction Potential of Asthma Burden in Finland." (2014) University of Eastern Finland, p. 1-115.*
WEBMD (https://www.webmd.com/lung/copd/tc/chronic-obstructive-pulmonary-disease-copd-prevention (2018) p. 1-11.*
European Search Report in Application No. 14171266.1 dated Aug. 20, 2014.
Laine, Expert Rev. Clin. Pharmacol., vol. 3, No. 1, pp. 43-53 (2010).
Provins et al., Bioorg. Med. Chem. Lett., vol. 16, pp. 1834-1839 (2006).
Provins et al., Bioorg. Med. Chem. Lett., vol. 17, pp. 3077-3080 (2007).
Carey, FA. Organic Chemistry 6th Ed. McGraw hill. 2006, chapter 1, p. 9.

* cited by examiner

*Primary Examiner* — John M Mauro
(74) *Attorney, Agent, or Firm* — Oblon, McClelland, Maier & Neustadt, L.L.P.

(57) ABSTRACT

Compounds of formula (I), defined herein, are both phosphodiesterase 4 (PDE4) enzyme inhibitors and muscarinic M3 receptor antagonists and are useful for the prevention and/or treatment of a disease of the respiratory tract.

17 Claims, No Drawings

AMINOESTER DERIVATIVES

CROSS REFERENCES TO RELATED APPLICATIONS

This application claims priority to European Patent Application No. 14171266.1, filed on Jun. 5, 2014, which is incorporated herein by reference in its entirety.

BACKGROUND OF THE INVENTION

Field of the Invention

The present invention relates to novel compounds which are both phosphodiesterase 4 (PDE4) enzyme inhibitors and muscarinic M3 receptor antagonists. The present invention also relates to methods of preparing such a compound, compositions containing such a compound, and therapeutic uses of such a compound.

Discussion of the Background

Chronic obstructive pulmonary disease (COPD) is a respiratory disorder characterized by progressive, not fully reversible, airflow limitation associated with an abnormal pulmonary inflammatory response to noxious particles or gases.

For this reason, bronchial relaxation and inflammatory response suppression represent a mechanistic approach to the treatment of COPD that might improve symptoms such as dyspnea, wheezing, chest tightness, cough and mucus secretion, improve health status and reduce exacerbations.

Nowadays, the drug therapy options for COPD fall into two general classes: bronchodilators, (β2-adrenoceptor agonists, antimuscarinic agents and methylxanthines) and anti-inflammatory agents (glucocorticosteroids and selective phosphodiesterase-4 (PDE4) inhibitors).

Bronchodilator drugs are the current mainstay of treatment for symptoms' relief.

As anticholinergic bronchodilators, the efficacy of muscarinic M3 antagonists is based on the fact that the major reversible component of airflow narrowing in COPD patients is the increase of acetylcholine (ACh) released to airway smooth muscle, by the bronchial postganglionic vagal efferent in some pathological conditions. Therefore, compounds that antagonize the action of ACh at muscarinic receptors are able to counteract the bronchoconstriction and thus improve lung function in these patients.

Muscarinic antagonists block the effects of ACh at muscarinic receptors.

Currently, there are five known muscarinic receptor subtypes (M1-M5); human airway smooth muscle contains M1, M2 and M3 receptors. M1 receptors facilitate neurotransmission through parasympathetic ganglia and are weakly expressed on submucosal glands in human airways. The M2 receptors are located on the smooth-muscle fibers. Some studies have suggested a small role of M2 mediating the inhibition of airway smooth-muscle relaxation caused by adenylyl cyclase activation by compounds such as beta agonists. In addition, presynaptic M2 receptors are found on postganglionic parasympathetic nerves that project to airway smooth muscle and mucus-producing cells.

These presynaptic M2 autoreceptors provide a negative feedback mechanism, which, when stimulated, inhibit further release of ACh. Postsynaptic M3 receptors are known to mediate both contraction of smooth muscle in the respiratory tract and mucus secretion, making them a major target for symptomatic relief of COPD. Consequently, in the airways, the major effects of muscarinic antagonists are bronchodilation and reduction of mucus secretion via blockage of ACh-induced effects in the parasympathetic nervous system.

Given the distribution of muscarinic receptors, systemically available agents that bind to muscarinic receptors outside of the respiratory tract have the potential to produce unwanted side effects such as tachycardia, dry mouth, urinary retention and constipation. Whereas dry mouth is the most common systemic anticholinergic side effect associated with the use of antimuscarinic antagonists as a result of the systemic blockade of M1 and M3 receptors, the most potentially serious systemic effect is tachycardia, which results from the blockade of cardiac M2 receptors.

Inhaled anticholinergic antimuscarinic drugs approved for the treatment of COPD include ipratropium bromide (Atrovent®), oxitropium bromide (Oxivent®) and tiotropium bromide (Spiriva®). Both ipratropium and oxitropium are short-acting agents.

In contrast, tiotropium bromide is the only long-acting antimuscarinic agent (*LAMA*) currently marketed for COPD, proved to be suitable for once-daily administration as a dry powder. Several others newer LAMAs are newly registered for the treatment of COPD, including aclidinium bromide and glycopyrrolate bromide, or are currently in phase III development, including umeclidinium.

Although bronchodilators are quite effective to improve symptoms, they do not address the underlying chronic inflammation or the changes in airway structure.

Standard treatment with glucocorticosteroids as antiinflammatory agents has demonstrated limited efficacy. However, among the antiinflammatory agents currently being developed, PDE4 inhibitors proved to be effective in attenuating the responses of various inflammatory cells, through their ability to elevate cAMP levels.

PDE4 is the predominant PDE expressed in neutrophils and T cells, suggesting that PDE4 inhibitors would be effective in controlling inflammation in COPD. Inhibition of PDE4 in inflammatory cells influences various specific responses, such as the production and/or release of pro-inflammatory mediators including cytokines and reactive oxygen species, with a well-documented efficacy in animal models mimicking certain aspects of asthma and COPD, as well as inflammatory bowel disease, atopic dermatitis, psoriasis and rheumatoid arthritis.

The selective PDE4 inhibitor, roflumilast (Daxas®) is an approved phosphodiesterase-4 inhibitor for the treatment of COPD associated with chronic bronchitis and a history of exacerbations. Roflumilast inhibits lung inflammation and emphysema in a smoking model of COPD in mice. In COPD patients, oral roflumilast given over 4 weeks significantly reduces the numbers of neutrophils (by 36%) and CXCL8 concentrations in sputum. In clinical trials roflumilast (500 mg once daily) given over 12 months improved lung function in COPD patients to a small extent but had little effect in reducing exacerbations or improving quality of life. More recently roflumilast has been shown to significantly improve FEV 1 (by approximately 50 mL) and reduce exacerbation (by about 15%) in patients with severe disease who have frequent exacerbations and mucus hypersecretion. Roflumilast provides clinical benefit when added to salmeterol or tiotropium and so may be used as an additional treatment in patients with severe disease.

However, the clinical utility of PDE4 inhibitors has so far been compromised by the occurrence of mechanism-associated side effects, including headache, nausea and emesis, which often limited the maximally tolerated dose. This problem could be overcome by inhaled delivery and designing compounds with a potentially more advantageous therapeutic window.

Since bronchial relaxation and inflammatory response suppression represent a mechanistic approach to the treatment of COPD, the combination of muscarinic M3 antagonism with selective PDE4 inhibition may lead to a new class of drugs, combining both bronchodilating and antiinflammatory properties in one molecule, which may open new perspectives in the management of COPD.

SUMMARY OF THE INVENTION

Accordingly, it is one object of the present invention to provide novel compounds which act as both an inhibitor of the phosphodiesterase 4 (PDE4) enzyme and a muscarinic M3 receptor antagonist.

It is another object of the present invention to provide novel methods of preparing such a compound.

It is another object of the present invention to provide novel compositions which contain such a compound.

It is another object of the present invention to provide novel therapeutic uses of such a compound.

These and other objects, which will become apparent during the following detailed description, have been achieved by the inventors' discovery that the compounds of formula (I), described below, act as both an inhibitor of the phosphodiesterase 4 (PDE4) enzyme and a muscarinic M3 receptor antagonist.

Thus, in one embodiment, the present invention provides compounds of formula (I):

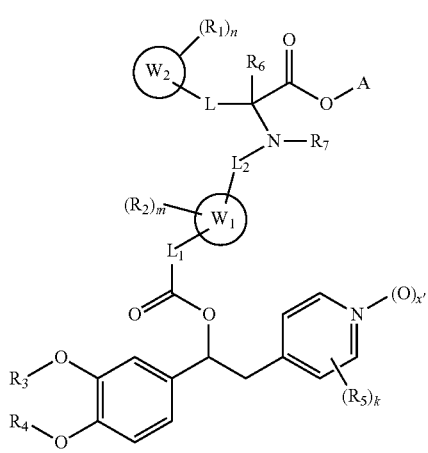

(I)

wherein each $R_1$ is hydrogen or is independently selected in the group consisting of: halogen, $(C_1-C_4)$ alkyl, $(C_1-C_4)$ alkoxy, $(C_1-C_4)$ haloalkyl, hydroxy, $-SO_2NR^IR^{II}$, $-CN$, $-NR^ISO_2R^{III}$, $-NR^IR^{II}$, $-(CO)NR^IR^{II}$ and $-NR^I(CO)R^{III}$, and wherein said $(C_1-C_4)$ alkyl is optionally substituted by one or more groups selected from $(C_3-C_7)$ cycloalkyl, hydroxy and $-NR^IR^{II}$ and wherein said $(C_1-C_4)$ alkoxy is optionally substituted by one or more halogens or groups $(C_3-C_7)$ cycloalkyl wherein:
$R^I$ is hydrogen or $(C_1-C_6)$ alkyl;
$R^{II}$ is hydrogen or $(C_1-C_6)$ alkyl;
$R^{III}$ is hydrogen or $(C_1-C_6)$ alkyl;
n is an integer ranging from 1 to 3;

each $R_2$ is hydrogen or is independently selected in the group consisting of: halogen, $(C_1-C_4)$ alkyl, $(C_1-C_4)$ alkoxy, $(C_1-C_4)$ haloalkyl, hydroxy, $-SO_2NR^IR^{II}$, $-CN$, $-NR^ISO_2R^{III}$, $-NR^IR^{II}$, $-(CO)NR^IR^{II}$ and $-NR^I(CO)R^{III}$ and wherein said $(C_1-C_4)$ alkyl is optionally substituted by one or more groups selected from $(C_3-C_7)$ cycloalkyl, hydroxy and $-NR^IR^{II}$ and wherein said $(C_1-C_4)$ alkoxy is optionally substituted by one or more halogens or groups $(C_3-C_7)$ cycloalkyl wherein:
$R^I$ is hydrogen or $(C_1-C_6)$ alkyl;
$R^{II}$ is hydrogen or $(C_1-C_6)$ alkyl;
$R^{III}$ is hydrogen or $(C_1-C_6)$ alkyl;
m is an integer ranging from 1 to 3;
$R_3$ and $R_4$ are different or the same and are independently selected from the group consisting of: H, $(C_3-C_7)$ cycloalkylcarbonyl, $(C_1-C_6)$ alkyl optionally substituted by one or more substituents selected from $(C_3-C_7)$ cycloalkyl and $(C_5-C_7)$ cycloalkenyl, $(C_1-C_6)$ haloalkyl, $(C_3-C_7)$ cycloalkyl, $(C_5-C_7)$ cycloalkenyl, $(C_2-C_6)$ alkenyl, and $(C_2-C_6)$ alkynyl;

or $R_3$ and $R_4$, together with the interconnecting atoms, form a 2,2-difluoro-1,3-dioxolane ring of formula (r) fused to the phenyl moiety which bears groups $-OR_3$ and $-OR_4$, wherein asterisks indicate carbon atoms shared with such phenyl ring:

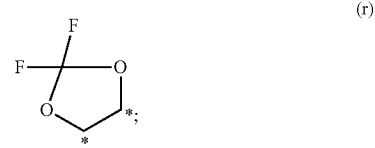

(r)

each $R_5$ is selected from the group consisting of: CN, $NO_2$, $CF_3$ and halogen atoms;
k is 0 or an integer ranging from 1 to 3;
x' is 0 or 1;
$L_1$ is selected from a bond and $-(CH_2)_p-$ wherein p is an integer ranging from 1 to 4;
$W_1$ is selected from a divalent arylene, heteroarylene and saturated monocyclic heterocycloalkylene group;
$L_2$ is a group selected from: a bond, $-(CH_2)_q-$ wherein q is 1 or 2, [1]-(CO)-[X]-$(CH_2)_t$-[2], and [1]-$(SO_2)$-[X]-$(CH_2)_t$-[2], wherein [1] and [2] represent, respectively the point of attachment of group $L_2$ to the ring $W_1$ and to the chain nitrogen atom, and wherein:
[X] is a bond or a substituted or unsubstituted arylene group;
t is an integer ranging from 1 to 4;
$W_2$ is selected from an aryl and heteroaryl group;
L is a bond or a $-(CH_2)-$ group;
$R_6$ is selected in the group consisting of $(C_1-C_4)$ alkyl, $(C_1-C_4)$ alkoxy, $(C_1-C_4)$ haloalkyl, and $-CN$, wherein said $(C_1-C_4)$ alkyl is optionally substituted by one or more groups selected from $(C_3-C_7)$ cycloalkyl, $(C_1-C_4)$ alkoxyl and hydroxyl, or, in alternative, when $R_6$ is $(C_1-C_4)$ alkyl, $W_2$ is a phenyl ring, one of $R_1$ is an alkyl in ortho position with respect to L, both $R_1$ and $R_6$ may be connected to form with $W_2$ a condensed ring radical selected from at least 1H-cyclopropabenzene-1,1-diyl, indane-1,1-diyl (also named as 2,3-dihydro-1H-indene-1,1-diyl), indane-2,2-diyl (also named as 2,3-dihydro-1H-indene-2,2-diyl), 1,2,3,4-tetrahydronaphthalene-1,1-diyl, and 1,2,3,4-tetrahydronaphthalene-2,2-diyl;

$R_7$ is selected from hydrogen and ($C_1$-$C_4$) alkyl optionally substituted by hydroxy or —$NR_{11}R_{12}$ and wherein $R_{11}$ and $R_{12}$ are independently selected from hydrogen, ($C_1$-$C_4$) alkyl, or, together with the nitrogen atom they are linked to may form a saturated heterocycloalkyl group having an additional heteroatom selected from O, S and NH;

A is a nitrogen containing group which may be selected from:
  a group (a) which is —$(CH_2)_s$—$NR_8R_9$ wherein s is an integer ranging from 1 to 4 and $R_8$ and $R_9$ are independently hydrogen or ($C_1$-$C_4$) alkyl; and
  a group (b) which is a saturated monocyclic, bicyclic or tricyclic heterocyclic ring system optionally substituted by one or two groups $R_{10}$ which are at each occurrence independently selected from ($C_1$-$C_4$) alkyl and benzyl;
deuterated derivatives, and pharmaceutically acceptable salts, or solvates thereof.

The present invention further provides compounds of formula (I) wherein x' is 1 which are represented by the formula (IA) wherein a negative charge may be present in the oxygen atom and a corresponding positive charge is on the adjacent nitrogen atom.

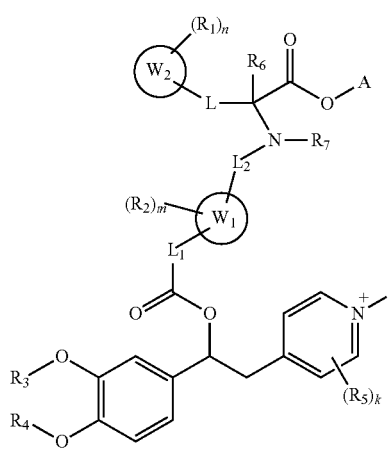

(IA)

wherein $R_1$, $R_2$, $R_3$, $R_4$, $R_5$, $R_6$, $R_7$, L, $L_1$, $W_1$, $L_2$, $W_2$, A, m, n, and k are as described above.

The present invention further provides the corresponding deuterated derivatives of compounds of formula (I) wherein at least one hydrogen atom is substituted by corresponding atoms of deuterium.

The present invention also provides pharmaceutically acceptable salts and/or solvates thereof.

The term "pharmaceutically acceptable salts" refers to derivatives of compounds of formula (I) wherein the parent compound is suitably modified by converting any of the free acid or basic group, if present, into the corresponding addition salt with any base or acid conventionally intended as being pharmaceutically acceptable.

Suitable examples of said salts may thus include mineral or organic acid addition salts of basic residues such as amino groups, as well as mineral or organic acid residues such as carboxylic groups.

Cations of inorganic bases which can be suitably used to prepare salts within the invention comprise ions of alkali or alkaline earth metals such as potassium, sodium, calcium or magnesium.

Those obtained by reacting the main compound, functioning as a base, with an inorganic or organic acid to form a salt comprise, for example, salts of hydrochloric acid, hydrobromic acid, sulfuric acid, phosphoric acid, acetic acid, methane sulfonic acid, camphor sulfonic acid, oxalic acid, maleic acid, fumaric acid, succinic acid and citric acid.

The skilled person will appreciate that many organic compounds can form complexes with solvents in which they are reacted or from which they are precipitated or crystallized. These complexes are known as "solvates". Pharmaceutically acceptable solvates of compound of the invention are within the scope of the invention.

Included within the scope of the present invention are also polymorphs and crystalline forms of compounds of formula (I), or of pharmaceutically acceptable salts, or solvates thereof.

Hereinafter, compounds of formula (I), (IA), (IB), (IC), (ID), (Ia), (Ib), (Ic), (Id) and (I)', enantiomers, diastereoisomers thereof, their pharmaceutically acceptable salts and solvates, and polymorphs or crystalline forms thereof defined in any aspect of the invention (except intermediate compounds described in the chemical processes) are referred to as "compounds of the invention".

The present invention further provides a process for the preparation of compounds of the invention.

The present invention also provides pharmaceutical compositions of compounds of the invention either alone or in combination, in admixture with one or more pharmaceutically acceptable carriers.

In a further aspect, the present invention provides the use of the compounds of the invention as a medicament.

In one aspect, the present invention provides the use of the compounds of the invention for the manufacture of a medicament.

In particular, the present invention provides the use of the compounds of the invention for the prevention and/or treatment of any disease wherein an inhibition of PDE4 activity along with muscarinic M3 receptor antagonism is desirable.

In particular, the compounds of the invention alone or combined with other active ingredients may be administered for the prevention and/or treatment of a disease the respiratory tract characterized by airway obstruction such as asthma and COPD. In one embodiment, the compounds of the invention may be administered for the prevention and/or treatment of COPD.

In a further aspect, the present invention provides the use of compounds of the invention for the preparation of a medicament for the prevention and/or treatment of any disease wherein an inhibition of PDE4 activity along with muscarinic M3 receptor antagonism is desirable.

Moreover, the present invention provides a method for prevention and/or treatment of any disease wherein an inhibition of PDE4 activity along with muscarinic M3 receptor antagonism is desirable, said method comprises administering to a patient in need of such treatment a therapeutically effective amount of a compound of the invention.

A further aspect of the provides invention provides a suitable inhalation device, comprising a pharmaceutical composition of a compound of the invention, which may be respectively selected from a single- or multi-dose dry powder inhaler, a pressurized metered dosed inhaler or a nebulizer and in particular a soft mist nebulizer.

A further aspect of the present invention provides a kit comprising the pharmaceutical compositions of a compound of the invention either alone or in combination with one or more active ingredient and a device which may be a single- or multi-dose dry powder inhaler, a metered dose inhaler or a nebulizer.

DETAILED DESCRIPTION OF THE PREFERRED EMBODIMENTS

The term "halogen atoms" includes fluorine, chlorine, bromine, and iodine, preferably chlorine.

The term "$(C_1-C_x)$ alkyl" where x is an integer greater than 1, refers to straight-chained and branched alkyl groups wherein the number of constituent carbon atoms is in the range 1 to x. Particular alkyl groups are methyl, ethyl, n-propyl, i-propyl, n-butyl, sec-butyl, i-butyl, and t-butyl.

By analogy, the term "$(C_1-C_x)$alkylene" refers to a divalent $(C_1-C_x)$alkyl radical, wherein $(C_1-C_x)$alkyl is as above defined.

The term "$(C_1-C_x)$ alkoxy" or "$(C_1-C_x)$ alkoxyl" where x is an integer greater than 1 refers to straight-chained and branched alkoxy groups wherein the number of constituent carbon atoms is in the range 1 to x. Particular alkoxy groups are methoxy, ethoxy, n-propoxy, i-propoxy, n-butoxy, sec-butoxy, i-butoxy, and t-butoxy.

The expressions "$(C_1-C_x)$haloalkyl" refer to the above defined "$(C_1-C_x)$alkyl" groups wherein one or more hydrogen atoms are replaced by one or more halogen atoms, which can be the same or different from each other. Examples of said $(C_1-C_6)$haloalkyl groups may thus include halogenated, poly-halogenated and fully halogenated alkyl groups wherein all of the hydrogen atoms are replaced by halogen atoms, e.g. trifluoromethyl or difluoro methyl groups.

The term "$(C_3-C_y)$ cycloalkyl", where y is an integer greater than or equal to 3, refers to saturated cyclic hydrocarbon groups containing from 3 to y ring carbon atoms. Examples include cyclopropyl, cyclobutyl, cyclopentyl, cyclohexyl, and cycloheptyl.

The expression "$(C_3-C_y)$cycloalkylcarbonyl" refers to $(C_3-C_y)$cycloalkylCO— groups wherein the group "$(C_3-C_y)$ cycloalkyl" has the meaning above defined.

The term "$(C_2-C_6)$alkenyl" refers to straight or branched, conjugated or non-conjugated, carbon chains with one or more double bonds, in cis or trans configuration, wherein the number of atoms is in the range 2 to 6.

The term "$(C_5-C_z)$ cycloalkenyl", where z is an integer greater than or equal to 5, refers to cyclic hydrocarbon groups containing from 5 to z ring carbon atoms and one or more double bonds.

The term "$(C_2-C_6)$alkynyl" refers to straight or branched carbon chains with one or more triple bonds wherein the number of atoms is in the range 2 to 6.

The term "arylene" refers to divalent mono- or bi-cyclic systems which have 6 to 10 ring carbon atoms, wherein at least one ring is aromatic. Examples of suitable arylene include, for instance phenylenediyl, naphthalenediyl, tetrahydronaphthalenediyl, indanediyl, indenediyl radicals at any suitable position, and the like.

The expression "heteroarylene" refers to divalent mono-cyclic ring systems with 5 to 6 ring atoms, and in which at least one ring atom is a heteroatom (e.g. N, NH, S or O). Non-limiting examples of suitable heteroarylene systems include, for instance, thiophenediyl, furanediyl, pyrrolediyl, pyrazolediyl, imidazolediyl, triazolediyl, tetrazolediyl, isoxazolediyl, oxazolediyl, isothiazolediyl, thiazolediyl, pyridinediyl radicals at any suitable position, and the like.

The expression "heterocycloalkyl" refers to monocyclic cycloalkyl groups with 3 to 6 ring atoms, in which at least one ring carbon atom is replaced by a heteroatom (e.g. N, NH, S or O). Non-limiting examples of heterocycloalkyl are represented by: pyrrolidinyl, thiazolidinyl, imidazolidinyl, oxazolidinyl, piperazinyl, piperidinyl, morpholinyl, thiomorpholinyl, and azetidinyl.

The expression "saturated monocyclic heterocycloalkylene" refers to divalent saturated monocyclic cycloalkyl groups with 3 to 6 ring atoms in which at least one ring carbon atom is replaced by a heteroatom (e.g. N, NH, S or O). Non-limiting examples of "saturated monocyclic heterocycloalkylene" are represented by: pyrrolidinediyl, thiazolidinediyl, imidazolidinediyl, oxazolidinediyl, piperazinediyl, piperidinediyl, morpholinediyl, thiomorpholinediyl, azetidinediyl radicals at any suitable position, and the like.

The term "aryl" refers to mono or bi-cyclic systems which have 6 to 10 ring carbon atoms, wherein at least one ring is aromatic.

The expression "heteroaryl" refers to mono or bi-cyclic systems with 5 to 11 ring atoms, in which at least one ring is aromatic and in which at least one ring atom is a heteroatom (e.g. N, NH, S or O).

Examples of suitable aryl or heteroaryl monocyclic systems with 5 to 6 ring atoms include, for instance, phenyl, thienyl, pyrrolyl, pyrazolyl, imidazolyl, triazolyl, tetrazolyl, isoxazolyl, oxazolyl, isothiazolyl, thiazolyl, pyridyl, furanyl derived radicals and the like.

Examples of suitable aryl or heteroaryl bicyclic systems with more than 6 ring atoms include naphthalenyl, biphenylenyl, tetrahydronaphthalenyl, purinyl, pteridinyl, benzimidazolyl, benzotriazolyl, quinolinyl, isoquinolinyl, indolyl, isoindolyl, indazolyl, lenzothienyl, benzofuranyl, benxoxazolyl, dihydrobenzo dioxinyl, dihydrobenzo dioxepinyl, benzo-oxazinyl radicals and the like.

The expression "heterocyclic ring system" refers to optionally substituted mono-, bi- or tri-cyclic ring systems which may be saturated, partially unsaturated or unsaturated, such as heterocycloalkyl or heteroaryl having 5 to 11 ring atoms in which at least one ring atom is a heteroatom (e.g. N, S or O). Examples of "heterocyclic ring system" are represented by: pyrrolidinyl, imidazolidinyl, piperazinyl, piperidinyl, quinuclidinyl, 8-azabicyclo[3.2.1]octanyl or dehydroxy scopine radical all optionally substituted by oxygen, $(C_1-C_x)$ alkyl or benzyl on a nitrogen atom.

As used in the present description an oxo moiety is represented by (O) as an alternative to the other common representation, e.g. (=O). Thus, in terms of general formula, the carbonyl group is herein preferably represented as —C(O)— as an alternative to the other common representations such as —CO—, —(CO)— or —C(=O)—. In general the bracketed group is a lateral group, not included into the chain, and brackets are used, when deemed useful, to help disambiguating linear chemical formulas; e.g. the sulfonyl group —SO$_2$— might be also represented as —S(O)$_2$— for clarity with respect to the sulfinic group —S(O)O—.

The present invention is directed to a class of compounds which act as both an inhibitor of the phosphodiesterase 4 (PDE4) enzyme and a muscarinic M3 receptor antagonist.

The present invention provides compounds of formula (I), deuterated derivatives and pharmaceutically acceptable salts or solvates thereof:

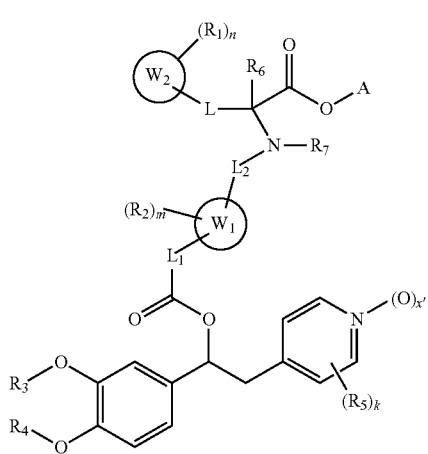

(I)

wherein $R_1$, $R_2$, $R_3$, $R_4$, $R_5$, $R_6$, $R_7$, $L_1$, $W_1$, $L_2$, $W_2$, L, A, n, m, k and x' are as above defined.

Preferred compounds of formula (I) are those wherein the "saturated heterocyclic ring system" A is represented by a group of formula (i), (ii), (iii) or (iv):

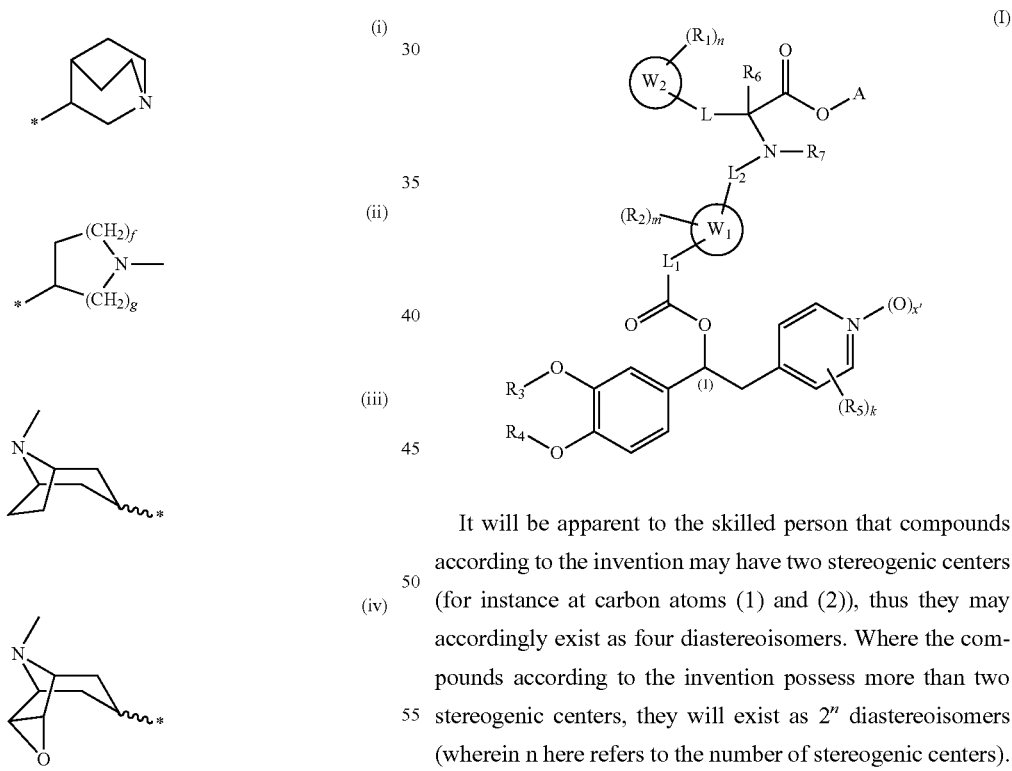

wherein
 f=1, 2 or 3;
 g=1, 2 or 3.
and the asterisk (*) represents the point of attachment to the oxygen atom of formula (I).

More preferably A is represented by a group of formula (i) or (ii):

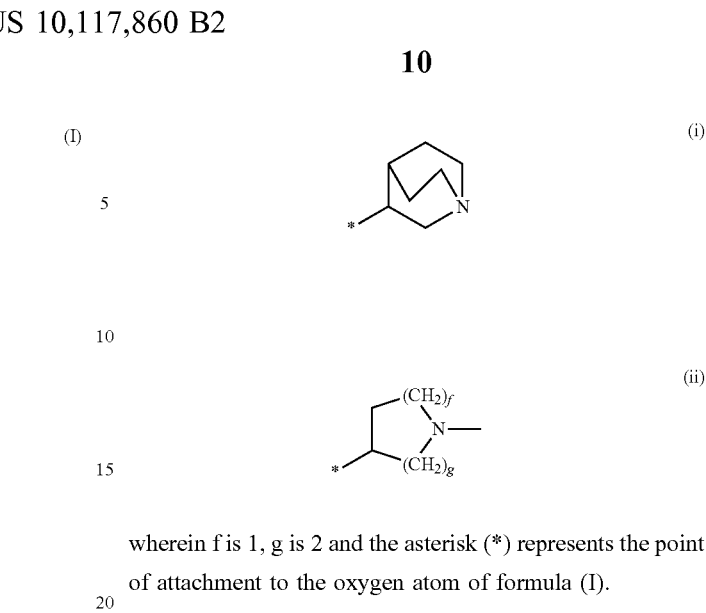

wherein f is 1, g is 2 and the asterisk (*) represents the point of attachment to the oxygen atom of formula (I).

It will be apparent to those skilled in the art that compounds of formula (I) contain at least one stereogenic center, namely represented by the carbon atom (1), and therefore exist as optical stereoisomers.

It will be apparent to the skilled person that compounds according to the invention may have two stereogenic centers (for instance at carbon atoms (1) and (2)), thus they may accordingly exist as four diastereoisomers. Where the compounds according to the invention possess more than two stereogenic centers, they will exist as $2^n$ diastereoisomers (wherein n here refers to the number of stereogenic centers). It is to be understood that all such isomers and mixtures thereof in any proportion are encompassed within the scope of the present invention.

In a preferred embodiment, the present invention is directed to compounds of formula (I)', which are compounds of formula (I) as above defined where the absolute configuration of carbon (1) is that shown below:

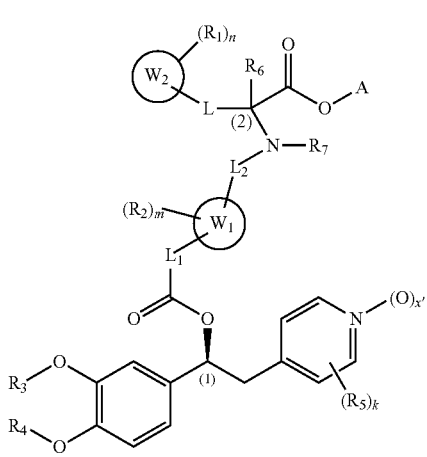

(I)'

The absolute configuration for carbon (1) is assigned on the basis of Cahn-Ingold-Prelog nomenclature based on groups' priorities.

In one preferred embodiment, for compounds of formula (I), the absolute configuration at carbon (1) is (S).

In one embodiment, when A is a group of formula (i) as previously defined, compounds of formula (I), wherein (2) is an asymmetric center, may exist as at least four couples of diastereoisomers (Ia), (Ib), (Ic) and (Id) shown below, which are comprised within the scope of the present invention.

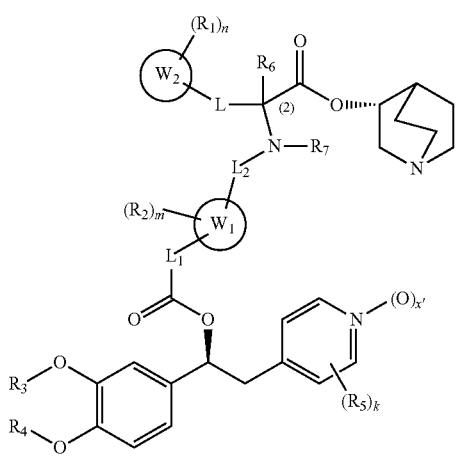

(Ia)

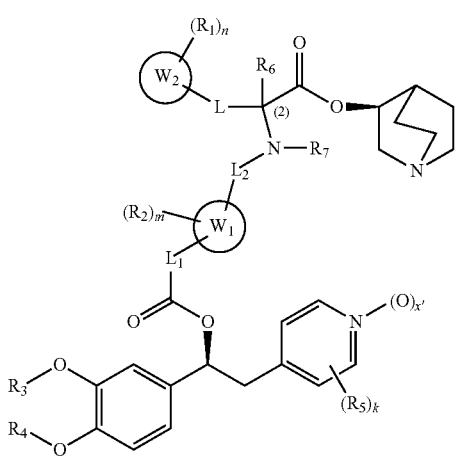

(Ib)

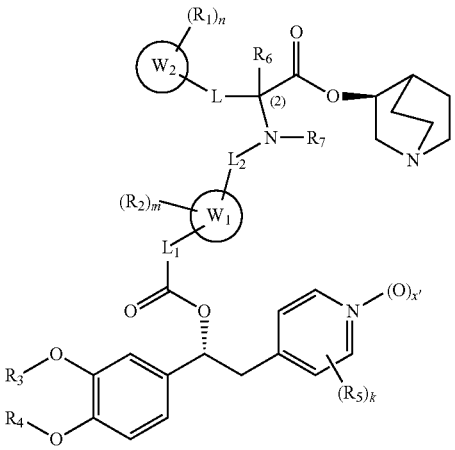

(Ic)

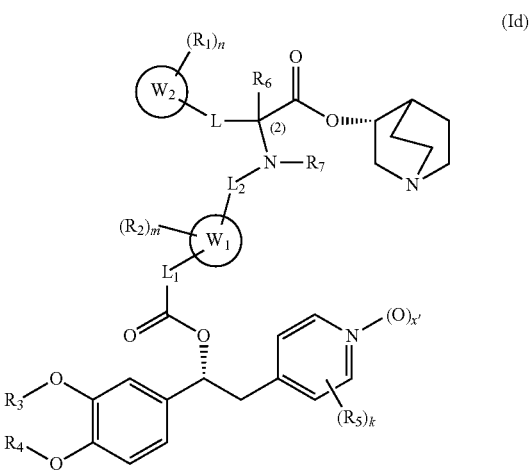

(Id)

It will be apparent to the skilled person that compounds of formula (Ia), (Ib), (Ic), (Id) may be also obtained as single diastereoisomers wherein the configuration at the stereogenic centre at carbon atom (2) is defined as (R) or (S).

In one embodiment, compounds of formula (Ia) are provided as above reported, or single diastereoisomers thereof.

It is to be understood that all preferred groups or embodiments described below and above for compounds of formula (I) may be combined among each other and apply to compounds of formula (IA), (IB), (IC), (ID), (Ia), (Ib), (Ic), (Id) and (I)' as well mutatis mutandis.

In one embodiment, the present invention provides compounds of formula (IA), which are N-oxides on the pyridine ring of compounds of formula (I) wherein x' is 1, deuterated derivatives and pharmaceutically acceptable salts and solvates thereof:

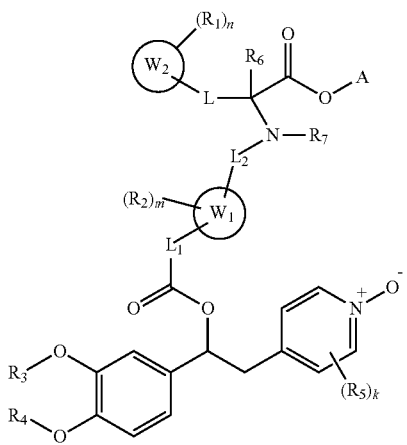

(IA)

wherein R₁, R₂, R₃, R₄, R₅, R₆, R₇, L, L₁, W₁, L₂, W₂, A, m, n, and k are as described above.

In a preferred embodiment, k is 2 and $R_5$ are halogen atoms. In a further preferred embodiment such $R_5$ are two chlorine atoms at positions 3 and 5 of the pyridine ring.

In one preferred embodiment, $R_4$ is selected from a ($C_1$-$C_6$) alkyl and $R_3$ is selected from ($C_3$-$C_7$) cycloalkyl or ($C_1$-$C_6$) alkyl which is optionally substituted by ($C_3$-$C_7$) cycloalkyl.

In another preferred embodiment, $R_3$ and $R_4$ are both methyl.

A preferred compound of formula (I) is that wherein $W_2$ is a phenyl ring, L is a bond, and one of $R_1$, in ortho position with respect to L, and $R_6$ may be connected to form a ring radical, according to the general formula (IB):

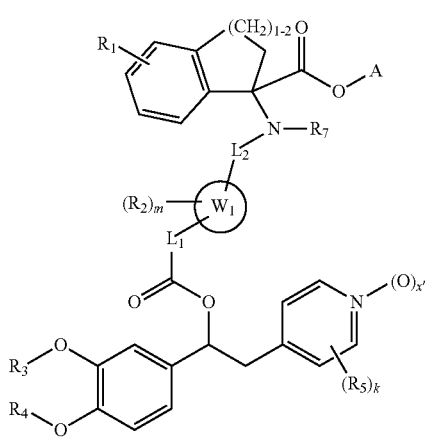

(IB)

wherein R₁, R₂, R₃, R₄, R₅, R₇, A, L₁, W₁, L₂, m, k and x' are as defined above for compounds of formula (I); deuterated derivatives and pharmaceutically acceptable salts and solvates thereof.

In a more preferred compound of formula (IB) $L_1$ is a bond, $W_1$ is a divalent group selected from thiophene-2,5-diyl, thiophene-2,4-diyl, phenylene-1,4-diyl, phenylene-1,3-diyl and phenylene-1,2-diyl, $L_2$ is —(CH₂)—, $R_7$ is H and R₁, R₂, R₃, R₄, R₅, A, m and k are as defined above for compounds of formula (I); deuterated derivatives and pharmaceutically acceptable salts and solvates thereof.

Another preferred compound of formula (I) is that wherein W₂ is a phenyl ring and L is a bond according to the general formula (IC):

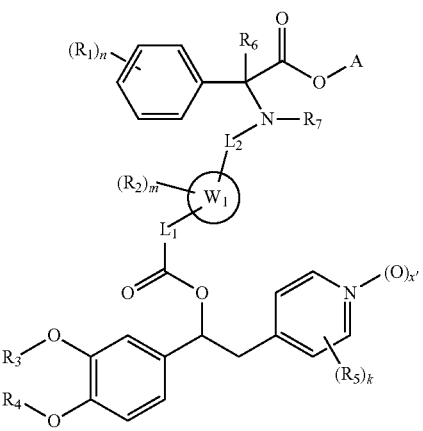

(IC)

wherein $R_6$ is selected from methyl, ethyl, hydroxymethyl, 1-hydroxyethyl, 2-hydroxyethyl, methoxymethyl, trifluoromethyl and difluoromethyl and R₁, R₂, R₃, R₄, R₅, R₇, A, L₁, W₁, L₂, m, n, k and x' are as defined above for compounds of formula (I); and pharmaceutically acceptable salts and solvates thereof.

In a more preferred compound of formula (IC), $L_1$ is a bond, $W_1$ is a divalent group selected from thiophene-2,5-diyl, thiophene-2,4-diyl, phenylene-1,4-diyl, phenylene-1,3-diyl and phenylene-1,2-diyl, $L_2$ is —(CH₂)—, $R_7$ is H or methyl, $R_6$ is selected from methyl, ethyl, hydroxymethyl, 1-hydroxyethyl, 2-hydroxyethyl, methoxymethyl, trifluoromethyl and difluoromethyl and R₁, R₂, R₃, R₄, R₅, A, m, n, k and x' are as defined above for compounds of formula (I); and pharmaceutically acceptable salts and solvates thereof.

Another preferred compound of formula (I) is that wherein $L_1$ is a bond, $W_1$ is selected from a divalent saturated monocyclic heterocycloalkylene group, represented by the general formula (ID):

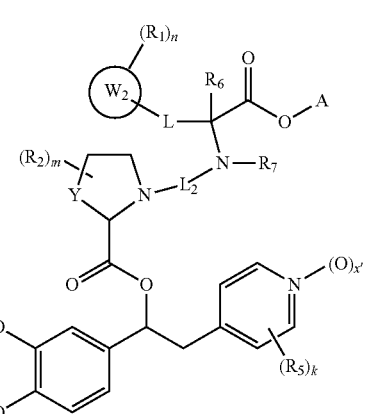

(ID)

wherein
Y is S or CH₂;
$L_2$ is a group selected from —(CH₂)$_q$— wherein q is 1 or 2, [1]-(CO)—[X]—(CH₂)$_r$-[2] and [1]-(SO₂)—[X]—

(CH₂)_t—[2], wherein [1] and [2] represent, respectively the point of attachment of group L₂ to the saturated monocyclic heterocycloalkylene ring (W₁) and to the chain nitrogen atom, and wherein

[X] is a bond or a substituted or unsubstituted arylene group selected from phenylene-1,4-, -1,3- and -1,2-diyl;

t is an integer ranging from 1 to 4;

and wherein $R_1$, $R_2$, $R_3$, $R_4$, $R_5$, $R_6$, $R_7$, A, $W_2$, m, n, k and x' are as defined above for compounds of formula (I), and pharmaceutically acceptable salts and solvates thereof.

According to a preferred embodiment, the present invention provides the compounds reported below:

[(1S)-2-(3,5-dichloro-1-oxido-pyridin-1-ium-4-yl)-1-(3,4-dimethoxyphenyl)ethyl]5-[[[1-methyl-2-oxo-1-phenyl-2-[(3R)-quinuclidin-3-yl]oxy-ethyl]amino]methyl]-thiophene-2-carboxylate formate salt;

[(1S)-2-(3,5-dichloro-1-oxido-pyridin-1-ium-4-yl)-1-(3,4-dimethoxyphenyl)ethyl]4-[[[1-methyl-2-oxo-1-phenyl-2-[(3R)-quinuclidin-3-yl]oxy-ethyl]amino]methyl]-benzoate;

[(3R)-quinuclidin-3-yl]1-[[4-[(1S)-2-(3,5-dichloro-1-oxido-pyridin-1-ium-4-yl)-1-(3,4-dimethoxyphenyl)ethoxy]carbonylphenyl] methylamino]indane-1-carboxylate;

[(1S)-2-(3,5-dichloro-1-oxido-pyridin-1-ium-4-yl)-1-(3,4-dimethoxyphenyl)ethyl]5-[[[1-[(3R)-quinuclidin-3-yl]oxycarbonylindan-1-yl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-methyl-2-[(1-methyl-4-piperidyl)oxy]-2-oxo-1-phenyl-ethyl]amino]methyl]-thiophene-2-carboxylate;

[(1S)-2-(3,5-dichloro-1-oxido-pyridin-1-ium-4-yl)-1-(3,4-dimethoxyphenyl)ethyl]5-[[[1-phenyl-1-[(3R)-quinuclidin-3-yl]oxycarbonyl-propyl]amino]methyl]thiophene-2-carboxylate;

Single diastereoisomer of [(1S)-2-(3,5-dichloro-1-oxido-pyridin-1-ium-4-yl)-1-(3,4-dimethoxyphenyl)ethyl] 5-[[[1-methyl-2-oxo-1-phenyl-2-[(3R)-quinuclidin-3-yl]oxy-ethyl]amino]methyl]thiophene-2-carboxylate;

Single diastereoisomer of [(1S)-2-(3,5-dichloro-1-oxido-pyridin-1-ium-4-yl)-1-(3,4-dimethoxyphenyl)ethyl] 5-[[[1-methyl-2-oxo-1-phenyl-2-[(3R)-quinuclidin-3-yl]oxy-ethyl]amino]methyl]thiophene-2-carboxylate;

Single diastereoisomer of [(1S)-2-(3,5-dichloro-1-oxido-pyridin-1-ium-4-yl)-1-(3,4-dimethoxyphenyl)ethyl] 4-[[[1-methyl-2-oxo-1-phenyl-2-[(3R)-quinuclidin-3-yl]oxy-ethyl]amino]methyl]benzoate;

Single diastereoisomer of [(3R)-quinuclidin-3-yl] 1-[[4-[(1S)-2-(3,5-dichloro-1-oxido-pyridin-1-ium-4-yl)-1-(3,4-dimethoxyphenyl)ethoxy]carbonylphenyl]methylamino]indane-1-carboxylate;

Single diastereoisomer of [(3R)-quinuclidin-3-yl] 1-[[4-[(1S)-2-(3,5-dichloro-1-oxido-pyridin-1-ium-4-yl)-1-(3,4-dimethoxyphenyl)ethoxy] carbonylphenyl]methylamino]indane-1-carboxylate;

Single diastereoisomer of [(1S)-2-(3,5-dichloro-1-oxido-pyridin-1-ium-4-yl)-1-(3,4-dimethoxyphenyl)ethyl] 5-[[[1-[(3R)-quinuclidin-3-yl]oxycarbonylindan-1-yl]amino]methyl]thiophene-2-carboxylate;

Single diastereoisomer of [(1S)-2-(3,5-dichloro-1-oxido-pyridin-1-ium-4-yl)-1-(3,4-dimethoxyphenyl)ethyl] 5-[[[1-[(3R)-quinuclidin-3-yl]oxycarbonylindan-1-yl]amino]methyl]thiophene-2-carboxylate;

Single diastereoisomer of [(1S)-2-(3,5-dichloro-1-oxido-pyridin-1-ium-4-yl)-1-(3,4-dimethoxyphenyl)ethyl] 5-[[[1-methyl-2-[(1-methyl-4-piperidyl)oxy]-2-oxo-1-phenyl-ethyl]amino]methyl]thiophene-2-carboxylate;

Single diastereoisomer of [(1S)-2-(3,5-dichloro-1-oxido-pyridin-1-ium-4-yl)-1-(3,4-dimethoxyphenyl)ethyl] 5-[[[1-methyl-2-[(1-methyl-4-piperidyl)oxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-methyl-2-[(3R)-1-oxido-quinuclidin-1-ium-3-yl]oxy-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-(2-dimethylaminoethyloxycarbonyl)indan-1-yl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-[(1-methyl-4-piperidyl)oxycarbonyl]indan-1-yl]amino]methyl]thiophene-2-carboxylate;

[(1S)-2-(3,5-dichloro-1-oxido-pyridin-1-ium-4-yl)-1-(3,4-dimethoxyphenyl)ethyl]-5-[[[1-(hydroxymethyl)-2-[(1-methyl-4-piperidyl)oxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-(hydroxymethyl)-2-oxo-1-phenyl-2-[(3R)-quinuclidin-3-yl]oxy-ethyl]-methyl-amino]methyl]thiophene-2-carboxylate;

[(1S)-2-(3,5-dichloro-1-oxido-pyridin-1-ium-4-yl)-1-(3,4-dimethoxyphenyl)ethyl]-5-[[[1-(hydroxymethyl)-2-oxo-1-phenyl-2-[(3R)-quinuclidin-3-yl]oxy-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-(methoxymethyl)-2-oxo-1-phenyl-2-[(3R)-quinuclidin-3-yl]oxy-ethyl]amino]methyl]thiophene-2-carboxylate;

Single diastereoisomer of [(1S)-2-(3,5-dichloro-1-oxido-pyridin-1-ium-4-yl)-1-(3,4-dimethoxyphenyl)ethyl] 5-[[[1-(2-dimethylaminoethyloxycarbonyl)indan-1-yl]amino]methyl]thiophene-2-carboxylate;

Single diastereoisomer of [(1S)-2-(3,5-dichloro-1-oxido-pyridin-1-ium-4-yl)-1-(3,4-dimethoxyphenyl)ethyl] 5-[[[1-(2-dimethylaminoethyloxycarbonyl)indan-1-yl]amino]methyl]thiophene-2-carboxylate;

Single diastereoisomer of [(1S)-2-(3,5-dichloro-1-oxido-pyridin-1-ium-4-yl)-1-(3,4-dimethoxyphenyl)ethyl] 5-[[[1-[(1-methyl-4-piperidyl)oxycarbonyl]indan-1-yl]amino]methyl]thiophene-2-carboxylate;

Single diastereoisomer of [(1S)-2-(3,5-dichloro-1-oxido-pyridin-1-ium-4-yl)-1-(3,4-dimethoxyphenyl)ethyl] 5-[[[1-[(1-methyl-4-piperidyl)oxycarbonyl]indan-1-yl]amino]methyl]thiophene-2-carboxylate;

Single diastereoisomer of [(1S)-2-(3,5-dichloro-1-oxido-pyridin-1-ium-4-yl)-1-(3,4-dimethoxyphenyl)ethyl] 5-[[[1-phenyl-1-[(3R)-quinuclidin-3-yl]oxycarbonyl-propyl]amino]methyl]thiophene-2-carboxylate;

Single diastereoisomer of [(1S)-2-(3,5-dichloro-1-oxido-pyridin-1-ium-4-yl)-1-(3,4-dimethoxyphenyl)ethyl] 5-[[[1-phenyl-1-[(3R)-quinuclidin-3-yl]oxycarbonyl-propyl]amino]methyl]thiophene-2-carboxylate;

Single diastereoisomer of [(1S)-2-(3,5-dichloro-1-oxido-pyridin-1-ium-4-yl)-1-(3,4-dimethoxyphenyl)ethyl] 5-[[[1-(hydroxymethyl)-2-[(1-methyl-4-piperidyl)oxy]-2-oxo-1-phenyl-ethyl]amino]methyl]thiophene-2-carboxylate;

Single diastereoisomer of [(1S)-2-(3,5-dichloro-1-oxido-pyridin-1-ium-4-yl)-1-(3,4-dimethoxyphenyl)ethyl] 5-[[[1-(hydroxymethyl)-2-[(1-methyl-4-piperidyl)oxy]-2-oxo-1-phenyl-ethyl]amino]methyl]thiophene-2-carboxylate;

Single diastereoisomer of [(1S)-2-(3,5-dichloro-1-oxido-pyridin-1-ium-4-yl)-1-(3,4-dimethoxyphenyl)ethyl] 5-[[[1-(hydroxymethyl)-2-oxo-1-phenyl-2-[(3R)-quinuclidin-3-yl]oxy-ethyl]amino]methyl]thiophene-2-carboxylate;

Single diastereoisomer of [(1S)-2-(3,5-dichloro-1-oxido-pyridin-1-ium-4-yl)-1-(3,4-dimethoxyphenyl)ethyl] 5-[[[1-(hydroxymethyl)-2-oxo-1-phenyl-2-[(3R)-quinuclidin-3-yl]oxy-ethyl]amino]methyl]thiophene-2-carboxylate;

Single diastereoisomer of [(1S)-2-(3,5-dichloro-1-oxido-pyridin-1-ium-4-yl)-1-(3,4-dimethoxyphenyl)ethyl] 5-[[[1-(hydroxymethyl)-2-oxo-1-phenyl-2-[(3R)-quinuclidin-3-yl]oxy-ethyl]-methyl-amino]methyl]thiophene-2-carboxylate;

Single diastereoisomer of [(1S)-2-(3,5-dichloro-1-oxido-pyridin-1-ium-4-yl)-1-(3,4-dimethoxyphenyl)ethyl] 5-[[[1-(hydroxymethyl)-2-oxo-1-phenyl-2-[(3R)-quinuclidin-3-yl]oxy-ethyl]-methyl-amino]methyl]thiophene-2-carboxylate;

Single diastereoisomer of [(1S)-2-(3,5-dichloro-1-oxido-pyridin-1-ium-4-yl)-1-(3,4-dimethoxyphenyl)ethyl] 5-[[[1-(methoxymethyl)-2-oxo-1-phenyl-2-[(3R)-quinuclidin-3-yl]oxy-ethyl]amino]methyl]thiophene-2-carboxylate;

and a pharmaceutically acceptable salt or solvate thereof.

The expression "single diastereoisomer" was reported near the chemical name of each compound of formula (I) isolated as single diastereoisomer whose absolute configuration at the stereogenic carbon atom (2) at which R6 is linked was not determined.

The present invention also provides processes for the preparation of compounds of the invention.

Compounds of formula (I) can be obtained according to general synthetic route of Scheme A and Scheme B below reported or following slightly modified procedures that the skilled person can easily apply.

In the following Scheme A and Scheme B only compounds of formula (I) in which x' is 1, corresponding to compounds of formula (IA), are described, starting from the pyridine N-oxides (III) described in the co-pending International Patent Application No. PCT/EP2013/075520 (published as WO 2014/086849), which is incorporated herein by reference in its entirety. Any corresponding compound of formula (I) in which x' is 0 may be similarly obtained starting from the non-oxidized pyridines, analogues of compounds (V) described in the co-pending International Patent Application No. PCT/EP2013/075520 (published as WO 2014/086849), which is incorporated herein by reference in its entirety.

Processes of preparation described below and reported in the following Scheme A should not be viewed as limiting the scope of the synthetic methods available for the preparation of the compounds of the invention.

In the following Scheme A and Scheme B, for compounds of formula (IA) and for compounds of formula (II) to (XXI), unless otherwise indicated, $R_1$, $R_2$, $R_3$, $R_4$, $R_5$, $R_6$, $R_7$, $L_1$, $W_1$, $L_2$, $W_2$, L, A, n, m, k and x' are as above defined, PG is a protective group and Y is a group selected from a bond, —$CH_2$—, [1]-(CO)—[X]—$(CH_2)_{t'}$-[2], and [1]-($SO_2$)—[X]—$(CH_2)_{t'}$-[2], wherein [1] and [2] represent, respectively the point of attachment of group Y to the ring $W_1$ and to a formyl group, and wherein [X] is a bond or a substituted or unsubstituted arylene group and t' is 0 or an integer ranging from 1 to 3.

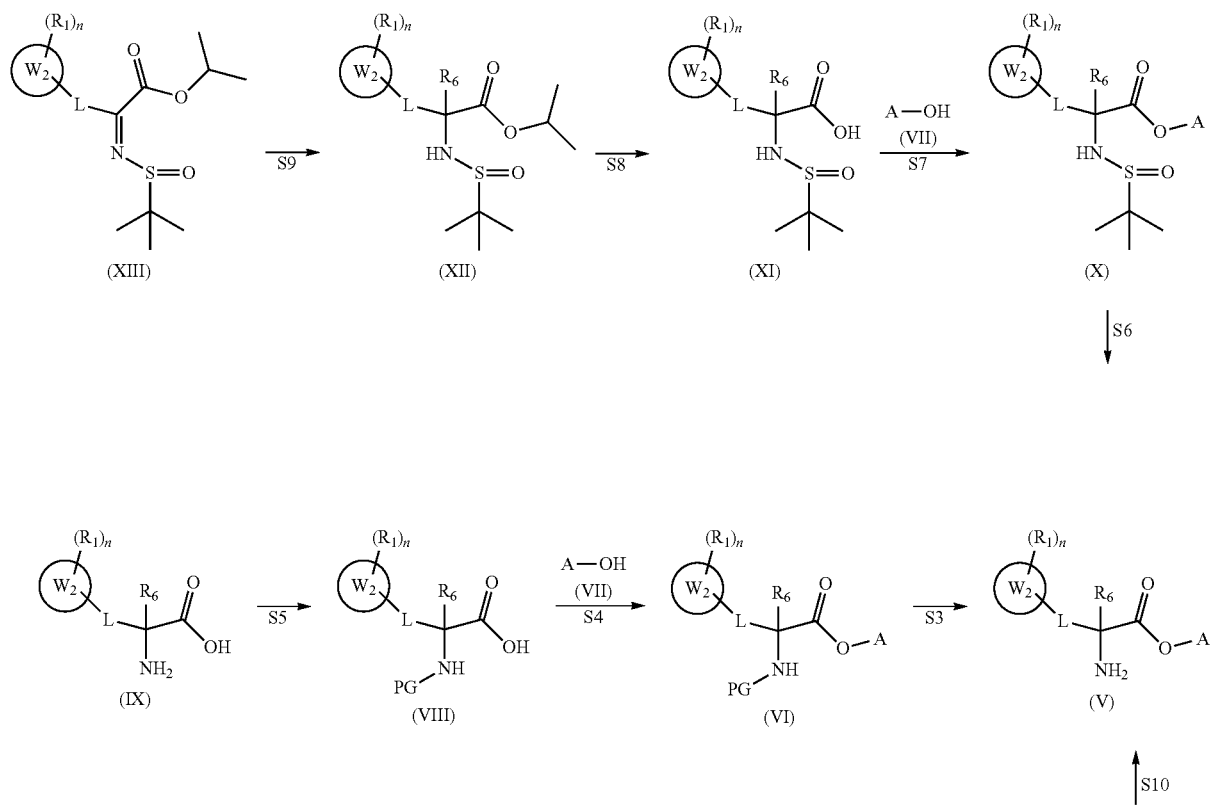

Scheme A

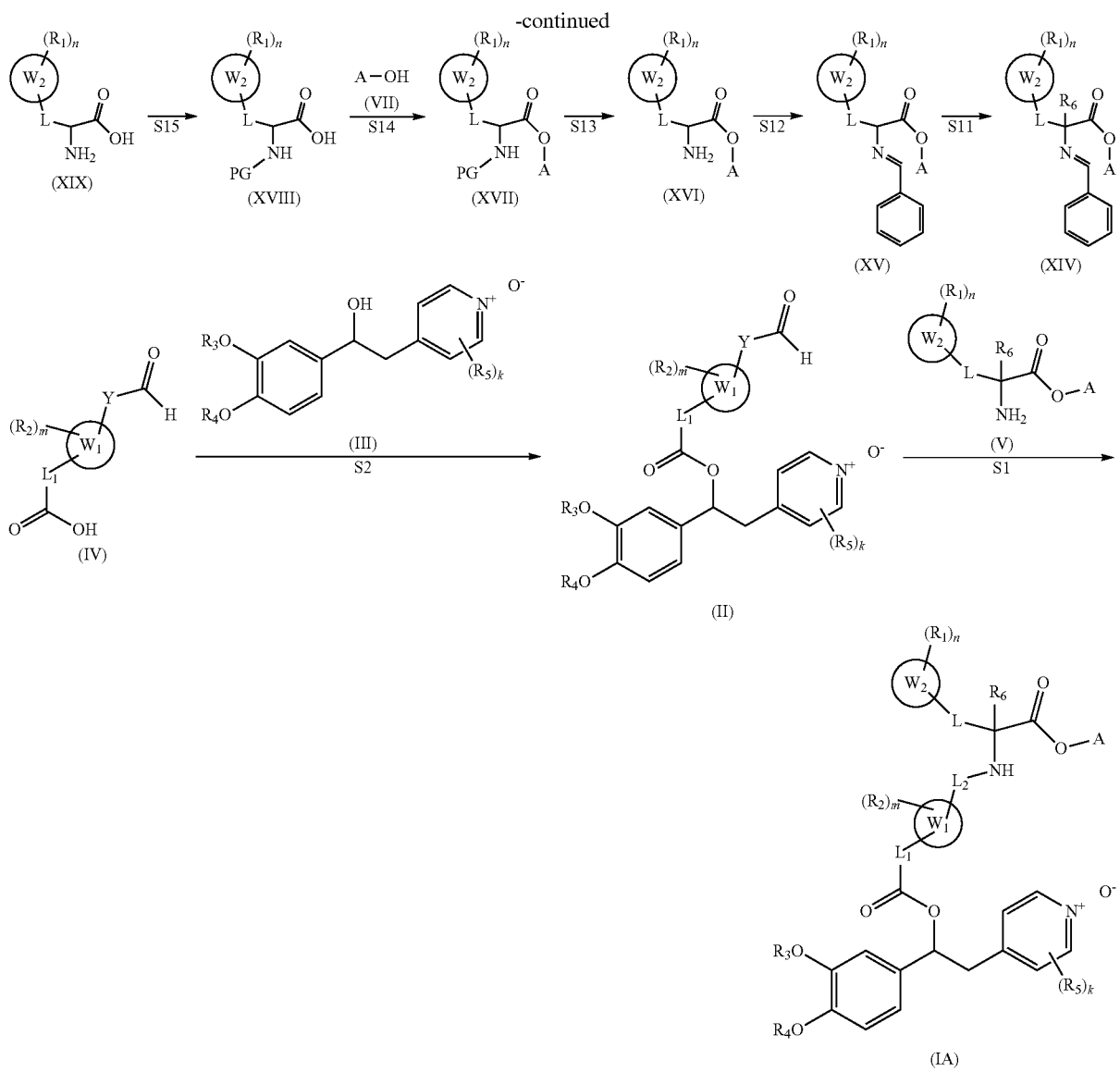
Compounds of formula (IA) may be prepared according to Scheme 1/(S1) below by reaction of a compound of formula (II) with a compound of formula (V) as below reported.
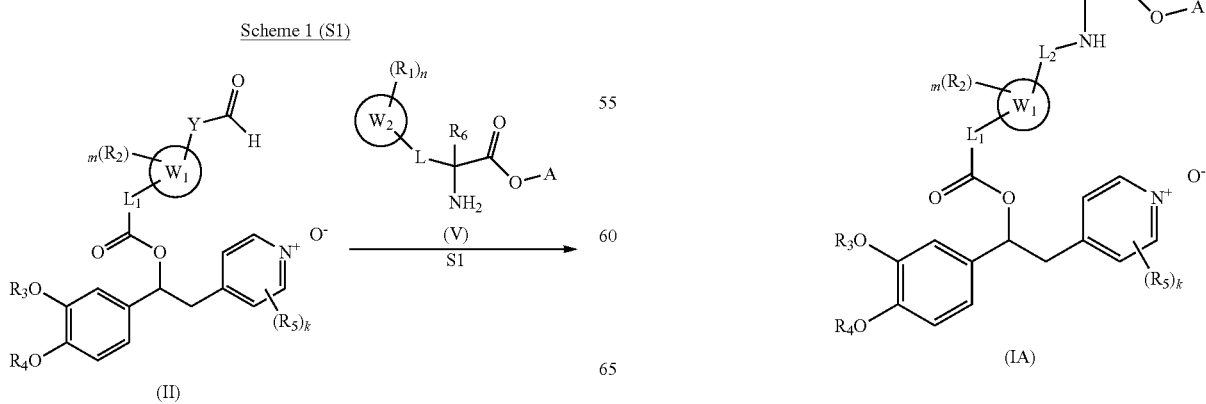

Typical reaction conditions comprise reacting a compound of formula (II) with a compound of formula (V) in a suitable solvent, such as acetonitrile, DCM or ethanol in the presence of an acid, such as acetic acid, and an optional base, such as triethylamine, and a reducing agent, such as NaB(OAc)₃H or NaBH₃CN, at an appropriate temperature, such as room (or ambient) temperature or 0° C. or 40° C.

Compounds of formula (II) may be prepared according to Scheme 2/(S2) below by reaction of a compound of formula (IV) with a compound of formula (III) as below reported.

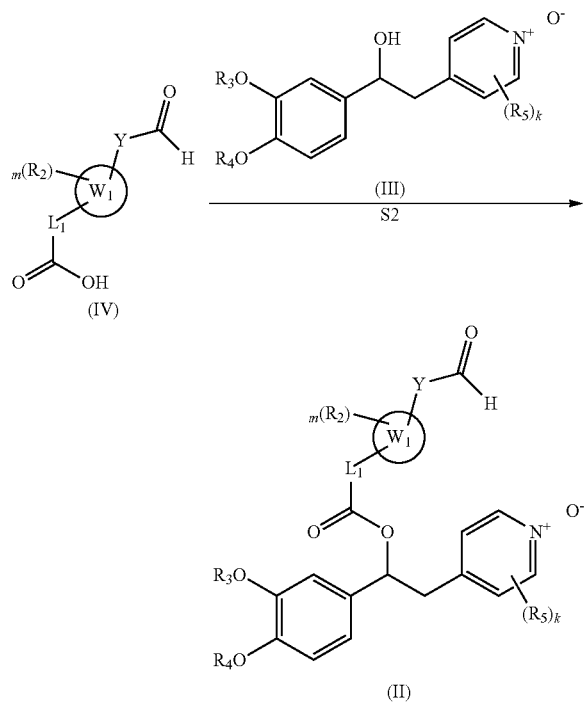

Typical reaction conditions comprise reacting a compound of formula (IV) with a compound of formula (III) in a suitable solvent, such as DCM, in the presence of a suitable coupling agent, such as EDC/DMAP or HATU, at an appropriate temperature, such as room (or ambient) temperature.

Compounds of formula (III) may be prepared as described in the co-pending international application n. PCT/EP2013/075520 (published as WO 2014/086849), which is incorporated herein by reference in its entirety.

Compounds of formula (V) may be prepared according to Scheme 3/(S3) below by deprotection of a compound of formula (VI).

Scheme 3 (S3)

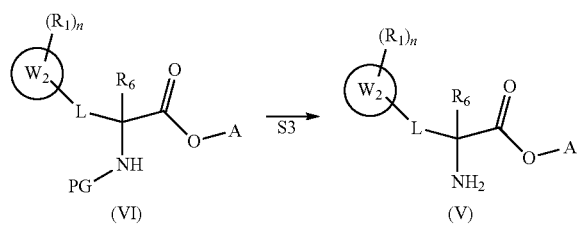

Typical reaction conditions comprise reacting a compound of formula (VI) with a source of hydrogen, such as ammonium formate or gaseous hydrogen over a suitable catalyst, such as 10% Pd/C, in a suitable solvent, such as EtOAc, at an appropriate temperature, such as room (or ambient) temperature.

Compounds of formula (V) may also be prepared by reacting a compound of formula (VI) in a suitable solvent, such as 1,4-dioxane, in the presence of a suitable acid, such as hydrochloric acid, at an appropriate temperature, such as room (or ambient) temperature.

Compounds of formula (VI) may be prepared according to Scheme 4/(S4) below by reaction of a compound of formula (VIII) with a compound of formula (VII) as below reported.

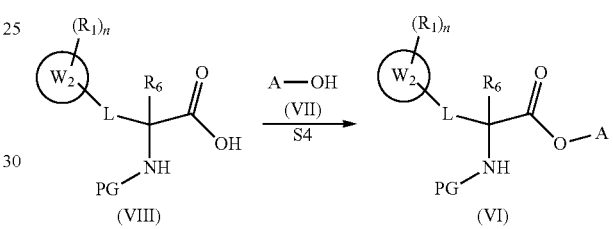

Typical reaction conditions comprise reacting a compound of formula (VIII) with a compound of formula (VII) in a suitable solvent, such as THF in the presence of a suitable coupling agent, such as DCC/HOBt or EDC/DMAP or HATU, at an appropriate temperature, such as room (or ambient) temperature or 40° C.

Compounds of formula (VIII) may be prepared according to Scheme 5/(S5) below by reaction of a compound of formula (IX) as below reported.

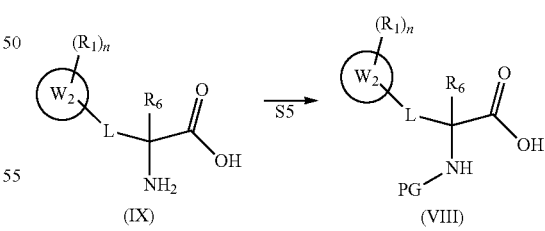

Typical reaction conditions comprise reacting a compound of formula (IX) with benzyl chloroformate or di-tert-butyl dicarbonate, in a suitable solvent, such as THF/water or 1,4-dioxane/water, in the presence of a suitable base such as sodium hydroxide, at an appropriate temperature, such as 0° C. or room (or ambient) temperature.

Compounds of formula (V) may be prepared according to Scheme 6/(S6) below by reaction of a compound of formula (X) as below reported.

Scheme 6 (S6)

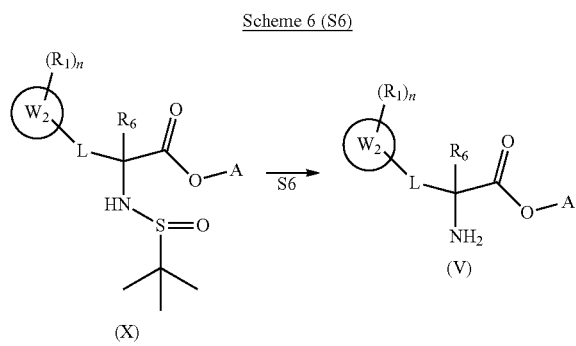

Typical reaction conditions comprise reacting a compound of formula (X) in a suitable solvent, such as 1,4-dioxane, in the presence of a suitable acid, such as hydrochloric acid, at an appropriate temperature, such as room (or ambient) temperature.

Compounds of formula (X) may be prepared according to Scheme 7/(S7) below by reaction of a compound of formula (XI) with a compound of formula (VII) as below reported.

Scheme 7 (S7)

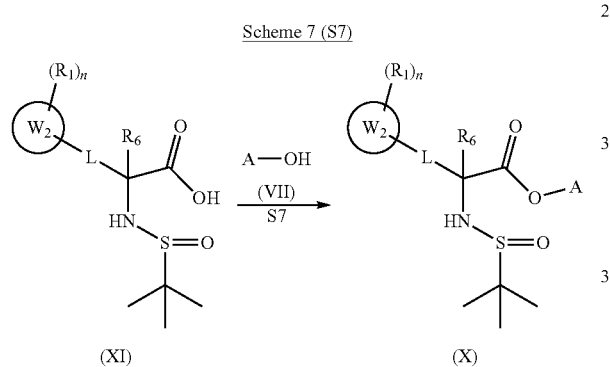

Typical reaction conditions comprise reacting a compound of formula (XI) with a compound of formula (VII) in a suitable solvent, such as THF in the presence of a suitable coupling agent, such as DCC/HOBt or EDC/DMAP or HATU, at an appropriate temperature, such as room (or ambient) temperature or 40° C.

Compounds of formula (XI) may be prepared according to Scheme 8/(S8) below by reaction of a compound of formula (XII) as below reported.

Scheme 8 (S8)

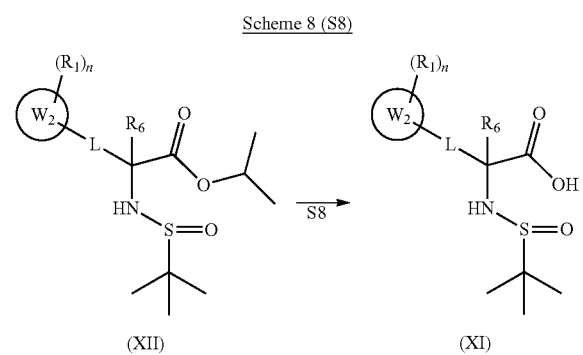

Typical reaction conditions comprise reacting compound of formula (XII) with a suitable base, such as NaOH in a suitable solvent, such as MeOH at an appropriate temperature, such as room (or ambient) temperature or 50° C.

Compounds of formula (XII) may be prepared according to Scheme 9/(S9) below by reaction of a compound of formula (XIII) as below reported.

Scheme 9 (S9)

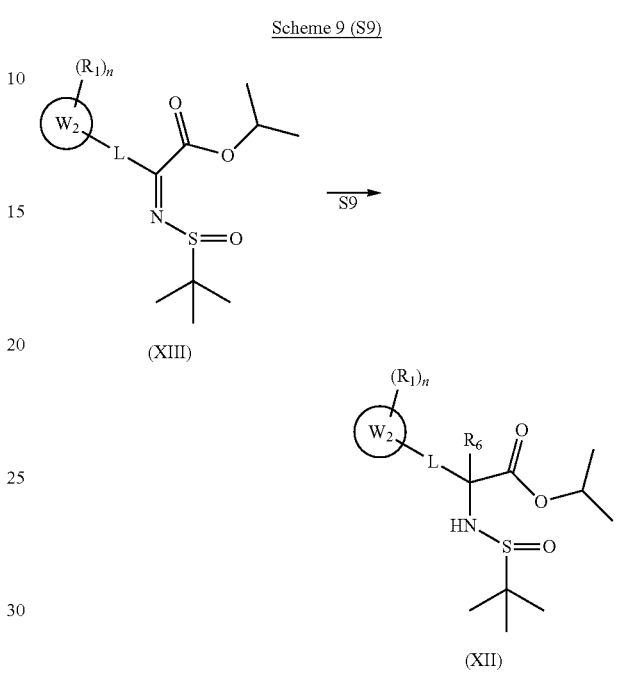

Typical reaction conditions comprise reacting compound of formula (XIII) with a suitable Grignard reagent, such as methyl magnesium bromide or ethyl magnesium bromide, in a suitable solvent, such as THF or diethyl ether at a suitable temperature such at −78° C., 0° C. or room (or ambient) temperature.

Compounds of formula (V) may also be prepared according to Scheme 10/(S10) below by reaction of a compound of formula (XIV) as below reported.

Scheme 10 (S10)

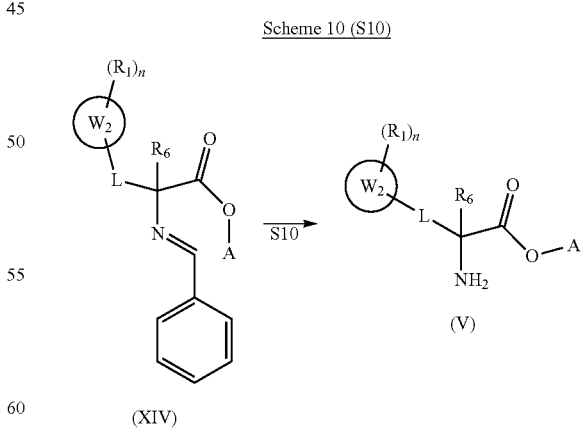

Typical reaction conditions comprise reacting a compound of formula (XIV) in a suitable solvent, such as THF or 1,4-dioxane, in the presence of a suitable acid, such as hydrochloric acid, at an appropriate temperature, such as room (or ambient) temperature.

Compounds of formula (XIV) may be prepared according to Scheme 11/(S11) below by reaction of a compound of formula (XV) as below reported.

Scheme 11 (S11)

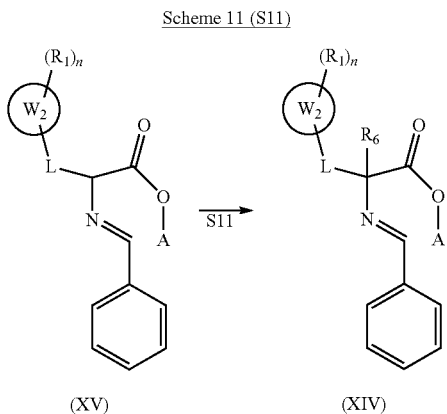

(XV)    (XIV)

Typical reaction conditions comprise reacting a compound of formula (XV) with an alkylating agent, such as para-formaldehyde or iodomethane, in a suitable solvent, such as THF or 1,4-dioxane, in the presence of a suitable base such as DBU or sodium hydride, at an appropriate temperature, such as 0° C. or room (or ambient) temperature.

Compounds of formula (XV) may be prepared according to Scheme 12/(S12) below by reaction of a compound of formula (XVI) as below reported.

Scheme 12 (S12)

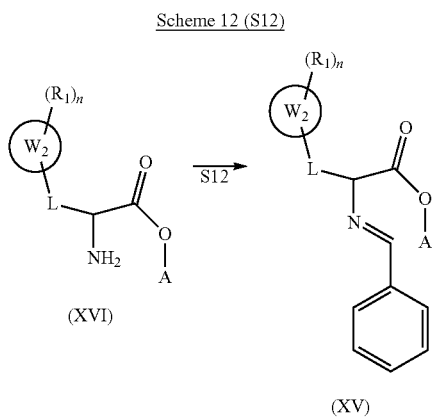

(XVI)

(XV)

Typical reaction conditions comprise reacting a compound of formula (XVI) with an arylcarboxaldehyde, such as benzaldehyde or 4-methoxybenzaldehyde, in a suitable solvent, such as acetonitrile, DCM or ethanol in the presence of an optional base, such as triethylamine, at an appropriate temperature, such as room (or ambient) temperature or 0° C. or 40° C.

Compounds of formula (XVI) may be prepared according to Scheme 13/(S13) below by reaction of a compound of formula (XVII) as below reported.

Scheme 13 (S13)

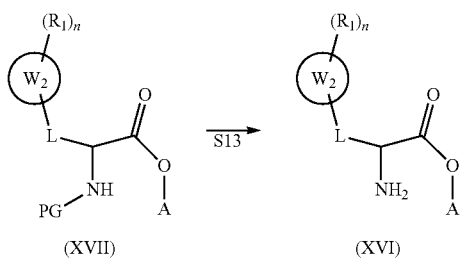

(XVII)    (XVI)

Typical reaction conditions comprise reacting a compound of formula (XVII) with a source of hydrogen, such as ammonium formate or gaseous hydrogen over a suitable catalyst, such as 10% Pd/C, in a suitable solvent, such as EtOAc, at an appropriate temperature, such as room (or ambient) temperature.

Compounds of formula (XVI) may also be prepared by reacting a compound of formula (XVII) in a suitable solvent, such as 1,4-dioxane, in the presence of a suitable acid, such as hydrochloric acid, at an appropriate temperature, such as room (or ambient) temperature.

Compounds of formula (XVII) may be prepared according to Scheme 14/(S14) below by reaction of a compound of formula (XVIII) with a compound of formula (VII) as below reported.

Scheme 14 (S14)

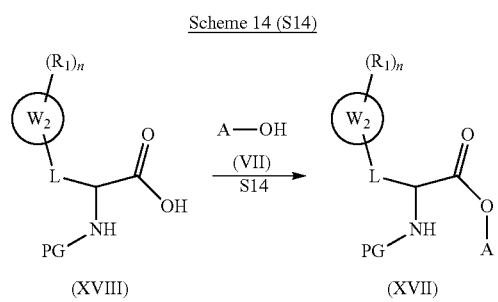

(XVIII)    (XVII)

Typical reaction conditions comprise reacting a compound of formula (XVIII) with a compound of formula (VII) in a suitable solvent, such as THF in the presence of a suitable coupling agent, such as DCC/HOBt or EDC/DMAP or HATU, at an appropriate temperature, such as room (or ambient) temperature or 40° C.

Compounds of formula (XVIII) may be prepared according to Scheme 15/(S15) below by reaction of a compound of formula (XIX) as below reported.

Scheme 15 (S15)

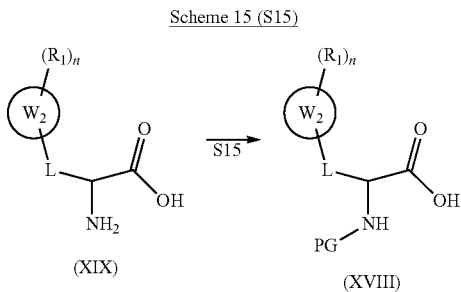

(XIX)    (XVIII)

Typical reaction conditions comprise reacting a compound of formula (XIX) with benzyl chloroformate or di-tert-butyl dicarbonate, in a suitable solvent, such as THF/water or 1,4-dioxane/water, in the presence of a suitable base such as sodium hydroxide, at an appropriate temperature, such as 0° C. or room (or ambient) temperature.
Scheme B
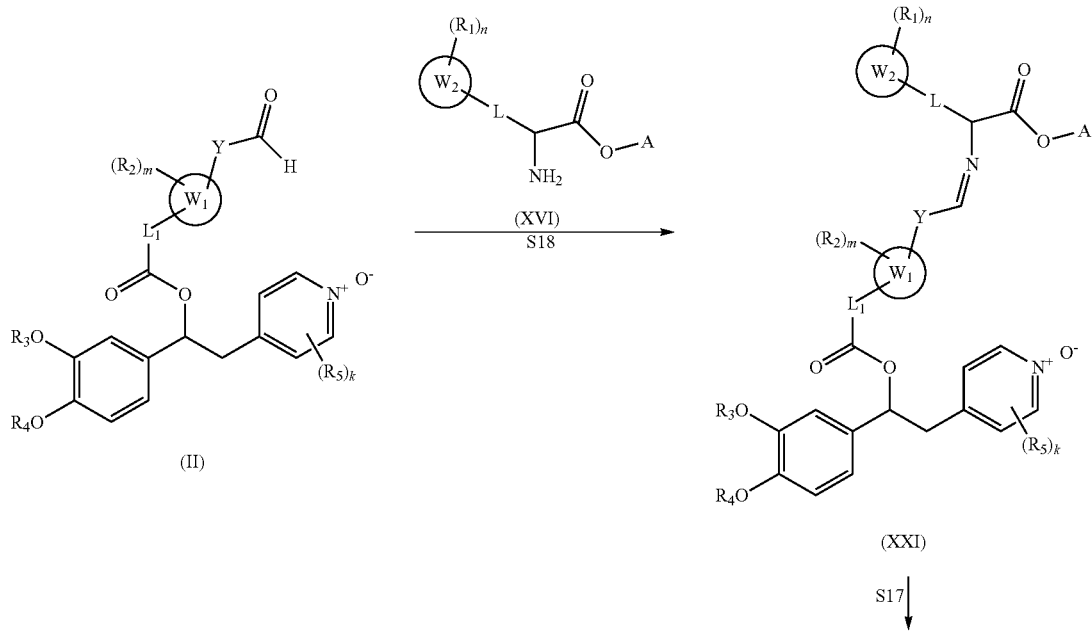

Compounds of formula (IA) may be prepared according to Scheme 16/(S16) below by reaction of a compound of formula (XX) as below reported.

Scheme 16 (S16)

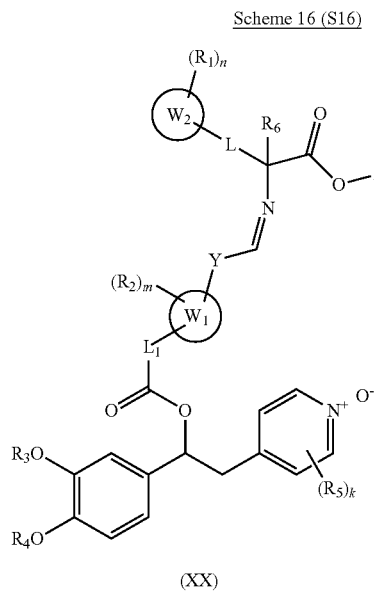

(XX)

Scheme 17 (S17)

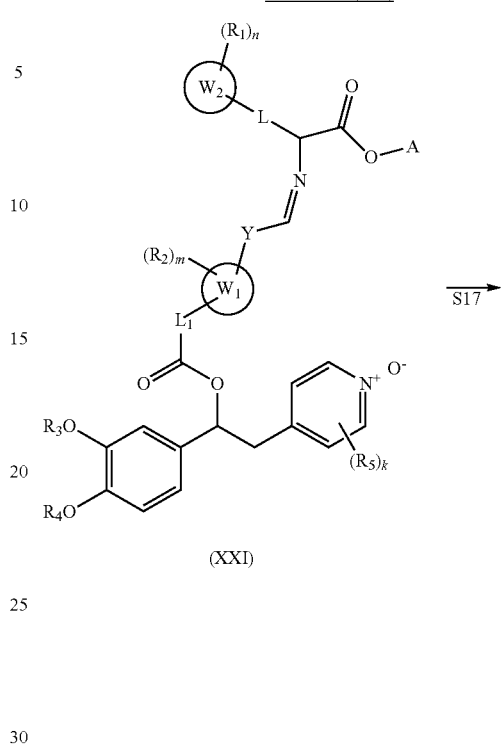

(XXI)

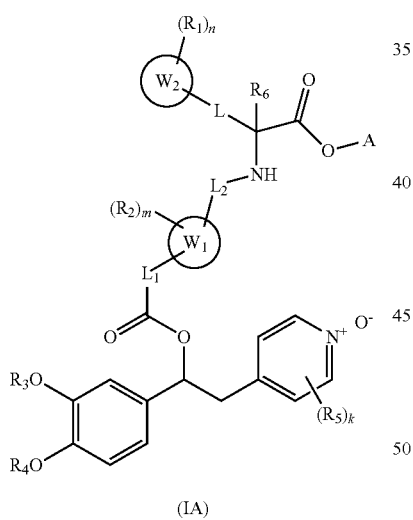

(IA)

Typical reaction conditions comprise reacting a compound of formula (XX) in a suitable solvent, such as acetonitrile, DCM or ethanol in the presence of an optional acid, such as acetic acid, and a reducing agent, such as $NaB(OAc)_3H$ or $NaBH_3CN$, at an appropriate temperature, such as room (or ambient) temperature or 0° C. or 40° C.

Compounds of formula (XX) may be prepared according to Scheme 17/(S17) below by reaction of a compound of formula (XXI) as below reported.

Typical reaction conditions comprise reacting a compound of formula (XXI) with an alkylating agent, such as para-formaldehyde, in a suitable solvent, such as THF or 1,4-dioxane, in the presence of a suitable base such as DBU or sodium hydride, at an appropriate temperature, such as 0° C. or room (or ambient) temperature.

Compounds of formula (XXI) may be prepared according to Scheme 18/(S18) below by reaction of a compound of formula (II) with a compound of formula (XVI) as below reported.

Scheme 18 (S18)

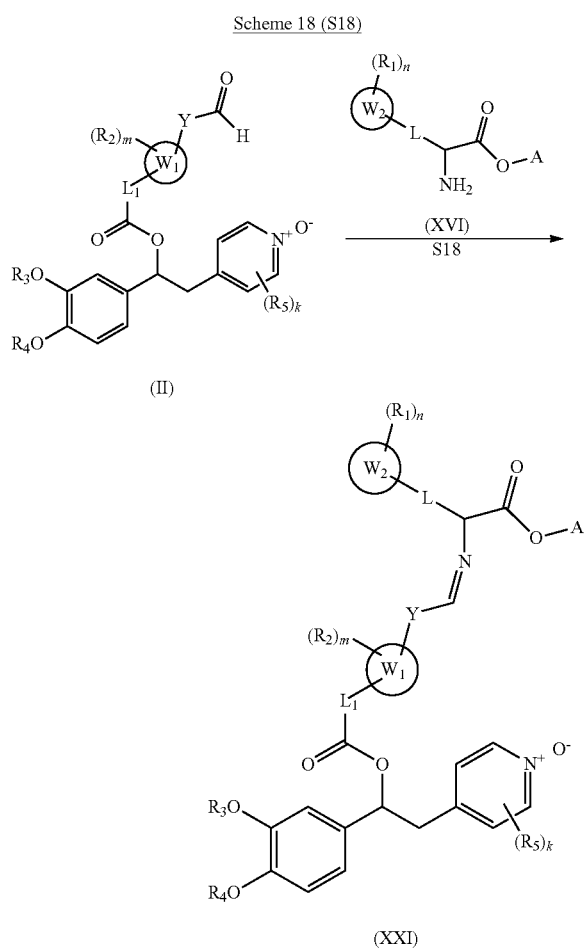

(II)

(XXI)

Typical reaction conditions comprise reacting a compound of formula (II) with a compound of formula (XVI) in a suitable solvent, such as acetonitrile, DCM or ethanol in the presence of an acid, such as acetic acid, and an optional base, such as triethylamine, at an appropriate temperature, such as room (or ambient) temperature or 0° C. or 40° C.

The processes described are particularly advantageous as they are susceptible of being properly modulated, through any proper variant known to the skilled person, so as to obtain any of the desired compounds of the invention. Such variants are comprised within the scope of the present invention.

From all of the above, it should be clear to the skilled person that any of the described groups may be present as such or in any properly protected form.

In particular, functional groups present in the compounds of formula II to XIII and which could generate unwanted side reactions and by-products, need to be properly protected before the alkylation, acylation, coupling, oxidation or sulfonylation takes place. Likewise, subsequent deprotection of those same protected groups may follow upon completion of the said reactions.

According to the present invention, unless otherwise indicated, the term "protecting group" designates a protective group adapted to preserve the function of the group it is bound to. Typically, protective groups are used to preserve amino, hydroxy, or carboxyl functions. Appropriate protecting groups may thus include, for example, benzyl, benzyloxycarbonyl, t-butoxycarbonyl, alkyl or benzyl esters or the like, which are well known to those skilled in the art [see, for a general reference, T.W. Green; Protective Groups in Organic Synthesis (Wiley, N.Y. 1999), which is incorporated herein by reference in it is entirety].

Likewise, selective protection and deprotection of any of the said groups, for instance including carbonyl, hydroxy or amino groups, may be accomplished according to very well-known methods commonly employed in organic synthetic chemistry.

Optional salification of the compounds of formula (I) may be carried out by properly converting any of the free acidic or amino groups into the corresponding pharmaceutically acceptable salts. In this case too, the operative conditions being employed for the optional salification of the compounds of the invention are all within the ordinary knowledge of the skilled person.

From all of the above, it should be clear to the skilled person that the above processes, comprehensive of any variant thereof for the preparation of suitable compounds of the invention, may be conveniently modified so that to adapt the reaction conditions to the specific needs, for instance by choosing appropriate condensing agents, solvents and protective groups, as the case may be.

The present invention also provides pharmaceutical compositions of compounds of the invention in admixture with one or more pharmaceutically acceptable carriers, for example those described in Remington's Pharmaceutical Sciences Handbook, XVII Ed., Mack Pub., N.Y., U.S.A., which is incorporated herein by reference in its entirety.

Administration of the compounds of the invention or may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration. Various solid oral dosage forms may be used for administering compounds of the invention including such solid forms as tablets, gelcaps, capsules, caplets, granules, lozenges and bulk powders. The compounds of the invention may be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms may also be used for administering compounds of the invention, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the invention may be injected, for example, intravenously, in the form of an isotonic sterile solution. Other preparations are also possible.

Suppositories for rectal administration of the compounds of the present invention may be prepared by mixing the compound with a suitable excipient such as cocoa butter, salicylates and polyethylene glycols.

Formulations for vaginal administration may be in the form of cream, gel, paste, foam, or spray formula containing, in addition to the active ingredient, such suitable carriers as are known in the art.

For topical administration the pharmaceutical composition may be in the form of creams, ointments, liniments, lotions, emulsions, suspensions, gels, solutions, pastes, powders, sprays, and drops suitable for administration to the skin, eye, ear or nose.

Topical administration may also involve transdermal administration via means such as transdermal patches.

For the treatment of the diseases of the respiratory tract, the compounds according to the invention are preferably administered by inhalation.

Inhalable preparations include inhalable powders, propellant-containing metered aerosols or propellant-free inhalable formulations and may be administered through a suitable inhalation device which may be respectively selected from dry powder inhaler, pressurized metered dosed inhaler, or a nebulizer.

For administration as a dry powder, single- or multi-dose inhalers known from the prior art may be utilized. In that case the powder may be filled in gelatine, plastic or other capsules, cartridges or blister packs or in a reservoir.

A diluent or carrier, generally non-toxic and chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic, or hydroalcoholic medium and they may be delivered by jet or ultrasonic nebulizers known from the prior art or by soft-mist nebulizers such as Respimat®.

The compounds of the invention may be administered as the sole active agent or in combination with other pharmaceutical active ingredients including those currently used in the treatment of respiratory disorders, e.g. beta2-agonists, antimuscarinic agents, corticosteroids, mitogen-activated protein kinases (P38 MAP kinase) inhibitors, nuclear factor kappa-B kinase subunit beta (IKK2) inhibitors, human neutrophil elastase (HNE) inhibitors, phosphodiesterase 4 (PDE4) inhibitors, leukotriene modulators, non-steroidal anti-inflammatory agents (NSAIDs) and mucus regulators.

The present invention also provides combinations of a compound of the invention, with a β2-agonist selected from the group consisting of carmoterol, vilanterol (GSK-642444), indacaterol, milveterol, arformoterol, formoterol, salbutamol, levalbuterol, terbutaline, AZD-3199, olodaterol (BI-1744-CL), abediterol (LAS-100977), bambuterol, isoproterenol, procaterol, clenbuterol, reproterol, fenoterol and ASF-1020 and salts thereof.

The present invention also provides combinations of a compound of the invention, with a corticosteroid selected from the group consisting of fluticasone propionate, fluticasone furoate, mometasone furoate, beclometasone dipropionate, ciclesonide, budesonide, GSK 685698, GSK 870086.

The present invention also provides combinations of a compound of the invention, with an antimuscarinic agent selected from the group consisting of aclidinium, tiotropium, ipratropium, trospium, glycopyrronium and oxitropium salts.

The present invention also provides combinations of a compound of the invention, with a PDE4 inhibitor selected from the group consisting of AN-2728, AN-2898, CBS-3595, apremilast, ELB-353, KF-66490, K-34, LAS-37779, IBFB-211913, AWD-12-281, cipamfylline, cilomilast, roflumilast, BAY19-8004 and SCH-351591, AN-6415, indus-82010, TPI-PD3, ELB-353, CC-11050, GSK-256066, oglemilast, OX-914, tetomilast, MEM-1414 and RPL-554.

The present invention also provides combinations of a compound of the invention, with a P38 MAP kinase inhibitor selected from the group consisting of semapimod, talmapimod, pirfenidone, PH-797804, GSK-725, minokine and losmapimod and salts thereof.

In a preferred embodiment, the present invention provides combinations of a compound of the invention with an IKK2 inhibitor.

The present invention also provides combinations of a compound of the invention with a HNE inhibitor selected from the group consisting of AAT, ADC-7828, Aeriva, TAPI, AE-3763, KRP-109, AX-9657, POL-6014, AER-002, AGTC-0106, respriva, AZD-9668, zemaira, AAT IV, PGX-100, elafin, SPHD-400, prolastin C and prolastin inhaled.

The present invention also provides combinations of a compound of the invention with a leukotriene modulator selected from the group consisting of montelukast, zafirlukast and pranlukast.

The present invention also provides combinations of a compound of the invention with a NSAID selected from the group consisting of ibuprofen and ketoprofen.

The present invention also provides combinations of a compound of the invention with a mucus regulator selected from the group consisting of INS-37217, diquafosol, sibenadet, CS-003, talnetant, DNK-333, MSI-1956 and gefitinib.

The dosages of the compounds of the invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of the invention may be administered for example, at a dosage comprised between 0.001 and 1000 mg/day, preferably between 0.1 and 500 mg/day.

When they are administered by inhalation route, the dosage of the compounds of the invention is advantageously comprised between 0.01 and 20 mg/day, preferably between 0.1 and 10 mg/day.

Preferably, the compounds of the invention alone or combined with other active ingredients may be administered for the prevention and/or treatment of any obstructive respiratory disease such as asthma, chronic bronchitis and chronic obstructive pulmonary disease (COPD).

The compounds of the invention may be administered for the prevention and/or treatment of any disease wherein PDE4 inhibition or M3 antagonism is required. Said disease include: allergic disease states such as atopic dermatitis, urticaria, allergic rhinitis, allergic conjunctivitis, vernal conjunctivitis, eosinophilic granuloma, psoriasis, inflammatory arthritis, rheumatoid arthritis, septic shock, ulcerative colitis, Crohn's disease, reperfusion injury of the myocardium and brain, chronic glomerulonephritis, endotoxic shock, cystic fibrosis, arterial restenosis, artherosclerosis, keratosis, rheumatoid spondylitis, osteoarthritis, pyresis, diabetes mellitus, pneumoconiosis, toxic and allergic contact eczema, atopic eczema, seborrheic eczema, lichen simplex, sunburn, pruritus in the anogenital area, alopecia areata, hypertrophic scars, discoid lupus erythematosus, systemic lupus erythematosus, follicular and wide-area pyodermias, endogenous and exogenous acne, acne rosacea, Behcet's disease, anaphylactoid purpura nephritis, inflammatory bowel disease, leukemia, multiple sclerosis, gastrointestinal diseases, autoimmune diseases and the like.

They also include neurological and psychiatric disorders such as Alzheimer's disease, multiple sclerosis, amylolateroslerosis (ALS), multiple systems atrophy (MSA), schizophrenia, Parkinson's disease, Huntington's disease, Pick's disease, depression, stroke, and spinal cord injury.

Other features of the invention will become apparent in the course of the following descriptions of exemplary embodiments which are given for illustration of the invention and are not intended to be limiting thereof.

EXAMPLES

Abbreviations

DCC=N,N'-dicyclohexylcarbodiimide;
HOBt=hydroxybenzotriazole;
HATU=(dimethylamino)-N,N-dimethyl(3H-[1,2,3]triazolo[4,5-b]pyridin-3-yloxy) methaniminium hexafluorophosphate;
EDC=1-ethyl-3-(3-dimethylaminopropyl) carbodiimide hydrochloride;
DBU=1,8-diazabicyclo[5.4.0]undec-7-ene;
DMAP=4-dimethylaminopyridine;
DMF=dimethylformamide;
DMSO=dimethyl sulfoxide;
EtOAc=ethyl acetate;
RT=room temperature;
THF=tetrahydrofuran;
DCM=dichloromethane;
MeOH=methyl alcohol;
EtOH=ethyl alcohol;
LHMDS=lithium bis(trimethylsilyl)amide;
m-CPBA=meta-chloroperoxybenzoic acid;
TFA=trifluoroacetic acid;
LC-MS=liquid chromatography/mass spectrometry;
NMR=nuclear magnetic resonance;
HPLC=high pressure liquid chromatography;
MPLC=medium pressure liquid chromatography;
SFC=supercritical fluid chromatography
General Experimental Details
Analytical Methods
Liquid Chromatography-Mass Spectrometry
Method 1

LC-MS was performed on a Waters 2795 Alliance HT HPLC with Waters 2996 Diode Array Detector coupled to a Micromass ZQ, single quadrupole mass spectrometer using a Phenomenex Luna C18 (2) column (5 μm, 100×4.6 mm plus guard cartridge) with a linear gradient of 5-95% acetonitrile/water (with 0.1% formic acid in each mobile phase) within 3.5 minutes and held at 95% for 2.0 minutes.
Method 2

LC-MS was performed on a Waters 2795 Alliance HT HPLC with Waters 2996 Diode Array Detector coupled to a Micromass ZQ, single quadrupole mass spectrometer using a Waters Xterra MS C18 column (5 μm, 100×4.6 mm plus guard cartridge) being initially held at 5% acetonitrile/water (with 10 mM ammonium bicarbonate in the aqueous mobile phase) for 0.5 minutes, followed by a linear gradient of 5-95% within 3.5 minutes and then held at 95% for 1.5 minutes.
Method 3

UPLC-MS was performed on a Waters Acquity I-Class with Waters Diode Array Detector coupled to a Waters SQD2 single quadrupole mass spectrometer using an Waters HSS C18 column (1.8 Gm, 100×2.1 mm) being initially held at 5% acetonitrile/water (with 0.1% formic acid in each mobile phase) for 1.2 minutes, followed by a linear gradient of 5-100% within 3.5 minutes and then held at 100% for 1.5 minutes (F=0.5 mL/min).
Method 4

UPLC-MS was performed on a Waters Acquity I-Class with Waters Diode Array Detector coupled to a Waters SQD2 single quadrupole mass spectrometer using a Waters BEH Shield RP18 column (1.7 μm, 100×2.1 mm) being initially held at 5% acetonitrile/water (with 10 mM ammonium bicarbonate in each mobile phase) for 1.2 minutes, followed by a linear gradient of 5-100% within 3.5 minutes and then held at 100% for 1.5 minutes (F=0.5 mL/min).

Supercritical Fluid Chromatography—Mass Spectrometry
Analytical Conditions
Method 5

SFC-MS was performed on a Waters/Thar SFC systems with Waters SQD using a Chiralpak IA column with a 55% iso-propyl alcohol/$CO_2$ (with 0.1% diethylamine) isocratic run at 5 mL/min, 120 Bar backpressure, 40° C. column temperature.
Method 6

SFC-MS was performed on a Waters/Thar SFC systems with Waters SQD using a Chiralpak IA column with a 5% methanol/$CO_2$ (with 0.1% diethylamine) isocratic run at 5 mL/min, 120 bar backpressure, 40° C. column temperature.
Method 7

SFC-MS was performed on a Waters/Thar SFC systems with Waters SQD using a YMC Amylose-C column with a 55% iso-propyl alcohol/$CO_2$ (with 0.1% diethylamine) isocratic run at 5 mL/min, 120 Bar backpressure, 40° C. column temperature.
Method 8

SFC-MS was performed on a Waters/Thar SFC systems with Waters SQD using a YMC Amylose-C column with a 50% iso-propyl alcohol/$CO_2$ (with 0.1% diethylamine) isocratic run at 5 mL/min, 120 Bar backpressure, 40° C. column temperature.
Method 9

SFC-MS was performed on a Waters/Thar SFC systems with Waters SQD using a YMC Amylose-C column with a 40% ethanol/$CO_2$ (with 0.1% diethylamine) isocratic run at 5 mL/min, 120 Bar backpressure, 40° C. column temperature.
Method 10

SFC-MS was performed on a Waters/Thar SFC systems with Waters SQD using a YMC Amylose-C column with a 40% iso-propyl alcohol/$CO_2$ (with 0.1% diethylamine) isocratic run at 5 mL/min, 120 Bar backpressure, 40° C. column temperature.
Chiral HPLC-Analytical Conditions
Method 11

Chiral HPLC was performed on an Agilent 1200 series HPLC system using a Chiralpak IA column with 50% iso-propyl alcohol/heptane (with 0.1% diethylamine) at 1 mL/min.
Method 12

Chiral HPLC was performed on an Agilent 1200 series HPLC system using a YMC Cellulose-C column with 50% iso-propyl alcohol/heptane (with 0.1% diethylamine) at 1 mL/min.
NMR

[1]H Nuclear magnetic resonance (NMR) spectroscopy was carried out using a Bruker instrument operating at 400 MHz using the stated solvent at around room temperature unless otherwise stated. In all cases, NMR data were consistent with the proposed structures. Characteristic chemical shifts (6) are given in parts-per-million using conventional abbreviations for designation of major peaks: e.g. s, singlet; d, doublet; t, triplet; q, quartet; dd, doublet of doublets; dt, doublet of triplets; m, multiplet; br, broad.

Preparative Reverse-Phase HPLC Conditions

Preparative HPLC purification was performed by reverse phase HPLC using a Waters Fractionlynx preparative HPLC system (2525 pump, 2996/2998 UV/VIS detector, 2767 liquid handler) or an equivalent HPLC system such as a Gilson Trilution UV directed system. The Waters 2767 liquid handler acted as both auto-sampler and fraction collector.

The columns used for the preparative purification of the compounds were a Waters Sunfire OBD Phenomenex Luna Phenyl Hexyl or Waters Xbridge Phenyl at 10 m 19×150 mm or Waters CSH Phenyl Hexyl, 19×150, 5 μm column.

Appropriate focused gradients were selected based on acetonitrile and methanol solvent systems under either acidic or basic conditions.

The modifiers used under acidic/basic conditions were formic acid or trifluoroacetic acid (0.1% V/V) and ammonium bicarbonate (10 mM) respectively.

The purification was controlled by Waters Fractionlynx software through monitoring at 210-400 nm, and triggered a threshold collection value at 260 nm and, when using the Fractionlynx, the presence of target molecular ion as observed under APi conditions. Collected fractions were analysed by LCMS (Waters Acquity systems with Waters SQD).

Compound Preparation

Where the preparation of starting materials is not described, these are commercially available, known in the literature, or readily obtainable by those skilled in the art using standard procedures. Where it is stated that compounds were prepared "analogously" or "similarly" to earlier examples or intermediates, it will be appreciated by the skilled person that the reaction time, number of equivalents of reagents and temperature can be modified for each specific reaction and that it may be necessary or desirable to employ different work-up or purification techniques.

Flash chromatography refers to silica gel chromatography and is carried out using an Isolera MPLC system (manufactured by Biotage); pre-packed silica gel cartridges (supplied by Biotage); or using conventional glass column chromatography.

In the procedures that follow, after each starting material, reference to a compound number may be provided. This is provided merely for assistance to the skilled chemist. The starting material may not necessarily have been prepared from the batch referred to.

Many of the compounds described in the following Examples have been prepared from stereochemically pure starting materials, for example 95% enantiomeric excess (ee).

The stereochemistry of the compounds in the Examples, where indicated, has been assigned on the assumption that absolute configuration at resolved stereogenic centers of staring materials is maintained throughout any subsequent reaction conditions.

Compounds isolated as single diastereoisomers whose absolute configuration at stereogenic center (2) in general formula (I) or (I') was not determined, are herebelow referred to as Single Diastereoisomers without mention in their chemical name of absolute configuration for the unknown stereogenic centre.

Chiral Separation Protocol

The diastereomeric separation of compounds was achieved either by chiral High Performance Liquid Chromatography (HPLC) using a Gilson Trilution preparative HPLC system (322 pump, 155 UV/VIS, GX281 liquid handler and fraction collector) or by Supercritical Fluid Chromatography (SFC) using a Waters Thar Prep100 preparative SFC system (P200 $CO_2$ pump, 2545 modifier pump, 2998 UV/VIS detector, 2767 liquid handler with Stacked Injection Module). The Waters 2767 liquid handler acted as both auto-sampler and fraction collector.

The column used for the preparative purification of the compounds was a Diacel Chiralpak IA/IB/IC, a Phenomenex Lux Cellulose-4, an YMC Amylose-C or an YMC Cellulose-C at 5 μm 250×20-21.2 mm ID.

Appropriate isocratic methods were selected based on methanol, ethanol or isopropanol solvent systems under un-modified or basic conditions.

The standard SFC method used was modifier, $CO_2$, 100 mL/min, 120 Bar backpressure, 40° C. column temperature. The standard HPLC method used was modifier, heptane, 5 mL/min and room temperature.

The modifier used under basic conditions was diethylamine (0.1% V/V). The modifier used under acidic conditions was either formic acid (0.1% V/V) or trifluoroacetic acid (0.1% V/V).

The SFC purification was controlled by Waters Fractionlynx software through monitoring at 210-400 nm and triggered at a threshold collection value, typically 260 nm. Collected fractions were analyzed by SFC (Waters/Thar SFC systems with Waters SQD). The fractions that contained the desired product were concentrated by vacuum centrifugation.

HPLC purification was controlled by Gilson Trilution software monitoring two wavelengths and triggered at a threshold collection value, typically 260 nm. Collected fractions were analyzed by HPLC (Agilent 1200 series HPLC system). The fractions that contained the desired product were concentrated by vacuum centrifugation.

Intermediate 1. [(1S)-2-(3,5-Dichloro-1-oxido-pyridin-1-ium-4-yl)-1-(3,4-dimethoxyphenyl)ethyl] 5-formyl-thiophene-2-carboxylate

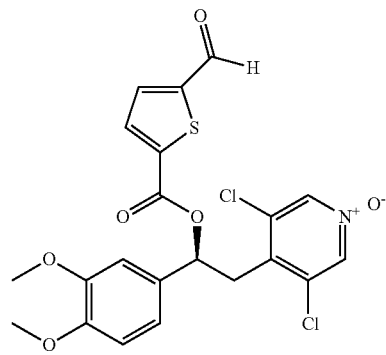

A stirred solution of 5-formyl-2-thiophenecarboxylic acid (400 mg, 2.56 mmol) in dichloromethane (20 mL) was added with (1S)-2-(3,5-dichloro-1-oxido-pyridin-1-ium-4-yl)-1-(3,4-dimethoxyphenyl)ethanol (compound I-1/A described in the co-pending International Patent Application No. PCT/EP2013/075520 (published as WO 2014/086849), which is incorporated herein by reference in its entirety)

(881 mg, 2.56 mmol) followed by 4-(dimethylamino)-pyridine (156 mg, 1.28 mmol) and N-(3-dimethylaminopropyl)-N'-ethylcarbodiimide hydrochloride (983 mg, 5.12 mmol). The resulting mixture was stirred at room temperature for 18 h. The reaction was partitioned between dichloromethane and saturated aqueous sodium bicarbonate solution. The organic layer was washed with brine, passed through a hydrophobic frit and the solvent was removed in vacuo. The crude material was purified by silica gel column chromatography, eluting with 0-100% EtOAc in DCM, to afford the title compound (488 mg, 39%) as yellow oil.

$^1$H NMR (400 MHz, CDCl3): δ 9.97 (s, 1H), 8.15 (s, 2H), 7.81 (d, J=3.6 Hz, 1H), 7.72 (d, J=3.6 Hz, 1H), 7.03-6.99 (m, 2H), 6.87 (d, J=8.7 Hz, 1H), 6.26 (dd, J=4.4, 10.0 Hz, 1H), 3.91 (s, 3H), 3.88 (s, 3H), 3.72 (dd, J=10.0, 14.0 Hz, 1H), 3.33 (dd, J=4.4, 14.0 Hz, 1H).

LCMS (Method 2): [MH+]=482 at 3.38 min.

The following intermediate was synthesized via a similar method to Intermediate 1.

temperature for 16 hours. The solvent was removed in vacuo and the aqueous layer was basified with 10% aqueous sodium hydroxide to pH z 13. The aqueous phase was back-extracted with EtOAc (2×50 mL). The aqueous phase was then acidified with 6 N HCl to pH 3-2. EtOAc (200 mL) was added and the reaction mixture stirred at room temperature for 16 hours. The layers were separated and the aqueous phase re-extracted with EtOAc (2×50 mL). The combined organic fractions were dried over MgSO4, filtered and the solvent was removed in vacuo to yield the title compound (1.34 g, 48%) as a clear oil. This oil was used in the next step without further purification.

$^1$H NMR (400 MHz, CDCl$_3$): δ 7.46 (d, J=7.4 Hz, 2H), 7.37-7.25 (m, 8H), 6.86-6.54 (m, 1H), 6.23-6.01 (m, 1H),) HH5.14-4.99 (m, 2H), 2.02 (s, 3H).).

LCMS (Method 1): [MH+]=300 at 2.68 min.

| Structure | Intermediate number | Analytical Data |
|---|---|---|
| 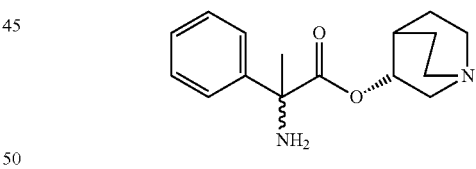 | Intermediate 2 | $^1$H NMR (400 MHz, CDCl$_3$): δ 10.09 (s, 1 H), 8.45 (s, 2 H), 8.19 (d, J = 8.1 Hz, 2 H), 7.94 (d, J = 8.1 Hz, 2 H), 7.08 (dd, J = 8.2, 2.1 Hz, 1 H), 6.99 (d, J = 2.0 Hz, 1 H), 6.87 (d, J = 8.3 Hz, 1 H), 6.36 (dd, J = 10.0, 4.3 Hz, 1 H), 3.90 (s, 3 H), 3.88 (s, 3 H), 3.83 (dd, J = 13.7, 10.0 Hz, 1 H), 3.43 (dd, J = 13.7, 4.4 Hz, 1 H). LCMS (Method 1): [MH+] = 460 at 4.45 min. |

Intermediate 3.
2-(Benzyloxycarbonylamino)-2-phenyl-propanoic acid

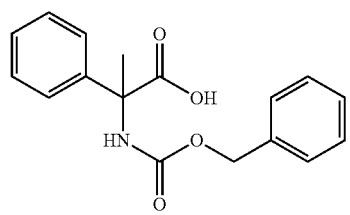 [SMILES: CC(NC(=O)OCc1ccccc1)(C(=O)O)c1ccccc1]

A solution of 2-amino-2-phenylpropanoic acid (1.65 g, 10 mmol) in a mixture of THF and water (1:1, 180 mL) at 0° C. was added with benzyl chloroformate (1.42 mL, 10 mmol) and NaOH (1 N, 10 mL, 10 mmol) simultaneously. The mixture was stirred at 0° C. for 1 hour. The ice bath was removed and the reaction mixture was stirred at room Intermediate 4. (R)-Quinuclidin-3-yl 2-amino-2-phenyl-propanoate A solution of 2-(benzyloxycarbonylamino)-2-phenyl-propanoic acid (1.34 g, 4.8 mmol) and N,N'-dicyclohexylcarbodiimide (1.2 g, 4.8 mmol) in dry THF (24 mL) was stirred at room temperature for 1 hour. 1-Hydroxybenzotriazole hydrate (777 mg, 5.8 mmol) and (R)-quinuclidin-3-ol (1.03 g, 8.11 mmol) were subsequently added and the resulting slurry was stirred at room temperature for 3 days. After this time, the reaction mixture was filtered through a pad of Celite® and the solvent was removed in vacuo. The residue was partitioned between EtOAc (100 mL) and saturated aqueous Na$_2$CO$_3$ (2×50 mL). The aqueous fraction was back-extracted with EtOAc (2×50 mL). The combined organic fractions were washed with brine (30 mL), dried over MgSO4, filtered and the solvent was removed in vacuo. The solid residue (844 mg) obtained was used in the next step without further purification. This residue was taken up in EtOAc (15 mL) and ammonium formate (750 mg, 11.91 mmol) and 10% Pd/C (550 mg) were added. The mixture was heated to 60° C. for 16 hours. After cooling the slurry to room temperature and filtration through a pad of Celite®, the solids were washed with EtOAc (150 mL). The solvent was removed in vacuo to yield the title compound as a mixture of two diastereoisomers (606 mg, 46% yield over two steps). The white solid was used in the next step without further purification.

$^1$H NMR (400 MHz, CDCl$_3$): δ 7.51-7.47 (m, 2H), 7.37-7.31 (m, 2H), 7.30-7.21 (m, 2H), 7.19-7.10 (m, 1H), 4.81-4.76 (m, 1H), 3.24-3.10 (m, 1H), 2.79-2.61* (m, 4H), 2.61-2.43† (m, 4H), 2.30-2.18 (m, 1H), 2.02-1.96* (m, 1H), 1.95-1.87† (m, 1H), 1.73† (s, 3H), 1.72* (s, 3H), 1.70-1.58 (m, 1H), 1.58-1.42 (m, 1H), 1.42-1.20 (m, 1H), 1.18-1.01 (m, 1H), † and * refer to different isomers (arbitrarily assigned).

LCMS (Method 2): [MH+]=275 at 2.70 min.

Intermediate 5. [(3R)-Quinuclidin-3-yl] 1-(tert-butoxycarbonylamino)indane-1-carboxylate

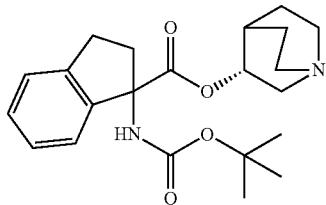 [SMILES: CC(C)(C)OC(=O)NC1(C(=O)O[C@H]2CN3CCC2CC3)CCc2ccccc21]

A solution of 1-(tert-butoxycarbonylamino)indane-1-carboxylic acid (1.0 g, 3.6 mmol) and N,N'-dicyclohexylcarbodiimide (1.1 g, 4.3 mmol) in THF (24 mL) was stirred at room temperature for 1 hour. 1-Hydroxybenzotriazole hydrate (577 mg, 4.3 mmol) and (R)-quinuclidin-3-ol (914 mg, 7.2 mmol) were subsequently added and the resulting slurry was stirred at room temperature for 3 days. After this time, the reaction mixture was filtered through a pad of Celite® and the solvent was removed in vacuo. The residue was partitioned between EtOAc (100 mL) and saturated aqueous Na$_2$CO$_3$ (2×50 mL), and the resulting aqueous fractions were re-extracted with EtOAc (2×50 mL). The combined organic fractions were washed with brine (30 mL), dried over Na$_2$SO$_4$, filtered and the solvent was removed in vacuo to yield a white foam (1.18 g, 85% yield) which was used in the next step without further purification.

$^1$H NMR (400 MHz, CDCl$_3$): δ 7.36-7.25 (m, 2H), 7.25-7.18 (m, 2H), 5.47-5.40 (m, 1H), 4.79-4.74 (m, 1H), 3.20-3.05 (m, 4H), 2.81-2.63 (m, 4H), 2.54† (d, J=14.9 Hz, 1H), 2.47-2.39* (m, 1H), 2.02-1.96† (m, 1H), 1.94-1.89* (m, 1H), 1.75-1.72† (m, 1H), 1.70-1.58 (m, 1H), 1.55-1.46 (m, 2H), 1.43 (bs, 9H), 1.17-0.99* (m, 1H), † and * refer to different isomers (arbitrarily assigned). LCMS (Method 2): [MH+]=287 at 3.08 min.

The following intermediates were synthesized via a similar method:

| Structure | Intermediate number | Analytical Data |
|---|---|---|
| 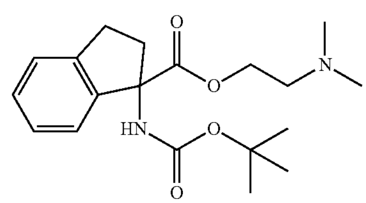 [SMILES: CN(C)CCOC(=O)C1(NC(=O)OC(C)(C)C)CCc2ccccc21] | Intermediate 12 | LCMS (Method 1): [MH+] = 349 at 2.51 min. |
| 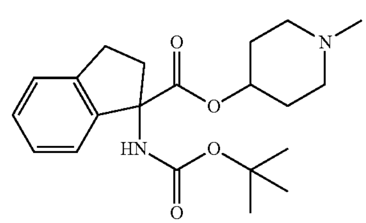 [SMILES: CN1CCC(OC(=O)C2(NC(=O)OC(C)(C)C)CCc3ccccc32)CC1] | Intermediate 13 | LCMS (Method 2): [MH+] = 375 at 3.65 min. |
| 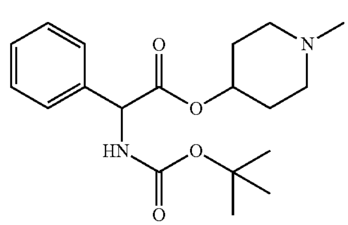 [SMILES: CN1CCC(OC(=O)C(NC(=O)OC(C)(C)C)c2ccccc2)CC1] | Intermediate 14 | LCMS (Method 2): [MH+] = 349 at 3.63 min. |

| Structure | Intermediate number | Analytical Data |
|---|---|---|
| 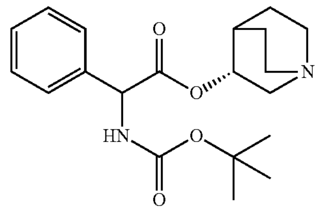 [SMILES: CC(C)(C)OC(=O)NC(C(=O)O[C@H]1CN2CCC1CC2)c1ccccc1] | Intermediate 15 | LCMS (Method 2): [MH+] = 361 at 3.30 min. |

Intermediate 16. (1-Methyl-4-piperidyl)-2-amino-2-phenyl-acetate bis hydrochloride

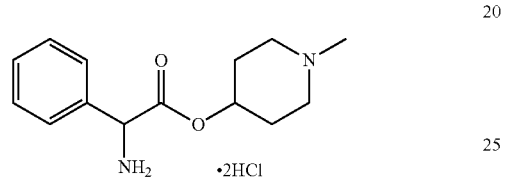

A solution of (1-methyl-4-piperidyl) 2-(tert-butoxycarbonylamino)-2-phenylacetate (2.60 g, 7.47 mmol) in 4 N HCl in dioxane (9.34 mL, 37.3 mmol) was stirred at room temperature for 18 hours. The solvent was removed by evaporation under reduced pressure and co-evaporated with diethyl ether to give the title compound as a yellow gum (2.80 g, quantitative yield).

LCMS (Method 2): [MH+]=249 at 1.93 min.

The following intermediate was synthesized via a similar method.

| Structure | Intermediate number | Analytical Data |
|---|---|---|
| 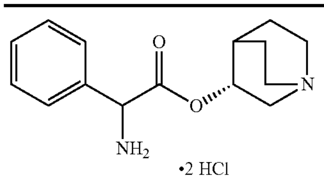 | Intermediate 17 | LCMS (Method 2): [MH+] = 261 at 2.05 min. |

Intermediate 6. Isopropyl 2-(tert-butylsulfinylamino)-2-phenyl-propanoate

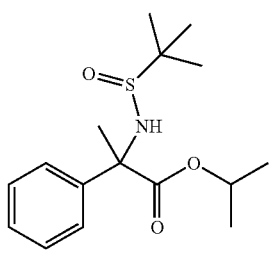 [SMILES: CC(C)OC(=O)C(C)(NS(=O)C(C)(C)C)c1ccccc1]

A solution of isopropyl-2-tert-butylsulfinylimino-2-phenyl-acetate (0.71 g, 2.40 mmol) in dry DCM (15 mL) was stirred under $N_2$ and cooled to −78° C. A 3.0M solution of methyl magnesium bromide in diethyl ether (1.2 mL, 3.60 mmol) was added drop wise over a period of 10 minutes then stirred at −78° C. for 1 hour. The mixture was quenched with drop wise addition of saturated $NaHCO_3$ solution (6 mL) followed by water (10 mL) and extracted with DCM (2×30 mL). The organic extracts were combined and washed with brine (20 mL) and filtered through a phase separator. The solvent was removed in vacuo to give the title compound as a mobile yellow oil (0.68 g, 91%).

LCMS (Method 2): [MH+]=312 at 2.87 min.

The following intermediate was synthesized via a similar method.

| Structure | Intermediate number | Analytical Data |
|---|---|---|
| ![Intermediate 7 structure] | Intermediate 7 | ¹H NMR (400 MHz, CDCl₃): δ 7.48-7.27 (m, 5 H), 5.09-5.02 (m, 1 H), 4.72 (s, 1 H), 2.55-2.30 (m, 2 H), 1.24-1.20 (m, 15 H), 0.97-0.88 (m, 3 H). |

Intermediate 8.
2-(tert-Butylsulfinylamino)-2-phenyl-propanoic acid

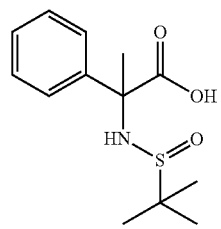 [SMILES: CC(NS(=O)C(C)(C)C)(C(=O)O)c1ccccc1]

A solution of isopropyl 2-(tert-butylsulfinylamino)-2-phenyl-propanoate (1.06 g, 3.41 mmol) and aqueous NaOH (2M, 5.1 mL, 10.2 mmol) in methanol (5 mL) was heated at 50° C. for 3 hours. After cooling to room temperature the mixture was diluted with EtOAc (30 mL) and extracted with water (2×20 mL). The aqueous phase was acidified to pH 5/6 with 1M HCl and removed the solvent in vacuo to give the title compound as a light brown solid (0.54 g). This was used in the next step without further purification.

LCMS (Method 2): [MH+]=270 at 2.05 and 2.18 min.

The following intermediate was synthesized via a similar method.

Intermediate 10. (1-Methyl-4-piperidyl) 2-(tert-butylsulfinylamino)-2-phenyl-propanoate

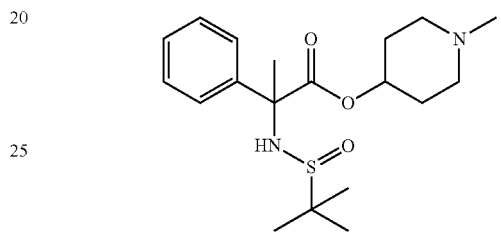

A mixture of 2-(tert-butylsulfinylamino)-2-phenyl-propanoic acid (0.27 g, 1.0 mmol), 1-methylpiperidin-4-ol (0.23 g, 2.0 mmol), N,N'-dicyclohexylcarbodiimide (0.41 g, 2.0 mmol) and 1-hydroxybenzotriazole hydrate (0.27 g, 2.0 mmol) in THF (25 mL) was stirred at room temperature for 42 hours. The mixture was filtered through a bed of Celite® and the solvent was removed in vacuo. The residue was partitioned between EtOAc (25 mL) and 2M aqueous Na₂CO₃ (2×50 mL). The organic phase was washed with brine (20 mL), separated and filtered through a phase separator. The solvent was removed in vacuo to yield a brown solid (0.23 g, 62% yield) which was used in the next step without further purification.

LCMS (Method 2): [MH+]=367 at 2.67 min.

The following intermediate was synthesized via a similar method.

| Structure | Intermediate number | Analytical Data |
|---|---|---|
| ![Intermediate 9 structure] | Intermediate 9 | ¹H NMR (400 MHz, DMSO): δ 7.42-7.13 m, 5 H), 5.82 (d, J = 7.5 Hz, 1 H), 2.37-2.26 (m, 1 H), 2.13-2.03 (m, 1 H), 1.03 (s, 9 H), 0.91-0.80 (m, 3 H). |

| Structure | Intermediate number | Analytical Data |
|---|---|---|
| 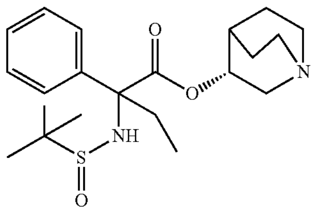 [SMILES: CCC(NS(=O)C(C)(C)C)(C(=O)O[C@H]1CN2CCC1CC2)c1ccccc1] | Intermediate 11 | $^1$H NMR (400 MHz, CDCl$_3$): δ 7.68 (br s, 1 H), 7.48-7.42 (m, 2 H), 7.37-7.29 (m, 3 H), 4.88-4.81 (m, 1 H), 3.32-3.09 (m, 1 H), 2.98-2.33 (m, 6 H), 2.20-1.86 (m, 2 H), 1.81-1.39 (m, 4 H), 1.25 (s, 9 H), 1.0-0.85 (m, 3 H) |

Example 1. [(1S)-2-(3,5-Dichloro-1-oxido-pyridin-1-ium-4-yl)-1-(3,4-dimethoxyphenyl)ethyl] 5-[[[1-methyl-2-oxo-1-phenyl-2-[(3R)-quinuclidin-3-yl]oxy-ethyl]amino]methyl]thiophene-2-carboxylate formate salt

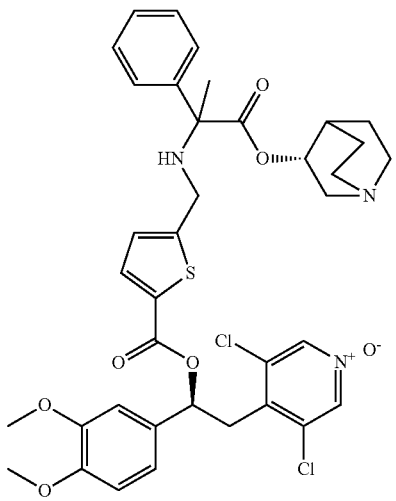

A suspension of (R)-quinuclidin-3-yl 2-amino-2-phenyl-propanoate (160 mg, 0.58 mmol) in CH3CN (5 mL) was added with [(1S)-2-(3,5-dichloro-1-oxido-pyridin-1-ium-4-yl)-1-(3,4-dimethoxyphenyl)ethyl] 5-formylthiophene-2-carboxylate (234 mg, 0.49 mmol) followed by acetic acid (0.07 mL, 1.0 mmol) and oven dried 3 Å crushed molecular sieves (200 mg). The resulting slurry was stirred at room temperature for 2 days. NaBH(OAc)$_3$ (513 mg, 2.23 mmol) was added in one portion and the reaction mixture was stirred at room temperature for a further 3.5 hours. The reaction mixture was filtered over a pad of Celite® and the solids were washed with EtOAc (100 mL). The filtrate was then concentrated in vacuo and the residue was purified by preparative HPLC, using formic acid as acidic modifiers of the chromatographic solvent, to give the title compound (1:1 mixture of diastereoisomers) as a pale yellow solid (128 mg, 35% yield).

$^1$H NMR (400 MHz, CD$_3$CN): δ 8.27 (s, 1H), 8.19 (s, 2H), 7.69 (dd, J=3.8, 1.8 Hz, 1H), 7.59-7.54 (m, 2H), 7.42 (t, J=7.5 Hz, 2H), 7.38-7.30 (m, 1H), 7.08-7.02 (m, 2H), 6.98-6.93 (m, 2H), 6.18 (dd, J=9.6, 4.5 Hz, 1H), 4.98-4.90 (m, 1H), 3.94-3.86 (m, 2H), 3.84 (m, 3H), 3.84-3.79 (m, 4H), 3.68 (dd, J=14.2, 9.6 Hz, 1H), 3.35 (dd, J=13.9, 4.8 Hz, 3H), 2.90-2.79 (m, 3H), 2.80-2.60 (m, 2H), 2.09-2.00 (m, 1H), 1.86-1.70 (m, 2H), 1.72† (s, 3H), 1.70* (s, 3H), 1.82-1.48 (m, 2H), 1.55-1.33 (m, 1H), † and * refer to different isomers (arbitrarily assigned). LCMS (Method 1): [MH+]=740 at 2.67 min.

The following compound was synthesized as mixture of diastereoisomers via the same method

| Structure | Reference | Analytical Data |
|---|---|---|
| [(1S)-2-(3,5-dichloro-1-oxido-pyridin-1-ium-4-yl)-1-(3,4-dimethoxyphenyl)ethyl] 4-[[[1-methyl-2-oxo-1-phenyl-2-[(3R)-quinuclidin-3-yl]oxy-ethyl]amino]methyl]benzoate formate salt | Example 2 | $^1$H NMR (400 MHz, CD$_3$CN): δ 8.25 (s, 1 H), 8.18 (s, 2 H), 8.02 (d, J = 8.1 Hz, 2 H), 7.56 (d, J = 7.8 Hz, 2 H), 7.53 (d, J = 8.1 Hz, 2 H), 7.40 (t, J = 7.6 Hz, 2 H), 7.32 (t, J = 7.2 Hz, 1 H), 7.10 (d, J = 2.0 Hz, 1 H), 7.06 (dd, J = 8.3, 2.0 Hz, 1 H), 6.95 (d, J = 8.2 Hz, 1 H), 6.26 (dd, J = 9.6, 4.5 Hz, 1 H), 4.91-4.86 (m, 1 H), 3.84 (s, 3 H), 3.82 (s, 3 H), 3.76 (d, J = 3.8 Hz, 2 H), 3.71 (dd, J = 14.2, 9.6 Hz, 1 H), 3.37 (dd, J = 14.1, 4.6 Hz, 1 H), 3.23 (ddd, J = 14.6, 8.3, 2.4 Hz, 1 H), 2.88-2.72 (m, 3 H), 2.71-2.58 (m, 2 H), 2.04-1.98 (m, 1 H), 1.77-1.71 (m, 1 H), 1.70 (s, 3 H), 1.66-1.55 (m, 2 H), 1.44-1.35 (m, 1 H), NH not observed. LCMS (Method 1): [MH+] = 734 at 2.47 min. |

Example 3. [(3R)-Quinuclidin-3-yl] 1-[[4-[(1S)-2-(3,5-dichloro-1-oxido-pyridin-1-ium-4-yl)-1-(3,4-dimethoxyphenyl)ethoxy] carbonylphenyl] methylamino]indane-1-carboxylate

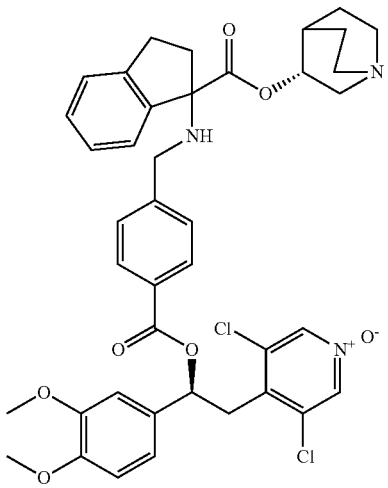

A solution of [(3R)-quinuclidin-3-yl] 1-(tert-butoxycarbonylamino)indane-1-carboxylate (190 mg, 0.49 mmol) in EtOAc (5 mL) was added with a solution of hydrogen chloride in dioxane, (4 N, 5 mL, 20 mmol) at 0° C. The resulting mixture was stirred at room temperature for 18 hours. The solvent was removed in vacuo and the crude residue was diluted in EtOH (8 mL). [(1S)-2-(3,5-dichloro-1-oxido-pyridin-1-ium-4-yl)-1-(3,4-dimethoxyphenyl)ethyl] 4-formylbenzoate (113 mg, 0.33 mmol), Et$_3$N (0.19 mL, 1.33 mmol) and acetic acid (0.03 mL, 0.5 mmol) were added and the mixture stirred at room temperature for 1 hour. NaBH$_3$CN (42 mg, 0.66 mmol) was added in one portion and stirring was continued for 18 hours. The solvent was removed and the residue was partitioned between EtOAc (20 mL) and water (20 mL), and the aqueous fraction was back-extracted with EtOAc (2×20 mL). The combined organic fractions were washed with 0.2 N HCl (2×20 mL). The combined aqueous phases were saturated with NaCl and back-extracted with CHCl$_3$ (4×50 mL). The combined organic phases were passed through a hydrophobic frit and the solvent was removed in vacuo. The residue was then purified by preparative HPLC to yield the title compound as a white solid (149 mg, 61% over two steps).

$^1$H NMR (400 MHz, DMSO): δ 8.56 (s, 2H), 7.91 (d, J=7.8 Hz, 2H), 7.50-7.43 (m, 3H), 7.31-7.20 (m, 3H), 7.06-6.99 (m, 2H), 6.97 (d, J=8.3 Hz, 1H), 6.21 (dd, J=4.2, 9.7 Hz, 1H), 4.70-4.64 (m, 1H), 3.78 (s, 3H), 3.75 (s, 3H), 3.73-3.70 (m, 2H), 3.62 (dd, J=9.7, 14.1 Hz, 1H), 3.32-3.22 (m, 2H), 3.06-2.96 (m, 3H), 2.68-2.55 (m, 4H), 2.40 (d, J=14.6 Hz, 1H), 2.31 (d, J=16.6 Hz, 1H), 2.15 (td, J=8.5, 13.0 Hz, 1H), 1.86-1.83† (m, 1H), 1.81-1.76* (m, 1H), 1.59-1.50 (m, 1H), 1.45-1.40 (m, 1H), 1.27-1.14 (m, 1H) † and * refer to different isomers (arbitrarily assigned). LCMS (Method 1): [MH+]=746 at 2.46 min.

The following compound was synthesized as mixture of diastereoisomers via the same method

| Structure | Reference | Analytical Data |
|---|---|---|
| [(1S)-2-(3,5-dichloro-1-oxido-pyridin-1-ium-4-yl)-1-(3,4-dimethoxyphenyl)ethyl] 5-[[[1-[(3R)-quinuclidin-3-yl]oxycarbonylindan-1-yl]amino]methyl]thiophene-2-carboxylate | Example 4 | $^1$H NMR (400 MHz, CD$_3$CN): δ 8.19† (s, 2 H), 8.19* (s, 2 H), 7.67† (s, 1 H), 7.66* (s, 1 H), 7.38 (dd, J = 3.4, 7.5 Hz, 1 H), 7.35-7.28 (m, 2 H), 7.27-7.22 (m, 1 H), 7.06-7.01 (m, 2 H), 6.96-6.93 (m, 2 H), 6.17 (dd, J = 4.5, 9.6 Hz, 1 H), 4.80-4.75 (m, 1 H), 3.99-3.86 (m, 2 H), 3.83† (s, 3 H), 3.83* (s, 3 H), 3.82 (s, 3 H), 3.70-3.63 (m, 2 H), 3.34 (dd, J = 4.5, 14.1 Hz, 1 H), 3.17-3.03 (m, 3 H), 2.77-2.60 (m, 5 H), 2.55 (d, J = 15.7 Hz, 1 H), 2.44 (d, J = 14.8 Hz, 1 H), 2.00-1.91 (m, 1 H), 1.88-1.81 (m, 1 H), 1.69-1.59 (m, 1 H), 1.55-1.49 (m, 1 H), 1.37-1.27 (m, 1 H) † and * refer to different isomers (arbitrarily assigned). LCMS (Method 1): [MH+] = 752 at 2.63 min. |

Example 5. [(1S)-2-(3,5-Dichloro-1-oxido-pyridin-1-ium-4-yl)-1-(3,4-dimethoxyphenyl)ethyl] 5-[[[1-methyl-2-[(1-methyl-4-piperidyl)oxy]-2-oxo-1-phenyl-ethyl]amino]methyl]thiophene-2-carboxylate

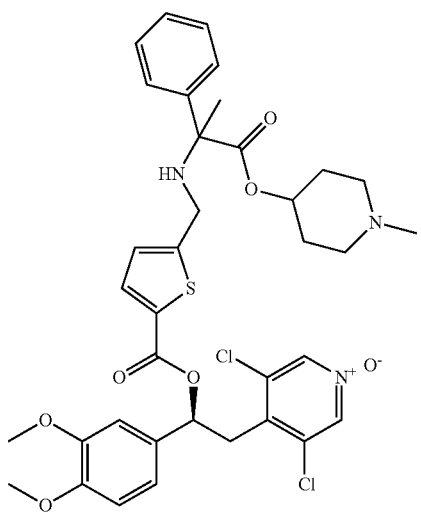

A solution of (1-methyl-4-piperidyl) 2-(tert-butylsulfinylamino)-2-phenyl-propanoate (0.30 g, 0.84 mmol) in 4 N hydrogen chloride in dioxane (1.1 mL, 4.18 mmol) was stirred at room temperature for 2 hours. The solvent was removed in vacuo and the residue was mixed with a solution of [(1S)-2-(3,5-dichloro-1-oxido-pyridin-1-ium-4-yl)-1-(3,4-dimethoxyphenyl)ethyl] 5-formylthiophene-2-carboxylate (0.27 g, 0.56 mmol) in DCM (20 mL). Et$_3$N (0.23 mL, 1.68 mmol) followed by acetic acid (0.048 mL, 0.84 mmol) were added and the mixture was stirred at room temperature for 24 hours. NaBH(OAc)$_3$ (0.70 g, 3.36 mmol) was added and the reaction mixture was stirred at room temperature for a further 5 days. The mixture was diluted with DCM (10 mL), washed with saturated NaHCO$_3$ solution (2×15 mL) and saturated NaCl (15 mL), filtered through a phase separator and the solvent was removed in vacuo. Purification by preparative HPLC gave the title compound as a pale yellow solid, (0.16 g, 39%).

$^1$H NMR (400 MHz, DMSO): δ 8.63 (s, 2H), 8.62 (s, 2H), 8.22 (s, 2H), 7.73 (d, J=3.8 Hz, 1H), 7.54-7.51 (m, 2H), 7.43 (dd, J=7.6, 7.6 Hz, 2H), 7.34 (dd, J=7.2, 7.2 Hz, 1H), 7.09-7.03 (m, 4H), 6.19 (dd, J=4.3, 9.9 Hz, 1H), 4.84 (dd, J=3.4, 3.4 Hz, 1H), 3.94-3.86 (m, 2H), 3.84 (s, 3H), 3.81 (s, 3H), 3.68-3.60 (m, 1H), 3.36 (d, J=18.4 Hz, 1 H), 2.49-2.36 (m, 2H), 2.29 (d, J=47.3 Hz, 2H), 2.19 (s, 3H), 2.13 (s, 1H), 1.81 (d, J=5.1 Hz, 2H), 1.64 (s, 3H), 1.62-1.57 (m, 2H).

LCMS (Method 1): [MH+]=728 at 2.59 min.

The following compounds were synthesized as mixture of diastereoisomers via the same method.

| Structure | Reference | Analytical Data |
|---|---|---|
| [(1S)-2-(3,5-dichloro-1-oxido-pyridin-1-ium-4-yl)-1-(3,4-dimethoxyphenyl)ethyl] 5-[[[1-phenyl-1-[(3R)-quinuclidin-3-yl]oxycarbonyl-propyl]amino]methyl]thiophene-2-carboxylate<br>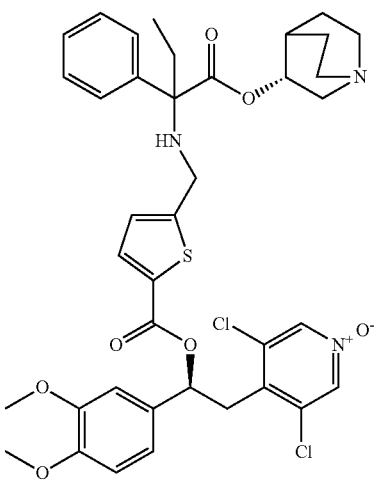 | Example 6 | $^1$H NMR (400 MHz, CD$_3$CN): δ 8.19 (s, 2 H), 7.68 (dd, J = 2.0, 3.8 Hz, 1 H), 7.58-7.54 (m, 2 H), 7.44-7.38 (m, 2 H), 7.36-7.30 (m, 1 H), 7.09-7.03 (m, 2 H), 6.98-6.94 (m, 2 H), 6.21-6.16 (m, 1 H), 4.82-4.79 (m, 1 H), 3.87-3.80 (m, 6 H), 3.80-3.65 (m, 4 H), 3.35 (dd, J = 4.5, 14.1 Hz, 1 H), 3.19-3.08 (m, 1 H), 2.93-2.86 (m, 1 H), 2.72-2.61 (m, 4 H), 2.58-2.52 (m, 1 H), 2.51-2.38 (m, 1 H), 2.37-2.28 (m, 1 H), 2.14-2.08 (m, 3 H), 1.92-1.89 (m, 1 H), 1.70-1.41 (m, 5 H), 1.33-1.24 (m, 1 H), 0.90-0.82 (m, 3 H). LCMS (Method 2): [MH+] = 754 at 3.50 min. |

| Structure | Reference | Analytical Data |
|---|---|---|
| [(1S)-2-(3,5-dichloro-1-oxido-pyridin-1-ium-4-yl)-1-(3,4-dimethoxyphenyl)ethyl] 5-[[[1-(2-dimethylaminoethyloxycarbonyl)indan-1-yl]amino]methyl]thiophene-2-carboxylate 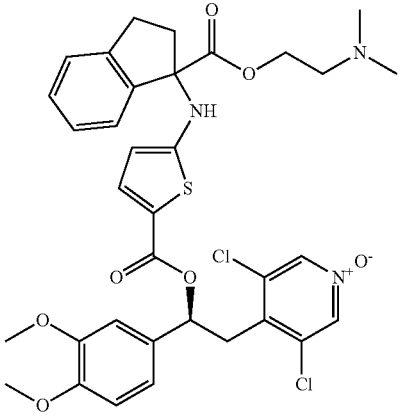 | Example 17 | $^1$H NMR (400 MHz, CDCl$_3$): δ 8.13*$^{or\dagger}$ (s, 2 H), 8.12*$^{or\dagger}$ (s, 2 H), 7.64-7.58 (m, 1 H), 7.34-7.17 (m, 4 H), 7.00-6.94 (m, 2 H), 6.89-6.81 (m, 2 H), 6.21 (dd, J = 4.2, 9.5 Hz, 1 H), 4.25-4.23 (m, 2 H), 3.91-3.82 (m, 9 H), 3.65 (dd, J = 9.7, 13.8 Hz, 1 H), 3.30 (dd, J = 4.3, 13.9 Hz, 1 H), 3.10-3.08 (m, 2 H), 2.78-2.68 (m, 1H), 2.57-2.47 (m, 2 H), 2.22-2.19 (m, 7 H). * and † refer to different isomers. LCMS (Method 2): [MH+] = 714 at 3.77 min. |

Example 18. [(1S)-2-(3,5-dichloro-1-oxido-pyridin-1-ium-4-yl)-1-(3,4-dimethoxyphenyl)ethyl] 5-[[[1-[(1-methyl-4-piperidyl)oxycarbonyl]indan-1-yl]amino]methyl]thiophene-2-carboxylate

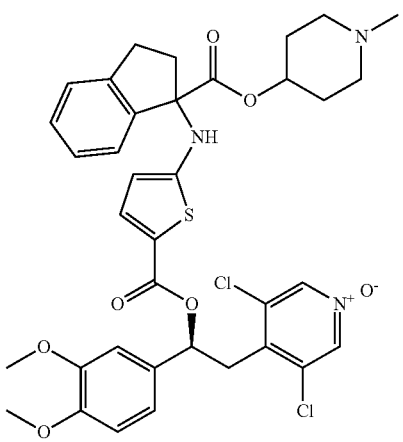

A solution of (1-methyl-4-piperidyl)-1-(tert-butoxycarbonylamino)indane-1-carboxylate (0.25 g, 0.67 mmol) in 4 N HCl in dioxane (1.0 mL, 4.0 mmol) was stirred at room temperature for 18 hours. The solvent was removed in vacuo to give a white solid. The previously obtained solid was dissolved in acetonitrile (5 mL) and [(1S)-2-(3,5-dichloro-1-oxidopyridin-1-ium-4-yl)-1-(3,4-dimethoxyphenyl)ethyl] 5-formylthiophene-2-carboxylate (322 mg, 0.67 mmol) was added followed by acetic acid (90 µL, 1.34 mmol). The resulting mixture was stirred at room temperature for 18 hours. The solvent was removed in vacuo and the residue azeotroped with toluene. The residue was taken up with acetonitrile (5 mL) and sodium triacetoxyborohydride (457 mg, 2.07 mmol) was added. The resulting mixture was stirred at room temperature for 18 hours. Additional sodium triacetoxyborohydride (457 mg, 2.07 mmol) was added and the stirring was maintained at room temperature for 4 hours. The solvent was removed in vacuo and the residue was taken up in water (30 mL) and ethyl acetate (100 mL). The layers were separated and the aqueous phase was extracted with ethyl acetate (2×20 mL). The combined organic phases were passed through a hydrophobic frit and the solvent was removed in vacuo. Purification of the crude material by preparative HPLC afforded the title compound (130 mg, 26%) as a white solid.

$^1$H NMR (400 MHz, CDCl$_3$): δ 8.14*$^{or\dagger}$ (s, 2H), 8.13*$^{or\dagger}$ (s, 2H), 7.63 (d, J=3.8 Hz, 1H), 7.30-7.27 (m, 3H), 7.24-7.18 (m, 1H), 7.00-6.95 (m, 2H), 6.88 (d, J=3.8 Hz, 1H), 6.84 (d, J=8.1 Hz, 1H), 6.21 (dd, J=4.4, 9.5 Hz, 1H), 4.85-4.81 (m, 1H), 3.91*$^{or\dagger}$ (s, 3H), 3.90*$^{or\dagger}$ (s, 3H), 3.87 (s, 3H), 3.88-3.81 (m, 2H), 3.65 (dd, J=10.0, 13.8 Hz, 1H), 3.30 (dd, J=4.5, 13.9 Hz, 1H), 3.11 (dd, J=7.2, 7.2 Hz, 2H), 2.76-2.68 (m, 1H), 2.50-2.42 (m, 1H), 3.35-2.14 (m, 3H), 2.22 (s, 3H), 1.92-1.85 (m, 1H), 1.83-1.77 (m, 1H), 1.75-1.68 (m, 1H), 1.56-1.52 (m, 2H). NH not visible, † and * refer to different isomers (arbitrarily assigned). LCMS (Method 1): [MH+]= 740 at 2.59 min.

Example 19. [(1S)-2-(3,5-dichloro-1-oxido-pyridin-1-ium-4-yl)-1-(3,4-dimethoxyphenyl)ethyl]-5-[[[1-(hydroxymethyl)-2-[(1-methyl-4-piperidyl)oxy]-2-oxo-1-phenyl-ethyl]amino]methyl]thiophene-2-carboxylate

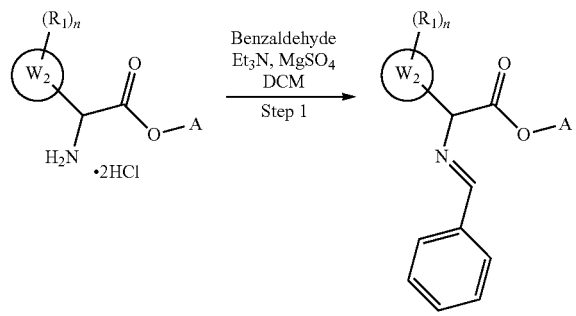
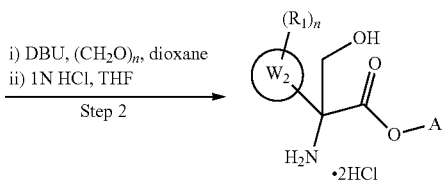
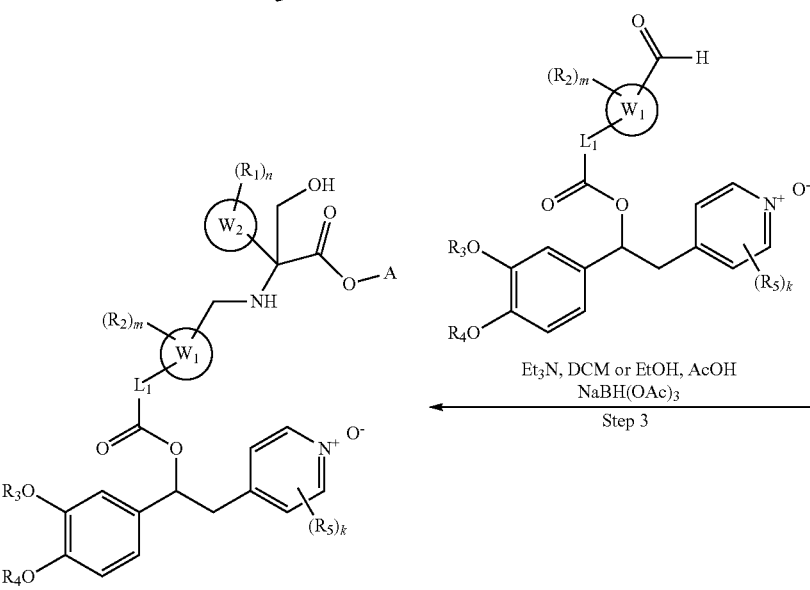

Step 1. Preparation of (1-methyl-4-piperidyl) 2-benzylideneamino-2-phenyl-acetate

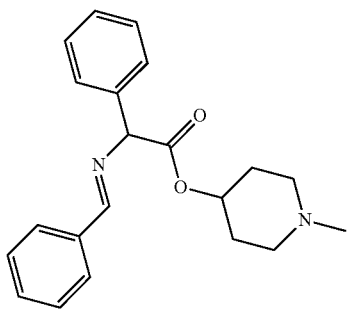 [SMILES: CN1CCC(OC(=O)C(/N=C/c2ccccc2)c2ccccc2)CC1]

To a solution of (1-methyl-4-piperidyl) 2-amino-2-phenyl-acetate, bis hydrochloride (650 mg, 2.02 mmol) in dry DCM (10 mL) was added $Et_3N$ (0.57 mL, 4.05 mmol) followed by $MgSO_4$. After stirring at room temperature for one hour, benzaldehyde (0.21 mL, 2.02 mmol) was added and the mixture was stirred at room temperature for 36 hours. The mixture was filtered, the solid was washed through with DCM, water (50 mL) was added to the filtrate, the biphasic mixture was filtered through a phase separator and the solvent was removed in vacuo to give the title compound as a yellow oil (586 mg, 86%). LCMS (Method 2): [MH+]=337 at 3.25 min.

Step 2. Preparation of (1-methyl-4-piperidyl) 2-amino-3-hydroxy-2-phenyl-propanoate bis hydrochloride

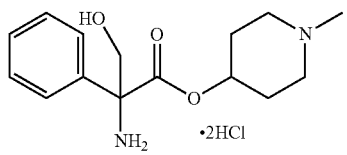 [SMILES: CN1CCC(OC(=O)C(N)(CO)c2ccccc2)CC1]

To a mixture of (1-methyl-4-piperidyl) 2-benzylideneamino-2-phenyl-acetate (0.28 g, 0.83 mmol) and para-formaldehyde (50 mg, 1.67 mmol) in dry dioxane (10 mL) was added DBU (0.15 mL, 1.0 mmol) and the mixture was stirred at room temperature for 3 hours. The solvent was removed by evaporation, the residue was dissolved in EtOAc (20 mL) and washed with water (2×10 mL). The aqueous phases were combined, back-extracted with EtOAc (10 mL). The organic extracts were combined, filtered through a phase separator frit and evaporated to dryness under reduced pressure to give a yellow gum. The obtained gum was treated with 1 N HCl (1 mL) in THF (1 mL) and stirred at room temperature for 18 hours. The solvent was removed in vacuo, the residue was taken up in 1 N HCl (3 mL) and washed with EtOAc (2×5 mL), the combined organic phases were back-extracted with 1 N HCl (3 mL). The combined aqueous extracts were evaporated to dryness under reduced pressure, co-evaporated with CH$_3$CN to give the title compounds as an off-white solid (155 mg, 53%). LCMS (Method 2): [MH+]=279 at 1.84 min.

Step 3. Preparation of [(1S)-2-(3,5-dichloro-1-oxido-pyridin-1-ium-4-yl)-1-(3,4-dimethoxyphenyl) ethyl] 5-[[[1-(hydroxymethyl)-2-[(1-methyl-4-piperidyl)oxy]-2-oxo-1-phenyl-ethyl]amino]methyl] thiophene-2-carboxylate

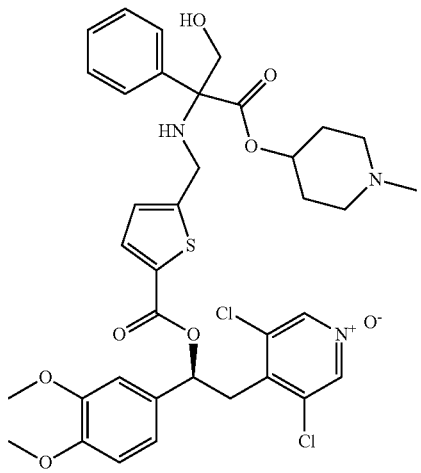

To a stirred mixture of [(1S)-2-(3,5-dichloro-1-oxido-pyridin-1-ium-4-yl)-1-(3,4-dimethoxyphenyl)ethyl] 5-formylthiophene-2-carboxylate (0.21 g, 0.43 mmol) and (1-methyl-4-piperidyl) 2-amino-3-hydroxy-2-phenyl-propanoate bis hydrochloride (0.15 g, 0.43 mmol) in DCM (5 mL) at room temperature was added Et$_3$N (0.12 mL, 0.85 mmol) followed by AcOH (24 μL, 0.43 mmol). The resulting mixture was stirred at room temperature for 20 hours. Sodium triacetoxyborohydride (0.27 g, 1.28 mmol) was added and the mixture was stirred at room temperature for 24 hours. Additional sodium triacetoxyborohydride (0.27 g, 1.28 mmol) and AcOH (24 μL, 0.43 mmol) were added and the mixture was stirred at room temperature for 72 hours. The reaction mixture was diluted with DCM (10 mL) and washed with saturated NaHCO$_3$ solution (2×20 mL), brine (10 mL), the organic phase was filtered through a phase separator frit and the solvent was removed in vacuo. Purification by preparative HPLC gave the title compound as an off-white solid (24.9 mg, 7.7%).

$^1$H NMR (400 MHz, CD$_3$CN): δ 8.20 (s, 2H), 7.68 (d, J=3.8 Hz, 1H), 7.52-7.48 (m, 2H), 7.40 (dd, J=7.3, 7.3 Hz, 2H), 7.34 (dd, J=7.2, 7.2 Hz, 1H), 7.08-7.02 (m, 2H), 6.97-6.92 (m, 2H), 6.18 (dd, J=4.7, 9.7 Hz, 1H), 4.91-4.87 (m, 1H), 4.17 (d, J=11.1 Hz, 1H), 3.95-3.94 (m, 2H), 3.84 (s, 3H), 3.82 (s, 3H), 3.80-3.72 (m, 1H), 3.68 (dd, J=9.6, 14.1 Hz, 1H), 3.39-3.32 (m, 1H), 3.25-3.13 (m, 2H), 2.51-2.31 (m, 2H), 2.40-2.20 (m, 2H), 2.15 (s, 3H), 1.86-1.81 (m, 2H), 1.69-1.60 (m, 2H).

LCMS (Method 1): [MH+]=744 at 2.7 min.

Example 20. [(1S)-2-(3,5-dichloro-1-oxido-pyridin-1-ium-4-yl)-1-(3,4-dimethoxyphenyl)ethyl] 5-[[[1-(hydroxymethyl)-2-oxo-1-phenyl-2-[(3R)-quinuclidin-3-yl]oxy-ethyl]-methyl-amino]methyl] thiophene-2-carboxylate

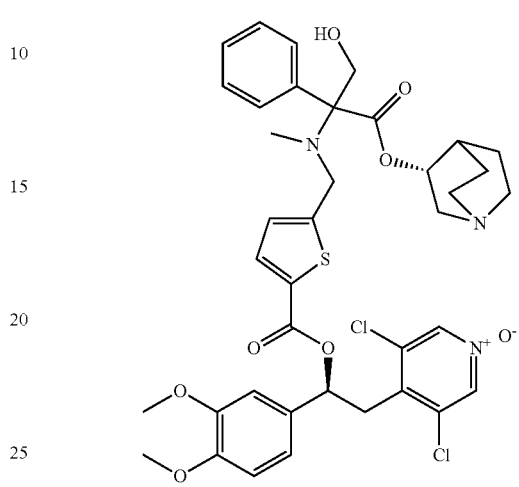

To a stirred mixture of [(1S)-2-(3,5-dichloro-1-oxido-pyridin-1-ium-4-yl)-1-(3,4-dimethoxyphenyl)ethyl] 5-formylthiophene-2-carboxylate (480 mg, 1.0 mmol) and [(3R)-quinuclidin-3-yl] 2-amino-2-phenyl-acetate, bis hydrochloride (480 mg, 1.4 mmol) in trifluoroethanol (10 mL) at room temperature was added Et$_3$N (0.4 mL, 2.9 mmol) followed by AcOH (115 μL, 2.0 mmol) and the mixture was stirred at room temperature for 72 hours. The solvent was removed in vacuo and the residue was azeotroped with toluene (3×10 mL) to give a yellow gum. This was suspended in dioxane (10 mL) and para-formaldehyde (300 mg, 10.0 mmol) was added. The resulting suspension was stirred at room temperature and DBU (0.18 mL, 1.2 mmol) was added and the mixture was stirred at room temperature for 3 hours. The solvent was removed in vacuo. The obtained residue was suspended in dry MeCN (20 mL) and sodium triacetoxyborohydride (1.05 g, 5.0 mmol) was added. The resulting mixture was stirred at room temperature for 18 hours. The solvent was removed in vacuo and the residue was partitioned between EtOAc (35 mL) and 1 N HCl (30 mL). The aqueous phase was washed again with EtOAc (35 mL) then basified with solid NaHCO$_3$ and extracted with EtOAc (2×25 mL). The combined organic extracts were filtered through a phase separator frit and the solvent was removed in vacuo. Purification by preparative HPLC gave the title compound as an off-white solid (73 mg, 9.5%).

$^1$H NMR (400 MHz, CD$_3$CN): δ 8.21*$^{ort}$ (s, 2H), 8.21*$^{ort}$ (s, 2H), 7.69*$^{ort}$ (d, J=1.2 Hz, 1H), 7.68*$^{ort}$ (d, J=1.4 Hz, 1H), 7.63-7.58 (m, 2H), 7.45-7.39 (m, 2H), 7.37-7.33 (m, 1H), 7.10-7.04 (m, 2H), 6.99-6.95 (m, 2H), 6.19 (ddd, J=1.8, 4.4, 9.7 Hz, 1H), 4.98-4.91 (m, 1H), 4.29-4.16 (m, 2H), 4.08-3.93 (m, 2H), 3.86 (s, 3H), 3.83 (s, 3H), 3.70 (dd, J=9.7, 14.0 Hz, 1H), 3.40-3.33 (m, 1H), 3.24-3.16 (m, 1H), 3.10-2.89 (m, 1H), 2.78-2.60 (m, 5H), 2.38*$^{ort}$ (s, 3H), 2.37*$^{ort}$ (s, 3H), 2.14-2.11 (m, 1H), 1.85-1.53 (m, 3H), 1.42-1.29 (m, 1H). † and * refer to different isomers (arbitrarily assigned). LCMS (Method 4): [MH+]=770 at 3.4 min.

Example 21. [(1S)-2-(3,5-dichloro-1-oxido-pyridin-1-ium-4-yl)-1-(3,4-dimethoxyphenyl)ethyl]-5-[[[1-(hydroxymethyl)-2-oxo-1-phenyl-2-[(3R)-quinuclidin-3-yl]oxy-ethyl]amino]methyl]thiophene-2-carboxylate

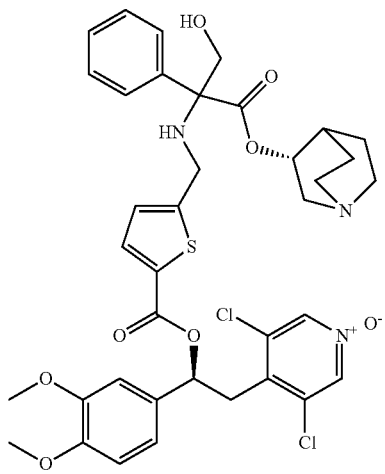

To a stirred mixture of [(1S)-2-(3,5-dichloro-1-oxido-pyridin-1-ium-4-yl)-1-(3,4-dimethoxyphenyl)ethyl] 5-formylthiophene-2-carboxylate (480 mg, 1.0 mmol) and [(3R)-quinuclidin-3-yl] 2-amino-2-phenyl-acetate, bis hydrochloride (480 mg, 1.4 mmol) in trifluoroethanol (10 mL) at room temperature was added Et₃N (0.4 mL, 2.9 mmol) followed by AcOH (115 µL, 2.0 mmol) and the mixture was stirred at room temperature for 72 hours. The solvent was removed in vacuo and the residue was azeotroped with toluene (3×10 mL) to give a yellow gum. This was suspended in dioxane (10 mL) and para-formaldehyde (300 mg, 10.0 mmol) was added. The resulting suspension was stirred at room temperature and DBU (0.18 mL, 1.2 mmol) was added and the mixture was stirred at room temperature for 3 hours. The solvent was removed in vacuo and the residue was partitioned between EtOAc (25 mL) and water (20 mL). The aqueous phase was further extracted with EtOAc (3×20 mL) and CHCl₃ (2×25 mL). The combined organic extracts were filtered through a phase separator frit and the solvent was removed in vacuo. The residue was dissolved in dry CH₃CN (10 mL), sodium triacetoxyborohydride (0.63 g, 3.0 mmol) was added and the mixture was stirred at room temperature overnight. The solvent was removed in vacuo, the residue was partitioned between EtOAc (40 mL) and 1N HCl (35 mL). The aqueous phase was further washed with EtOAc (35 mL) then basified with solid NaHCO₃ and extracted with EtOAc (20 mL) and CHCl₃ (3×30 mL). The combined organic extracts were filtered through a phase separator frit and the solvent was removed in vacuo. Purification by preparative HPLC gave the title compound as a light brown solid (150 mg, 20%).

$^1$H NMR (400 MHz, CD₃CN): δ 8.20*$^{or†}$ (s, 2H), 8.20*$^{or†}$ (s, 2H), 7.68*$^{or†}$ (d, J=2.0 Hz, 1H), 7.67*$^{or†}$ (d, J=2.0 Hz, 1H), 7.55-7.50 (m, 2H), 7.44-7.34 (m, 3H), 7.09-7.02 (m, 2H), 6.98-6.92 (m, 2H), 6.18 (dd, J=4.5, 9.9 Hz, 1H), 4.88-4.83 (m, 1H), 4.27-4.21 (m, 1H), 3.99-3.90 (m, 2H), 3.85 (s, 3H), 3.83 (s, 3H), 3.77 (d, J=13.9 Hz, 1H), 3.69 (dd, J=10.9, 14.7 Hz, 1H), 3.39-3.32 (m, 1H), 3.21-3.09 (m, 1H), 2.75-2.45 (m, 5H), 1.95-1.87 (m, 1H), 1.71-1.63 (m, 2H), 1.58-1.44 (m, 1H), 1.38-1.28 (m, 1H). † and * refer to different isomers (arbitrarily assigned) OH and NH not seen. LCMS (Method 4): [MH+]=756 at 3.31 min.

Example 22. [(1S)-2-(3,5-dichloro-1-oxido-pyridin-1-ium-4-yl)-1-(3,4-dimethoxyphenyl)ethyl] 5-[[[1-(methoxymethyl)-2-oxo-1-phenyl-2-[(3R)-quinuclidin-3-yl]oxy-ethyl]amino]methyl]thiophene-2-carboxylate

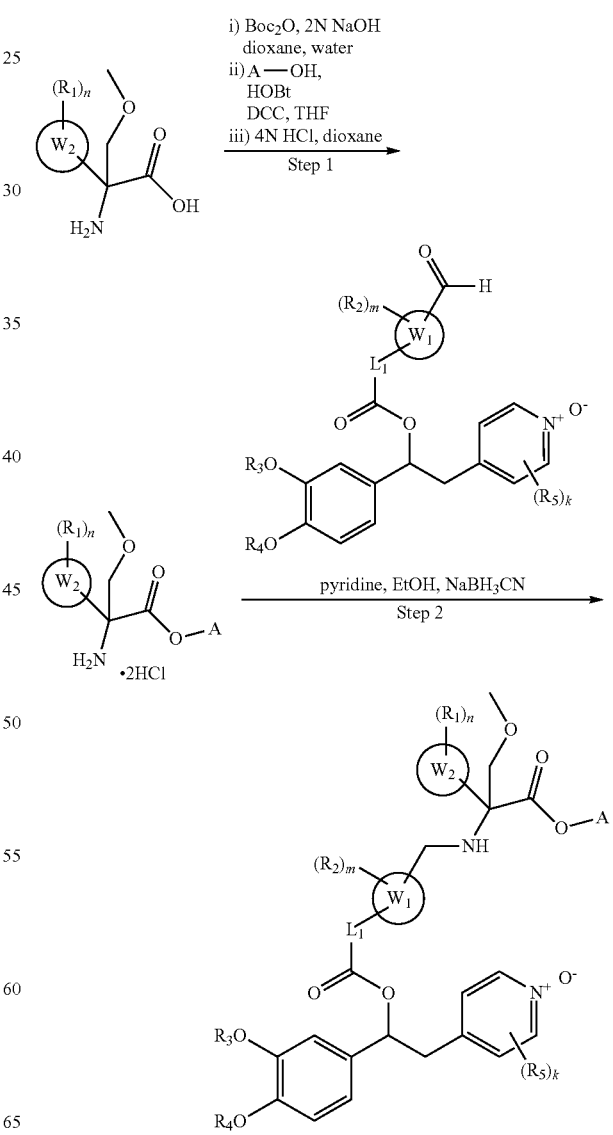

Step 1. Preparation of [(3R)-quinuclidin-3-yl] 2-amino-3-methoxy-2-phenyl-propanoate bis hydrochloride

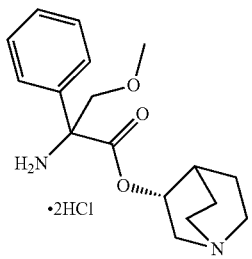 [SMILES: COCC(N)(C(=O)O[C@H]1CN2CCC1CC2)c1ccccc1]

·2HCl

Di-tert-butyl dicarbonate (1.12 g, 5.12 mmol) was added to a solution of 2-amino-3-methoxy-2-phenyl-propanoic acid (0.50 g, 2.56 mmol) and 2 N sodium hydroxide (3.85 mL, 7.70 mmol) in 2:1 dioxane:water (10 mL). The mixture was stirred for 18 hours then the solvents were removed under reduced pressure. The residue was cooled in an ice/water bath then 1M KHSO$_4$ was added carefully to pH 2. The mixture was extracted with ethyl acetate (3×10 mL). The combined organic extracts were dried over MgSO$_4$, filtered then concentrated under reduced pressure. The obtained residue was dissolved in THF (15 mL) and 3-(R)-quinuclidinol (0.36 g, 2.81 mmol), hydroxybenzotriazole (0.38 g, 2.81 mmol) and dicyclohexylcarbodiimide (0.58 g, 2.81 mmol) were added. The mixture was stirred for 8 days then filtered through Celite®. The filtrate was concentrated under reduced pressure then partitioned between ethyl acetate (20 mL) and saturated aqueous NaHCO$_3$ (20 mL). The combined organic extracts were washed with water, dried over MgSO$_4$, filtered then concentrated under reduced pressure to give an off-white foam which was suspended in 4 N HCl in dioxane (10 mL). The mixture was stirred for 20 hours then concentrated under reduced pressure to give the crude product as an off-white solid (0.56 g) in 58% yield.

LCMS (Method 3): [MH+]=304 at 1.02 min.

Step 2. Preparation of [(1S)-2-(3,5-dichloro-1-oxido-pyridin-1-ium-4-yl)-1-(3,4-dimethoxyphenyl)ethyl] 5-[[[1-(methoxymethyl)-2-oxo-1-phenyl-2-[(3R)-quinuclidin-3-yl]oxy-ethyl]amino]methyl]thiophene-2-carboxylate

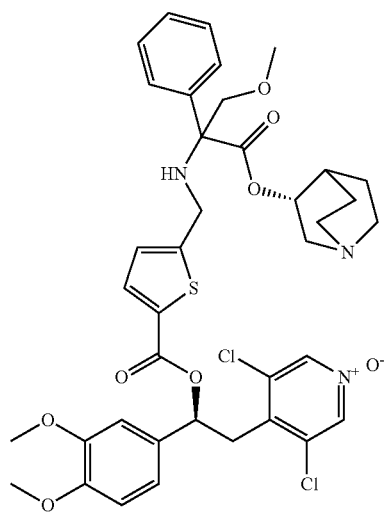

[(1S)-2-(3,5-Dichloro-1-oxido-pyridin-1-ium-4-yl)-1-(3,4-dimethoxyphenyl)ethyl]5-formylthiophene-2-carboxylate (282 mg, 0.59 mmol), and pyridine (0.066 mL, 0.82 mmol) was added to a solution of [(3R)-quinuclidin-3-yl] 2-amino-3-methoxy-2-phenyl-propanoate bis hydrochloride (0.31 g, 0.82 mmol) in ethanol (10 mL) at room temperature. The suspension was heated to 60° C. then the resulting solution was stirred for 10 minutes. Sodium cyanoborohydride (0.052 g, 0.82 mmol) was added and the mixture was stirred for 4 hours then concentrated under reduced pressure. The residue was partitioned between ethyl acetate (5 mL) and 2 N hydrochloric acid (5 mL). The aqueous was extracted with ethyl acetate (5 mL) then the combined organics were washed with 2 N hydrochloric acid (5 mL). The combined aqueous layers were basified with saturated aqueous NaHCO$_3$ then the mixture was extracted with ethyl acetate (3×10 mL). The combined organic extracts were dried over MgSO$_4$, filtered then concentrated under reduced pressure to give the crude product which was purified by preparative HPLC. This gave two fractions of differing purity which contained formic acid. Both fractions were individually basified with saturated aqueous NaHCO$_3$ then extracted with ethyl acetate (3×10 mL). The combined organic extracts were washed with 2 N hydrochloric acid (5 mL). The combined aqueous layers were basified with saturated aqueous NaHCO$_3$ then extracted with ethyl acetate (3×10 mL). Both fractions were determined to contain only the desired product so were combined. The organics were dried over MgSO$_4$, filtered then concentrated under reduced pressure to give the desired product as a white solid (28 mg, 4%).

$^1$H NMR (400 MHz, DMSO): δ 8.57 (s, 2H), 7.67 (dd, J=3.2, 3.2 Hz, 1H), 7.52 (dd, J=8.0, 8.0 Hz, 2H), 7.44-7.33 (m, 3H), 7.07-6.96 (m, 4H), 6.19-6.13 (m, 1H), 4.83-4.76 (m, 1H), 4.03-3.97 (m, 1H), 3.90 (dt, J=4.8, 12.2 Hz, 2H), 3.81 (s, 3H), 3.78 (s, 3H), 3.65-3.58 (m, 1H), 3.34*$^{or†}$ (s, 3H), 3.32*$^{or†}$ (s, 3H), 3.14-3.05 (m, 1H), 2.73-2.58 (m, 3H), 2.42-2.34*$^{or†}$ (m, 1H), 1.95-1.89*$^{or†}$ (m, 1H), 1.88-1.83*$^{or†}$ (m, 1H), 1.63-1.58 (m, 2H), 1.54-1.48 (m, 1H), 1.35-1.19 (m, 2H). † and * refer to different isomers (arbitrarily assigned). NH not seen. LCMS (Method 3): [MH+]=770 at 2.82 min.

Example 7 and Example 8. Single diastereoisomers of [(1S)-2-(3,5-dichloro-1-oxido-pyridin-1-ium-4-yl)-1-(3,4-dimethoxyphenyl)ethyl] 5-[[[1-methyl-2-oxo-1-phenyl-2-[(3R)-quinuclidin-3-yl]oxy-ethyl]amino]methyl]thiophene-2-carboxylate (Ex. 7, diast 1 and Ex. 8, diast 2)

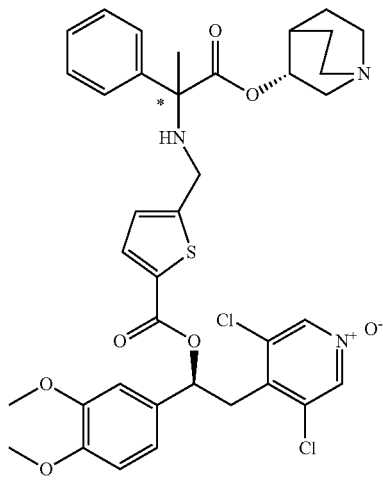

Purification of the 1:1 mixture of diastereoisomers of Example 1 by chiral preparative SFC afforded the single diastereoisomers. The absolute configurations of these were not determined.

Title compound (Example 7, single diastereoisomer 1) was obtained as a white solid (15 mg, 31%).

$^1$H NMR (400 MHz, CD$_3$CN): δ 8.20 (s, 2H), 7.68 (d, J=3.8 Hz, 1H), 7.59-7.52 (m, 2H), 7.41 (t, J=7.6 Hz, 2H), 7.33 (t, J=7.3 Hz, 1H), 7.07 (d, J=2.0 Hz, 1H), 7.04 (dd, J=8.2, 2.1 Hz, 1H), 6.97-6.92 (m, 2H), 6.18 (dd, J=9.6, 4.5 Hz, 1H), 4.87-4.82 (m, 1H), 3.88 (s, 2H), 3.84 (s, 3H), 3.82 (s, 3H), 3.68 (dd, J=14.1, 9.7 Hz, 1H), 3.35 (dd, J=14.1, 4.6 Hz, 1H), 3.24-3.13 (m, 1H), 3.05-2.85 (m, 1H), 2.82-2.64 (m, 4H), 2.60 (d, J=13.7 Hz, 1H), 1.93-1.89 (m, 1H), 1.71 (s, 3H), 1.69-1.62 (m, 1H), 1.70-1.44 (m, 2H), 1.38-1.27 (m, 1H). LCMS (Method 1): [MH+]=740 at 2.63 min.

Title compound (Example 8, single diastereoisomer 2) was obtained as a white solid (14 mg, 30%).

$^1$H NMR (400 MHz, CD$_3$CN): δ 8.20 (s, 2H), 7.69 (d, J=3.8 Hz, 1H), 7.59-7.54 (m, 2H), 7.44-7.39 (m, 2H), 7.37-7.30 (m, 1H), 7.08-7.02 (m, 2H), 7.00-6.94 (m, 2H), 6.18 (dd, J=9.7, 4.5 Hz, 1H), 5.00-4.94 (m, 1H), 3.91 (dd, J=20.8, 15.3 Hz, 2H), 3.84 (s, 3H), 3.82 (s, 3H), 3.73-3.63 (m, 1H), 3.34 (dd, J=13.8, 4.0 Hz, 1H), 3.38-3.27 (m, 1H), 3.05-2.80 (m, 4H), 2.80-2.67 (m, 2H), 2.12-2.07 (m, 1H), 1.86-1.74 (m, 1H), 1.84-1.55 (m, 2H), 1.69 (s, 3H), 1.53-1.42 (m, 1H). LCMS (Method 2): [MH+]=740 at 3.94 min.

Compounds reported in the table below were obtained as single diastereoisomers according to the procedure described in Examples 7 and 8 by chiral preparative SFC or chiral preparative HPLC.

| Structure | Reference | Analytical Data |
|---|---|---|
| [(1S)-2-(3,5-dichloro-1-oxido-pyridin-1-ium-4-yl)-1-(3,4-dimethoxyphenyl)ethyl] 4-[[[1-methyl-2-oxo-1-phenyl-2-[(3R)-quinuclidin-3-yl]oxy-ethyl]amino]methyl]benzoate | Example 9 (Diastereoisomer 1) | $^1$H NMR (400 MHz, CD$_3$CN): δ 8.15 (s, 2 H), 7.99 (d, J = 8.1 Hz, 2 H), 7.53 (dd, J = 7.9, 1.4 Hz, 2 H), 7.49 (d, J = 8.0 Hz, 2 H), 7.39-7.34 (m, 2 H), 7.29 (tt, J = 7.3, 1.5 Hz, 1 H), 7.07 (d, J = 2.1 Hz, 1 H), 7.03 (dd, J = 8.2, 2.1 Hz, 1 H), 6.92 (d, J = 8.2 Hz, 1 H), 6.23 (dd, J = 9.6, 4.6 Hz, 1 H), 4.81-4.74 (m, 1 H), 3.81 (s, 3 H), 3.79 (s, 3 H), 3.71 (d, J = 5.0 Hz, 2 H), 3.71-3.65 (m, 1 H), 3.35 (dd, J = 14.1, 4.6 Hz, 1 H), 3.12 (ddd, J = 14.6, 8.2, 2.3 Hz, 1 H), 2.71-2.57 (m, 4 H), 2.50 (dt, J = 14.7, 2.6 Hz, 1 H), 1.86 (dd, J = 6.7, 3.7 Hz, 1 H), 1.68 (s, 3 H), 1.65-1.57 (m, 1 H), 1.54-1.45 (m, 2 H), 1.30-1.21 (m, 3 H). LCMS (Method 1): [MH+] = 734 at 2.50 min. |
| [(3R)-quinuclidin-3-yl] 1-[[4-[(1S)-2-(3,5-dichloro-1-oxido-pyridin-1-ium-4-yl)-1-(3,4-dimethoxyphenyl)ethoxy]carbonylphenyl]methylamino]indane-1-carboxylate | Example 10 (Diastereoisomer 1) | $^1$H-NMR (400 MHz, DMSO): δ 8.56 (s, 2 H), 7.91 (d, J = 8.3 Hz, 2H), 7.48 (d, J = 8.4 Hz, 2 H), 7.45 (d, J = 7.1 Hz, 1 H), 7.30-7.20 (m, 3 H), 7.06-6.99 (m, 2 H), 6.97 (d, J = 8.3 Hz, 1 H), 6.21 (dd, J = 4.3, 9.6 Hz, 1 H), 4.67-4.64 (m, 1 H), 3.78 (m, 3 H), 3.75 (s, 3 H), 3.71 (d, J = 5.8 Hz, 2 H), 3.62 (dd, J = 9.7, 14.0 Hz, 1 H), 3.36-3.30 (m ,1 H), 3.29-3.22 (m, 1 H), 3.06-2.92 (m, 3 H), 2.68-2.53 (m, 4 H), 2.53-2.42 (m, 1 H), 2.30 (d, J = 14.9 Hz, 1 H), 2.15 (td, J = 8.1, 13.1 Hz, 1 H), 1.87-1.82 (m, 1 H), 1.60-1.50 (m, 2 H), 1.47-1.40 (m, 1 H), 1.30-1.21 (m, 1 H). LCMS (Method 2): [MH+] = 746 at 3.28 min. |

-continued

| Structure | Reference | Analytical Data |
|---|---|---|
| [(3R)-quinuclidin-3-yl] 1-[[4-[(1S)-2-(3,5-dichloro-1-oxido-pyridin-1-ium-4-yl)-1-(3,4-dimethoxyphenyl)ethoxy]carbonylphenyl]methylamino]indane-1-carboxylate | Example 11 (Diastereoisomer 2) | $^1$H-NMR (400 MHz, DMSO): δ 8.56 (s, 2 H), 7.91 (d, J = 8.3 Hz, 2 H), 7.48 (d, J = 8.1 Hz, 2 H), 7.44 (d, J = 7.5 Hz, 1 H), 7.31-7.20 (m, 3 H), 7.06-7.00 (m, 2 H), 6.97 (d, J = 8.3 Hz, 1 H), 6.21 (dd, J = 4.2, 9.7 Hz, 1 H), 4.71-4.65 (m, 1 H), 3.78 (s, 3 H), 3.75 (s, 3 H), 3.73-3.68 (m, 2 H), 3.62 (dd, J = 9.8, 14.0 Hz, 1 H), 3.37-3.28 (m, 1 H), 3.28-3.20 (m, 1 H), 3.08-2.97 (m, 3 H), 2.69-2.54 (m, 5 H), 2.40 (d, J = 14.1 Hz, 1 H), 2.15 (td, J = 8.2, 13.1 Hz, 1 H), 1.81-1.77 (m, 1 H), 1.58-1.49 (m, 1 H), 1.47-1.37 (m, 2 H), 1.25-1.15 (m, 1 H). LCMS (Method 2): [MH+] = 746 at 3.27 min. |
| [(1S)-2-(3,5-dichloro-1-oxido-pyridin-1-ium-4-yl)-1-(3,4-dimethoxyphenyl)ethyl] 5-[[[1-[(3R)-quinuclidin-3-yl]oxycarbonylindan-1-yl]amino]methyl]thiophene-2-carboxylate | Example 12 (Diastereoisomer 1) | $^1$H NMR (400 MHz, DMSO): δ 8.61 (s, 2 H), 7.71 (d, J = 3.8 Hz, 1 H), 7.48 (d, J = 7.1 Hz, 1 H), 7.37-7.26 (m, 3 H), 7.07-7.02 (m, 4 H), 6.18 (dd, J = 4.3, 9.6 Hz, 1 H), 4.77-4.72 (m, 1 H), 3.96-3.86 (m, 2 H), 3.81 (d, J = 6.8 Hz, 6 H), 3.75 (dd, J = 7.6, 7.6 Hz, 2 H), 3.68-3.57 (m, 1 H), 3.38-3.30 (m, 1 H), 3.15-2.99 (m, 3 H), 2.74-2.59 (m, 4 H), 2.48-2.35 (m, 1 H), 2.22-2.13 (m, 1 H), 1.92 (d, J = 2.5 Hz, 1 H), 1.67-1.47 (m, 3 H), 1.39-1.27 (m, 1 H). LCMS (Method 1): [MH+] = 752 at 2.61 min. |

-continued

| Structure | Reference | Analytical Data |
|---|---|---|
| [(1S)-2-(3,5-dichloro-1-oxido-pyridin-1-ium-4-yl)-1-(3,4-dimethoxyphenyl)ethyl] 5-[[[1-[(3R)-quinuclidin-3-yl]oxycarbonylindan-1-yl]amino]methyl]thiophene-2-carboxylate 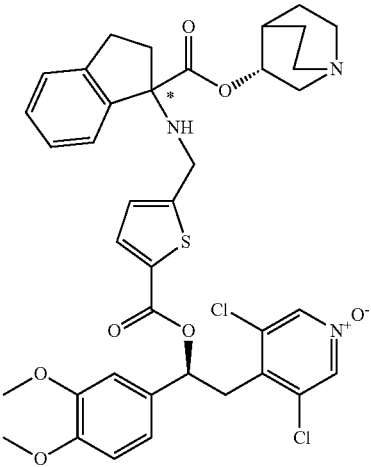 | Example 13 (Diastereoisomer 2) | $^1$H NMR (400 MHz, DMSO): δ 8.55 (s, 2 H), 7.65 (d, J = 3.8 Hz, 1 H), 7.40 (d, J = 6.8 Hz, 1 H), 7.30-7.18 (m, 3 H), 7.01-6.95 (m, 4 H), 6.12 (dd, J = 4.3, 9.6 Hz, 1 H), 4.70-4.66 (m, 1 H), 3.84 (d, J = 7.3 Hz, 2 H), 3.76 (s, 3 H), 3.73 (s, 3 H), 3.66 (dd, J = 7.6, 7.6 Hz, 1 H), 3.60-3.51 (m, 1 H), 3.31-3.21 (m, 1 H), 3.07-2.96 (m, 3 H), 2.67-2.56 (m, 4 H), 2.41 (d, J = 14.4 Hz, 1 H), 2.15-2.06 (m, 1 H), 1.80-1.78 (m, 1 H), 1.56-1.41 (m, 3 H), 1.26-1.15 (m, 1 H). LCMS (Method 1): [MH+] = 752 at 2.60 min. |
| [(1S)-2-(3,5-dichloro-1-oxido-pyridin-1-ium-4-yl)-1-(3,4-dimethoxyphenyl)ethyl] 5-[[[1-methyl-2-[(1-methyl-4-piperidyl)oxy]-2-oxo-1-phenyl-ethyl]amino]methyl]thiophene-2-carboxylate 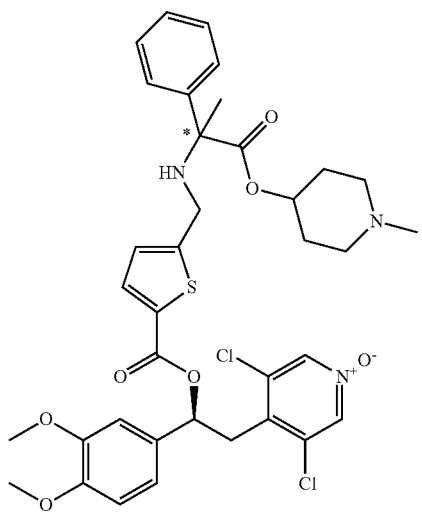 | Example 14 (Diastereoisomer 1) | $^1$H NMR (400 MHz, CDCl3) 8.15 (2H, s), 7.64 (1H, d, J = 3.8 Hz), 7.52-7.48 (2H, m), 7.36 (2H, dd, J = 7.7, 7.7 Hz), 7.32-7.28 (1H, m), 7.02-6.98 (2H, m), 6.91-6.84 (2H, m), 6.23 (1H, dd, J = 4.4, 9.5 Hz), 4.90-4.89 (1H, m), 3.92 (3H, s), 3.89 (3H, s), 3.86 (2H, s), 3.68 (1H, dd, J = 10.0, 13.8 Hz), 3.33 (1H, dd, J = 4.5, 13.9 Hz), 2.66-2.32 (3H, m), 2.23 (5H, s), 1.89-1.86 (2H, m), 1.75-1.70 (5H, m); LCMS (Method 1): [MH+] = 728 at 2.59 min. |

-continued

| Structure | Reference | Analytical Data |
|---|---|---|
| [(1S)-2-(3,5-dichloro-1-oxido-pyridin-1-ium-4-yl)-1-(3,4-dimethoxyphenyl)ethyl] 5-[[[1-methyl-2-[(1-methyl-4-piperidyl)oxy]-2-oxo-1-phenyl-ethyl]amino]methyl]thiophene-2-carboxylate | Example 15 (Diastereoisomer 2) | $^1$H NMR (400 MHz, CDCl3) 8.14 (2H, s), 7.64 (1H, d, J = 3.8 Hz), 7.52-7.48 (2H, m), 7.36 (2H, dd, J = 7.5, 7.5 Hz), 7.31-7.27 (1H, m), 6.99 (2H, d, J = 24.2 Hz), 6.90-6.84 (2H, m), 6.23 (1H, dd, J = 4.4, 9.7 Hz), 4.89 (1H, dd, J = 3.4, 7.2 Hz), 3.91 (3H, s), 3.88 (3H, s), 3.85 (2H, s), 3.67 (1H, dd, J = 9.9, 13.9 Hz), 3.32 (1H, dd, J = 4.7, 14.0 Hz), 2.62-2.60 (1H, m), 2.45-2.45 (2H, m), 2.23 (5H, s), 1.94-1.86 (2H, m), 1.72 (5H, s); LCMS (Method 1): [MH+] = 728 at 2.61 min. |
| [(1S)-2-(3,5-dichloro-1-oxido-pyridin-1-ium-4-yl)-1-(3,4-dimethoxyphenyl)ethyl] 5-[[[1-(2-dimethylaminoethyloxycarbonyl)indan-1-yl]amino]methyl]thiophene-2-carboxylate | Example 23 (Diastereoisomer 1) | $^1$H NMR (400 MHz, CDCl$_3$): δ 8.12 (s, 2 H), 7.62 (d, J = 1.8 Hz, 1 H), 7.30-7.24 (m, 4 H), 7.01-6.94 (m, 2 H), 6.88-6.86 (m, 2 H), 6.25-6.18 (m, 1 H), 4.28-4.22 (m, 2 H), 3.89-6.31 (m, 9 H), 3.68-3.60 (m, 1 H), 3.33-3.31 (m, 1 H), 3.11-3.09 (m, 2 H), 2.75-2.71 (m, 1 H), 2.57-2.55 (m, 2 H), 2.26-2.21 (m, 7 H). LCMS (Method 2): [MH+] = 714 at 3.32 min. |

-continued

| Structure | Reference | Analytical Data |
|---|---|---|
| [(1S)-2-(3,5-dichloro-1-oxido-pyridin-1-ium-4-yl)-1-(3,4-dimethoxyphenyl)ethyl] 5-[[[1-(2-dimethylaminoethyloxycarbonyl)indan-1-yl]amino]methyl]thiophene-2-carboxylate | Example 24 (Diastereoisomer 2) | $^1$H NMR (400 MHz, CDCl$_3$): δ 8.13 (s, 2 H), 7.61-7.60 (m, 1 H), 7.36-7.31 (m, 4 H), 6.98-6.93 (m, 2 H), 6.90-6.83 (m, 2 H), 6.21-6.20 (m, 1 H), 4.27-4.24 (m, 2 H), 3.89-3.81 (m, 9 H), 3.68-3.62 (m, 1 H), 3.32-3.29 (m, 1 H), 3.11-3.09 (m, 2 H), 2.75-2.71 (m, 1 H), 2.59-2.56 (m, 2 H), 2.24-2.20 (m, 7 H). LCMS (Method 2): [MH+] = 714 at 3.32 min. |
| [(1S)-2-(3,5-dichloro-1-oxido-pyridin-1-ium-4-yl)-1-(3,4-dimethoxyphenyl)ethyl] 5-[[[1-[(1-methyl-4-piperidyl)oxycarbonyl]indan-1-yl]amino]methyl]thiophene-2-carboxylate | Example 25 (Diastereoisomer 1) | $^1$H NMR (400 MHz, CDCl$_3$): δ 8.12 (s, 2 H), 7.62 (d, J = 3.8 Hz, 1 H), 7.29-7.26 (m, 3 H), 7.23-7.20 (m, 1 H), 7.00-6.95 (m, 2 H), 6.88 (d, J = 3.7 Hz, 1 H), 6.84 (d, J = 8.8 Hz, 1 H), 6.22 (dd, J = 4.7, 9.5 Hz, 1 H), 4.86-4.81 (m, 1 H), 3.90 (s, 3 H), 3.88-3.85 (m, 2 H), 3.87 (s, 3 H), 3.65 (dd, J = 9.7, 14.0 Hz, 1 H), 3.31 (dd, J = 4.8, 13.9 Hz, 1 H), 3.10 (t, J = 7.1 Hz, 2 H), 2.72 (dt, J = 6.1, 10.0 Hz, 1 H), 2.50-2.45 (m, 1 H), 2.35-2.28 (m, 1 H), 2.27-2.18 (m, 2 H), 2.22 (s, 3 H), 1.92-1.87 (m, 1 H), 1.83-1.62 (m, 4 H), NH not visible. LCMS (Method 1): [MH+] = 740 at 2.55 min. |

-continued

| Structure | Reference | Analytical Data |
|---|---|---|
| [(1S)-2-(3,5-dichloro-1-oxido-pyridin-1-ium-4-yl)-1-(3,4-dimethoxyphenyl)ethyl] 5-[[[1-[(1-methyl-4-piperidyl)oxycarbonyl]indan-1-yl]amino]methyl]thiophene-2-carboxylate<br />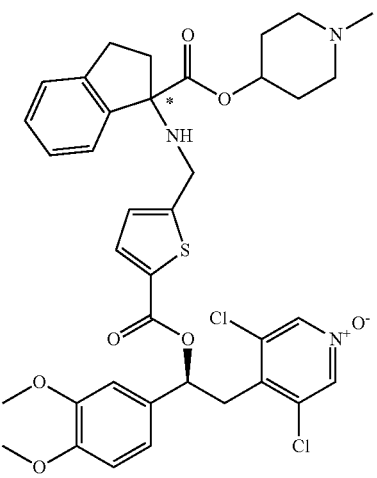 | Example 26 (Diastereoisomer 2) | $^1$H NMR (400 MHz, CDCl$_3$): δ 8.12 (s, 2 H), 7.62 (d, J = 3.8 Hz, 1 H), 7.29-7.26 (m, 3 H), 7.23-7.20 (m, 1 H), 7.00-6.95 (m, 2 H), 6.88 (d, J = 3.7 Hz, 1 H), 6.84 (d, J = 8.8 Hz, 1 H), 6.22 (dd, J = 4.7, 9.5 Hz, 1 H), 4.86-4.81 (m, 1 H), 3.90 (s, 3 H), 3.88-3.85 (m, 2 H), 3.87 (s, 3 H), 3.65 (dd, J = 9.7, 14.0 Hz, 1 H), 3.31 (dd, J = 4.8, 13.9 Hz, 1 H), 3.10 (t, J = 7.1 Hz, 2 H), 2.72 (dt, J = 6.1, 10.0 Hz, 1 H), 2.50-2.45 (m, 1 H), 2.35-2.28 (m, 1 H), 2.27-2.18 (m, 2 H), 2.22 (s, 3 H), 1.92-1.87 (m, 1 H), 1.83-1.62 (m, 4 H), NH not visible. LCMS (Method 1): [MH+] = 740 at 2.55 min. |
| [(1S)-2-(3,5-dichloro-1-oxido-pyridin-1-ium-4-yl)-1-(3,4-dimethoxyphenyl)ethyl] 5-[[[1-phenyl-1-[(3R)-quinuclidin-3-yl]oxycarbonyl-propyl]amino]methyl]thiophene-2-carboxylate<br />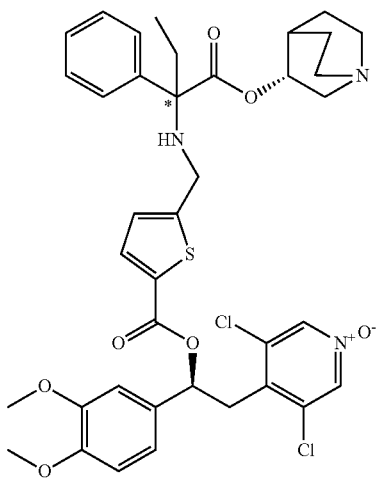 | Example 27 (Diastereoisomer 1) | $^1$H NMR (400 MHz, CD$_3$CN): δ 8.20 (s, 2 H), 7.68 (d, J = 3.8 Hz, 1 H), 7.57-7.54 (m, 2 H), 7.40 (dd, J = 7.6, 7.6 Hz, 2 H), 7.34-7.30 (m, 1 H), 7.08-7.02 (m, 2 H), 6.97-6.94 (m, 2 H), 6.18 (dd, J = 4.5, 9.6 Hz, 1 H), 4.82-4.78 (m, 1 H), 3.84 (s, 3 H), 3.82 (s, 3 H), 3.77-3.65 (m, 3 H), 3.35 (dd, J = 4.5, 14.1 Hz, 1 H), 3.14 (ddd, J = 2.1, 8.2, 14.7 Hz, 1 H), 2.88 (s, 1 H), 2.74-2.51 (m, 5 H), 2.38-2.28 (m, 1 H), 2.16-2.05 (m, 1 H), 1.87-1.83 (m, 1 H), 1.67-1.43 (m, 3 H), 1.31-1.23 (m, 1 H), 0.87 (t, J = 7.4 Hz, 3 H). LCMS (Method 1): [MH+] = 754 at 2.85 min. |

-continued

| Structure | Reference | Analytical Data |
|---|---|---|
| [(1S)-2-(3,5-dichloro-1-oxido-pyridin-1-ium-4-yl)-1-(3,4-dimethoxyphenyl)ethyl] 5-[[[1-phenyl-1-[(3R)-quinuclidin-3-yl]oxycarbonyl-propyl]amino]methyl]thiophene-2-carboxylate | Example 28 (Diastereoisomer 2) | $^1$H NMR (400 MHz, CD$_3$CN): δ 8.19 (s, 2 H), 7.69 (d, J = 4.6 Hz, 1 H), 7.59-7.53 (m, 2 H), 7.44-7.38 (m, 2 H), 7.36-7.29 (m, 1 H), 7.09-7.02 (m, 2 H), 6.99-6.92 (m, 2 H), 6.19 (dd, J = 4.5, 9.8 Hz, 1 H), 4.82-4.77 (m, 1 H), 3.85 (s, 3 H), 3.82 (s, 3 H), 3.77 (t, J = 8.2 Hz, 2 H), 3.73-3.63 (m, 1 H), 3.35 (dd, J = 4.7, 14.1 Hz, 1 H), 3.14-3.06 (m, 1 H), 2.90 (t, J = 8.0 Hz, 1 H), 2.66 (dt, J = 12.0, 20.7 Hz, 3 H), 2.59-2.47 (m, 1 H), 2.47-2.39 (m, 1 H), 2.35-2.24 (m, 1 H), 1.91-1.87 (m, 1 H), 1.70-1.46 (m, 3 H), 1.33-1.22 (m, 2 H), 0.85 (t, J = 7.3 Hz, 3 H). LCMS (Method 2): [MH+] = 754 at 3.55 min. |
| [(1S)-2-(3,5-dichloro-1-oxido-pyridin-1-ium-4-yl)-1-(3,4-dimethoxyphenyl)ethyl] 5-[[[1-(hydroxymethyl)-2-[(1-methyl-4-piperidyl)oxy]-2-oxo-1-phenyl-ethyl]amino]methyl]thiophene-2-carboxylate | Example 29 (Diastereoisomer 1) | $^1$H NMR (400 MHz, CD$_3$CN): δ 8.20 (s, 2 H), 7.67 (d, J = 3.8 Hz, 1 H), 7.52-7.48 (m, 2 H), 7.43-7.37 (m, 2 H), 7.36-7.32 (m, 1 H), 7.08-7.02 (m, 2 H), 6.97-6.91 (m, 2 H), 6.18 (dd, J = 4.5, 9.6 Hz, 1 H), 4.92-4.85 (m, 1 H), 4.17 (d, J = 10.9 Hz, 1 H), 4.00-3.90 (m, 2 H), 3.84 (s, 3H), 3.83 (s, 3H), 3.79-3.64 (m, 2 H), 3.35 (dd, J = 4.5, 14.1 Hz, 1 H), 3.11-3.11 (m, 2 H), 2.61-2.44 (m, 1 H), 2.32 (s, 1 H), 2.23 (d, J = 10.9 Hz, 2 H), 2.14 (s, 3 H), 1.90-1.79 (m, 2 H), 1.72-1.58 (m, 2 H). LCMS (Method 2): [MH+] = 744 at 3.13 min. |

-continued

| Structure | Reference | Analytical Data |
|---|---|---|
| [(1S)-2-(3,5-dichloro-1-oxido-pyridin-1-ium-4-yl)-1-(3,4-dimethoxyphenyl)ethyl] 5-[[[1-(hydroxymethyl)-2-[(1-methyl-4-piperidyl)oxy]-2-oxo-1-phenyl-ethyl]amino]methyl]thiophene-2-carboxylate 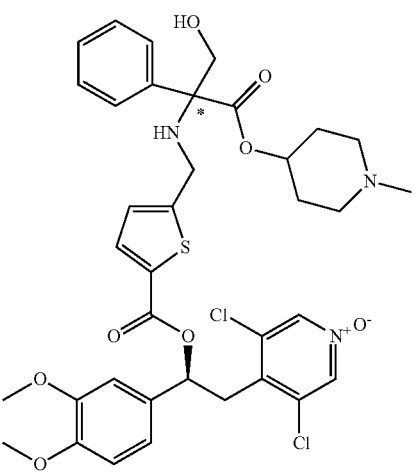 | Example 30 (Diastereoisomer 2) | $^1$H NMR (400 MHz, CD$_3$CN): δ 8.20 (s, 2 H), 7.68 (d, J = 4.7 Hz, 1 H), 7.52-7.48 (m, 2 H), 7.43-7.38 (m, 2 H), 7.37-7.33 (m, 1 H), 7.08-7.02 (m, 2 H), 6.97-6.93 (m, 2 H), 6.19 (dd, J = 5.7, 9.3 Hz, 1 H), 4.92-4.85 (m, 1 H), 4.21-4.14 (m, 1 H), 3.97-3.93 (m, 2 H), 3.84 (s, 3H), 3.83 (s, 3 H), 3.80-3.73 (m, 1 H), 3.72-3.65 (m, 1 H), 3.36 (dd, J = 5.2, 14.5 Hz, 1 H), 3.24-3.03 (m, 2 H), 2.73 (d, J = 145.3 Hz, 1 H), 2.51-2.40 (m, 1 H), 2.35 (d, J = 42.4 Hz, 1 H), 2.18-2.05 (m, 4 H), 1.90-1.79 (m, 2 H), 1.70-1.58 (m, 2 H). LCMS (Method 2): [MH+] = 744 at 3.12 min. |
| [(1S)-2-(3,5-dichloro-1-oxido-pyridin-1-ium-4-yl)-1-(3,4-dimethoxyphenyl)ethyl] 5-[[[1-(hydroxymethyl)-2-oxo-1-phenyl-2-[(3R)-quinuclidin-3-yl]oxy-ethyl]amino]methyl]thiophene-2-carboxylate 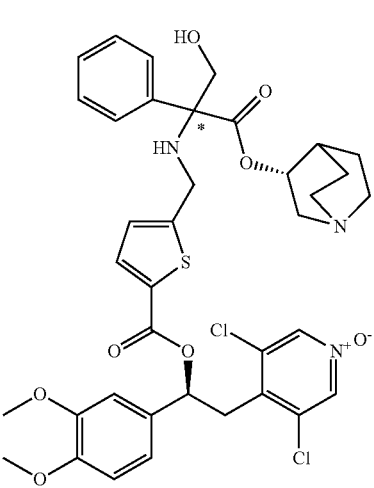 | Example 31 (Diastereoisomer 1) | $^1$H NMR (400 MHz, CD$_3$CN): δ 8.21 (s, 2 H), 7.68 (d, J = 3.8 Hz, 1 H), 7.55-7.51 (m, 2 H), 7.45-7.40 (m, 2 H), 7.39-7.33 (m, 1 H), 7.09-7.03 (m, 2 H), 6.98-6.94 (m, 2 H), 6.18 (dd, J = 4.4, 9.7 Hz, 1 H), 4.86-4.82 (m, 1 H), 4.23 (d, J = 10.9 Hz, 1 H), 3.99-3.77 (m, 3 H), 3.85 (s, 3 H), 3.83 (s, 3 H), 3.69 (dd, J = 9.6, 14.1 Hz, 1 H), 3.36 (dd, J = 4.5, 14.1 Hz, 1 H), 3.19-3.08 (m, 2 H), 2.75-2.44 (m, 5 H), 2.01-1.89 (m, 1 H), 1.70-1.62 (m, 2 H), 1.58-1.49 (m, 1 H), 1.37-1.27 (m, 1 H). NH not seen. LCMS (Method 3): [MH+] = 756 at 2.74 min. |

-continued

| Structure | Reference | Analytical Data |
|---|---|---|
| [(1S)-2-(3,5-dichloro-1-oxido-pyridin-1-ium-4-yl)-1-(3,4-dimethoxyphenyl)ethyl] 5-[[[1-(hydroxymethyl)-2-oxo-1-phenyl-2-[(3R)-quinuclidin-3-yl]oxy-ethyl]amino]methyl]thiophene-2-carboxylate | Example 32 (Diastereoisomer 2) | $^1$H NMR (400 MHz, CD$_3$CN): δ 8.20 (s, 2 H), 7.68 (d, J = 3.8 Hz, 1 H), 7.54-7.51 (m, 2 H), 7.43-7.39 (m, 2 H), 7.37-7.32 (m, 1 H), 7.08-7.03 (m, 2 H), 6.98-6.92 (m, 2 H), 6.18 (dd, J = 4.5, 9.9 Hz, 1 H), 4.88-4.83 (m, 1 H), 4.25 (d, J = 10.9 Hz, 1 H), 3.99-3.91 (m, 2 H), 3.85 (s, 3 H), 3.83 (s, 3 H), 3.79-3.73 (m, 1 H), 3.69 (dd, J = 9.7, 13.9 Hz, 1 H), 3.35 (dd, J = 4.5, 14.1 Hz, 1 H), 3.20-3.12 (m, 2 H), 2.75-2.61 (m, 5 H), 1.93-1.85 (m, 1 H), 1.68-1.45 (m, 3 H), 1.31-1.23 (m, 1 H). NH not seen. LCMS (Method 3): [MH+] = 756 at 2.74 min. |
| [(1S)-2-(3,5-dichloro-1-oxido-pyridin-1-ium-4-yl)-1-(3,4-dimethoxyphenyl)ethyl] 5-[[[1-(hydroxymethyl)-2-oxo-1-phenyl-2-[(3R)-quinuclidin-3-yl]oxy-ethyl]-methyl-amino]methyl]thiophene-2-carboxylate | Example 33 (Diastereoisomer 1) | $^1$H NMR (400 MHz, CD$_3$CN): δ 8.21 (s, 2 H), 7.68 (d, J = 3.8 Hz, 1 H), 7.62-7.58 (m, 2 H), 7.44-7.39 (m, 2 H), 7.37-7.33 (m, 1 H), 7.10-7.04 (m, 2 H), 6.98-6.95 (m, 2 H), 6.19 (dd, J = 4.4, 9.7 Hz, 1 H), 4.96-4.92 (m, 1 H), 4.27-4.17 (m, 2 H), 4.07-3.93 (m, 2 H), 3.86 (s, 3 H), 3.83 (s, 3 H), 3.70 (dd, J = 9.9, 14.1 Hz, 1 H), 3.36 (dd, J = 4.5, 14.1 Hz, 1 H), 3.22 (dd, J = 8.2, 14.8 Hz, 1 H), 2.99 (br s, 1 H), 2.77-2.60 (m, 5 H), 2.37 (s, 3 H), 2.03-1.99 (m, 1 H), 1.81-1.53 (m, 3 H), 1.42-1.33 (m, 1 H). LCMS (Method 3): [MH+] = 770 at 2.81 min. |

| Structure | Reference | Analytical Data |
|---|---|---|
| [(1S)-2-(3,5-dichloro-1-oxido-pyridin-1-ium-4-yl)-1-(3,4-dimethoxyphenyl)ethyl] 5-[[[1-(hydroxymethyl)-2-oxo-1-phenyl-2-[(3R)-quinuclidin-3-yl]oxy-ethyl]-methyl-amino]methyl]thiophene-2-carboxylate | Example 34 (Diastereoisomer 2) | $^1$H NMR (400 MHz, CD$_3$CN): δ 8.21 (s, 2 H), 7.69 (d, J = 3.8 Hz, 1 H), 7.63-7.59 (m, 2 H), 7.44-7.40 (m, 2 H), 7.37-7.33 (m, 1 H), 7.10-7.04 (m, 2 H), 6.99-6.95 (m, 2 H), 6.19 (dd, J = 4.5, 9.6 Hz, 1 H), 4.98-4.93 (m, 1 H), 4.26 (d, J = 12.2 Hz, 1 H), 4.18 (d, J = 11.6 Hz, 1 H), 4.08-3.97 (m, 2 H), 3.86 (s, 3 H), 3.83 (s, 3 H), 3.70 (dd, J = 9.9, 14.1 Hz, 1 H), 3.37 (dd, J = 4.5, 14.1 Hz, 1 H), 3.24-3.16 (m, 1 H), 3.05 (br s, 1 H), 2.79-2.61 (m, 5 H), 1.99-1.91 (m, 1 H), 2.38 (s, 3 H), 1.75-1.53 (m, 3 H), 1.40-1.30 (m, 1 H). LCMS (Method 3): [MH+] = 770 at 2.81 min. |
| [(1S)-2-(3,5-dichloro-1-oxido-pyridin-1-ium-4-yl)-1-(3,4-dimethoxyphenyl)ethyl] 5-[[[1-(methoxymethyl)-2-oxo-1-phenyl-2-[(3R)-quinuclidin-3-yl]oxy-ethyl]amino]methyl]thiophene-2-carboxylate | Example 35 (Diastereoisomer 2) | $^1$H NMR (400 MHz, DMSO): δ 8.57 (s, 2 H), 7.66 (d, J = 3.8 Hz, 1 H), 7.53-7.49 (m, 2 H), 7.43-7.37 (m, 2 H), 7.33 (dd, J = 7.1, 7.1 Hz, 1 H), 7.04 (s, 1 H), 7.01 (s, 2 H), 6.97 (d, J = 3.8 Hz, 1 H), 6.16 (dd, J = 4.3, 9.6 Hz, 1 H), 4.84-4.80 (m, 1 H), 4.01-3.84 (m, 3 H), 3.80 (s, 3H), 3.77 (s, 3 H), 3.76-3.57 (m, 3 H), 3.35-3.33 (m, 4 H), 3.20-3.13 (m, 1 H), 2.76-2.63 (m, 4 H), 1.94-1.86 (m, 1 H), 1.65-1.57 (m, 1 H), 1.53-1.48 (m, 2 H), 1.31-1.23 (m, 2 H). LCMS [(Method 72)]: [MH+] = 770 at 3.52 min. |

Example 16. [(1S)-2-(3,5-dichloro-1-oxido-pyridin-1-ium-4-yl)-1-(3,4-dimethoxyphenyl)ethyl] 5-[[[1-methyl-2-[(3R)-1-oxidoquinuclidin-1-ium-3-yl]oxy-2-oxo-1-phenyl-ethyl]amino]methyl]thiophene-2-carboxylate

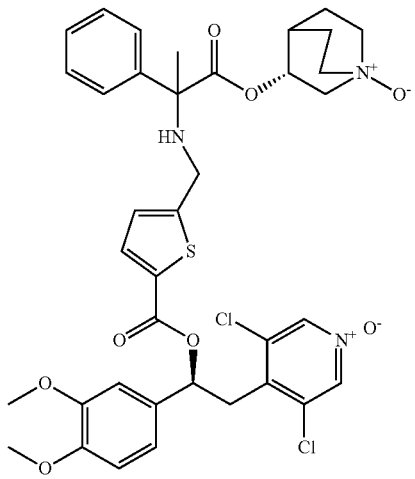

The title compound was obtained as a side product during the purification by SFC of Example 7 and Example 8.

$^1$H NMR (400 MHz, CD$_3$CN): δ 8.20 (s, 2H), 7.68 (d, J=3.8 Hz, 1H), 7.58-7.53 (m, 2H), 7.44-7.39 (m, 2H), 7.37-7.30 (m, 1H), 7.07 (d, J=2.1 Hz, 1H), 7.03 (dd, J=8.4, 2.2 Hz, 1H), 6.97-6.92 (m, 2H), 6.18 (dd, J=9.6, 4.5 Hz, 1H), 5.15-5.09 (m, 1H), 3.88 (d, J=7.5 Hz, 2H), 3.83 (s, 3H), 3.82 (s, 3H), 3.67 (dd, J=14.3, 10 Hz, 1H), 3.69-3.61 (m, 1H), 3.34 (dd, J=14.1, 4.6 Hz, 1H), 3.26-2.92 (m, 6H), 2.14-2.09 (m, 1H), 2.04-1.98 (m, 1H), 1.89-1.84 (m, 1H), 1.83-1.80 (m, 1H), 1.80-1.75 (m, 1H), 1.73 (s, 3H). LCMS (Method 2): [MH+]=756 at 2.80 min.

Pharmacological Activity of the Compounds of the Invention

In Vitro Determination of PDE4 Inhibitory Activity

In vitro determination of PDE4 inhibitory activity for compounds of the invention may be determined according to one of the protocols reported below.

PDE4B2 HTRF Assay:

PDE4B2 activity is detected using the LANCE Ultra cAMP homogeneous time resolved fluorescence resonance energy transfer (TR-FRET) assay from Perkin Elmer.

The assay is based on the competition between the europium (Eu) chelate-labeled cAMP tracer and sample cAMP for binding sites on cAMP-specific monoclonal antibodies (mAb) labelled with the ULight™ dye. The assay is carried out in 384-well low volume plates in a volume of 10 μl. Human recombinant PDE4B2 (80 pM) is incubated for 2 h with 3 nM cAMP in buffer containing 1×HBSS, 5 mM HEPES, 3 mM MgCl$_2$, 0.1% BSA, pH 7.4 with or without test compounds. The enzymatic reactions are efficiently stopped by the addition of 500 μM IBMX present in the combined Stop/Detection buffer containing europium (Eu) chelate-labeled cAMP tracer and cAMP-specific monoclonal antibodies (mAb) labelled with the ULight™ dye. Samples are then further incubated for 1 h before plates are read at ex 340 nm and em at 665 nm and 615 nm on an EnVision reader. IC$_{50}$ values are determined from competition curves using a non-linear curve fitting program.

PDE4 Cell Free Assay Protocol:

PDE4 activity is determined in U937 human monocytic supernatants cells lysate. Cells are cultured, harvested and supernatant fraction prepared essentially as described in Torphy T J et al J. Pharmacol. Exp. Ther. 1992; 263:1195-1205, which is incorporated herein by reference in its entirety. U937 cells are grown at 37° C., 5% CO$_2$ in RPMI 1640 with GlutaMAX™-I medium supplemented with 10% fetal bovine serum and 100 μg/mL Pen-strep (Gibco). Cells are harvested and washed twice by centrifugation (150×g, 8 min) in cold PBS. Washed cells are re-suspended in cold Krebs-Ringer-Henseleit buffer at a final concentration 20×10$^6$ cells/mL and sonicated. After centrifugation at 15000×g for 20 min, the supernatants are pooled, divided in aliquots and stored at −80° C.

PDE4 activity is determined in cells supernatants by assaying cAMP disappearance from the incubation mixtures. The concentration of the test compounds ranges between 10$^{-12}$ M and 10$^{-6}$ M. Reactions are stopped by enzyme heat inactivation (2.5 minutes at 100° C.) and residual cAMP content is determined using the 'LANCE cAMP Assay' from PerkinElmer following the provider instructions.

The results, expressed as mean±standard deviation of the molar concentration of the test compound producing 50% inhibition of cAMP disappearance (IC$_{50}$). Percentage of inhibition of PDE4 activity is calculated, assuming cAMP disappearance in the absence of inhibitors as 100% and cAMP disappearance in heat inactivated samples as 0%.

Representative compounds of the invention, when tested in one of the above reported protocols, displayed an IC$_{50}$ lower than 100 nM.

In Vitro Determination of M3 Antagonism

In vitro determination of M3 antagonism for compounds of the invention may be determined according to one of the protocols reported below.

M3 Receptor Radioligand Binding Assay:

Human M$_3$ receptor membranes (15 μg/well) from Perkin Elmer are incubated with 0.52 nM Scopolamine Methyl Chloride, [N-methyl-3H] with or without test compounds, or a saturating concentration of Atropine (5 μM) for the determination of non-specific binding. The assay is carried out in 96-well polypropylene plates in a volume of 250 μl. The assay buffer used is 50 mM Tris-HCl, 154 mM NaCl (pH 7.4). The final assay concentration of DMSO is 0.5% (v/v). The plates are sealed and incubated for 2 h at room temperature on an orbital shaker (slow speed). Membranes are harvested onto 96-well unifilter GF/C filter plates pre-treated with 0.5% polyethyleneimine (v/v), using a filter manifold, washed four times with 200 μl of assay buffer. The plates are dried before addition of 50 μl of microscint-0, sealed then read in a Trilux Microbeta scintillation counter. IC$_{50}$ values are determined from competition curves using a non-linear curve fitting program. K$_i$ values are calculated from IC$_{50}$ values by the Cheng and Prusoff equation.

M3 Binding Assay:

CHO-K1 clone cells expressing the human M3-receptor (Swissprot P20309) were harvested in Ca$^{++}$/Mg$^{++}$ free phosphate-buffered saline and collected by centrifugation at 1500 rpm for 3 min. The pellets were resuspended in ice cold buffer A (15 mM Tris-HCl pH 7.4, 2 mM MgCl$_2$, 0.3 mM EDTA, 1 mM EGTA) and homogenized by a PBI politron (setting 5 for 15 s). The crude membrane fraction was collected by two consecutive centrifugation steps at 40000 g for 20 min at 4° C., separated by a washing step in buffer A. The pellets obtained were finally resuspended in buffer B (75 mM Tris HCl pH 7.4, 12.5 mM $MgCl_2$, 0.3 mM EDTA, 1 mM EGTA, 250 mM sucrose), and aliquots were stored at −80° C.

The day of experiment, frozen membranes were resuspended in buffer C (50 mM Tris-HCl pH 7.4, 2.5 mM $MgCl_2$, 1 mM EDTA). The non-selective muscarinic radioligand [$^3$H]—N-methyl scopolamine (*Mol. Pharmacol.* 45:899-907, which is incorporated herein by reference in its entirety) was used to label the M3 binding sites. Binding experiments were performed in duplicate (ten point concentrations curves) in 96 well plates at radioligand concentration of 0.1-0.3 nM. The non-specific binding was determined in the presence of cold N-methyl scopolamine 10 μM. Samples (final volume 0.75 mL) were incubated at room temperature for 90 min. The reaction was terminated by rapid filtration through GF/B Unifilter plates and two washes (0.75 mL) with cold buffer C using a Packard Filtermate Harvester. Radioactivity on the filters was measured by a microplate scintillation counter TriCarb 2500 (PerkinElmer).

Representative compounds of the invention, when tested in one of the above reported protocols, displayed an $IC_{50}$ lower than 100 nM.

Representative compounds of the invention displayed an $IC_{50}$ lower than 100 nM in both PDE4 cell free and M3 binding assays.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound of formula (I):

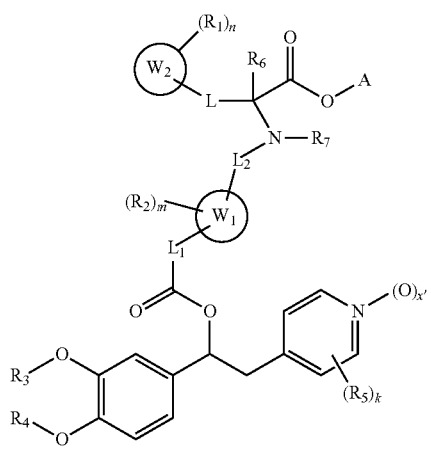

wherein
each $R_1$ is the same or different and is independently hydrogen, halogen, $(C_1-C_4)$ alkyl, $(C_1-C_4)$ alkoxy, $(C_1-C_4)$ haloalkyl, hydroxy, $—SO_2NR^IR^{II}$, $—CN$, $—NR^ISO_2R^{III}$, $—NR^IR^{II}$, $—(CO)NR^IR^I$, or $—NR^I(CO)R^{III}$, and wherein each said $(C_1-C_4)$ alkyl is optionally substituted by one or more groups selected from the group consisting of $(C_3-C_7)$ cycloalkyl, hydroxyl, and $—NR^IR^{II}$ and wherein each said $(C_1-C_4)$ alkoxy is optionally substituted by one or more halogen atoms or $(C_3-C_7)$ cycloalkyl groups, wherein:

$R^I$ is hydrogen or $(C_1-C_6)$ alkyl;
$R^{II}$ is hydrogen or $(C_1-C_6)$ alkyl;
$R^{III}$ is hydrogen or $(C_1-C_6)$ alkyl;
n is an integer ranging from 1 to 3;
each $R_2$ is the same or different and is independently hydrogen, halogen, $(C_1-C_4)$ alkyl, $(C_1-C_4)$ alkoxy, $(C_1-C_4)$ haloalkyl, hydroxy, $—SO_2NR^IR^{II}$, $—CN$, $—NR^ISO_2R^{III}$, $—NR^IR^{II}$, $—(CO)NR^IR^{II}$, or $—NR^I(CO)R^{III}$ and wherein eachsaid $(C_1-C_4)$ alkyl is optionally substituted by one or more groups selected from the group consisting of $(C_3-C_7)$ cycloalkyl, hydroxyl, and $—NR^IR^{II}$ and wherein each said $(C_1-C_4)$ alkoxy is optionally substituted by one or more halogen atoms or $(C_3-C_7)$ cycloalkyl groups, wherein:

$R^I$, $R^{II}$, and $R^{III}$ are as defined above;
m is an integer ranging from 1 to 3;
each $R_3$ and each $R_4$ are the same or different and is independently H, $(C_3-C_7)$ cycloalkylcarbonyl, $(C_1-C_6)$ alkyl optionally substituted by one or more substituents selected from the group consisting of $(C_3-C_7)$ cycloalkyl and $(C_5-C_7)$ cycloalkenyl, $(C_1-C_6)$ haloalkyl, $(C_3-C_7)$ cycloalkyl, $(C_5-C_7)$ cycloalkenyl, $(C_2-C_6)$ alkenyl, and $(C_2-C_6)$ alkynyl;

or $R_3$ and $R_4$, together with the interconnecting atoms, form a 2,2-difluoro-1,3-dioxolane ring of formula (r) fused to the phenyl moiety which bears groups $—OR_3$ and $—OR_4$, wherein asterisks indicate carbon atoms shared with such phenyl ring:

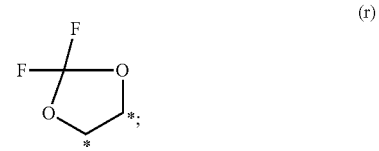

each $R_5$ is the same or different and is independently CN, $NO_2$, $CF_3$, or halogen;
k is 0 or an integer ranging from 1 to 3;
x' is 0 or 1;
$L_1$ is a bond or $—(CH_2)_p—$ wherein p is an integer ranging from 1 to 4;
$W_1$ is a divalent arylene, heteroarylene, or saturated monocyclic heterocycloalkylene group;
$L_2$ is a bond, $—(CH_2)_q—$ wherein q is 1 or 2, [1]-(CO)—[X]—$(CH_2)_t$-[2], or [1]-$(SO_2)$—[X]—$(CH_2)_t$-[2], wherein [1] and [2] represent, respectively the point of attachment of group $L_2$ to the ring $W_1$ and to the chain nitrogen atom, and wherein
[X] is a bond or a substituted or unsubstituted arylene group;
t is an integer ranging from 1 to 4;
$R_7$ is hydrogen or $(C_1-C_4)$ alkyl optionally substituted by hydroxy or $—NR_{11}R_{12}$, wherein $R_{11}$ and $R_{12}$ are independently hydrogen or $(C_1-C_4)$ alkyl, or, together with the nitrogen atom to which they are linked, $R_{11}$ and $R_{12}$ form a saturated heterocycloalkyl group having an additional heteroatom selected from the group consisting of O, S, and NH; and A is a nitrogen containing group which is:
- a group (a) which is —$(CH_2)_s$—$NR_8R_9$ wherein s is an integer ranging from 1 to 4 and $R_8$ and $R_9$ are independently hydrogen or ($C_1$-$C_4$) alkyl; or
- a group (b) which is a saturated monocyclic, bicyclic or tricyclic heterocyclic ring system optionally substituted by one or two groups $R_{10}$ which are at each occurrence independently ($C_1$-$C_4$) alkyl or benzyl; and wherein $W_2$ is a phenyl ring, L is a bond, and one of $R_1$, which is in the ortho position with respect to L, and $R_6$ are connected to form a ring radical, represented by formula (IB):

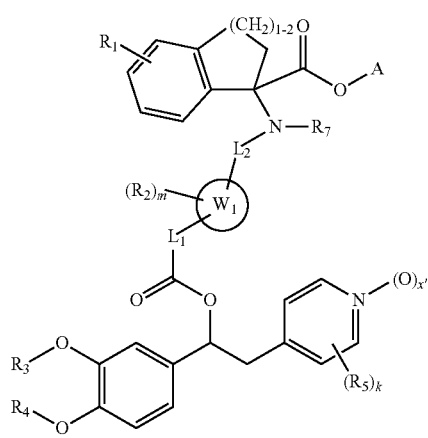

(IB)

or a pharmaceutically acceptable salt thereof.

2. A compound, or pharmaceutically acceptable salt according to claim 1, wherein A is a group of formula (i), (ii), (iii), or (iv):

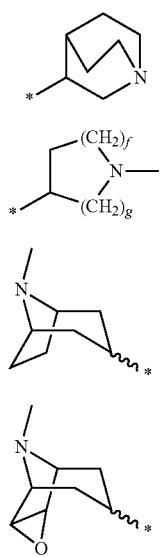

wherein
f=1, 2 or 3;
g=1, 2 or 3;
and the asterisk (*) represents the point of attachment to the oxygen atom of formula (I).

3. A compound, or pharmaceutically acceptable salt according to claim 1, wherein x' is 1.

4. A compound or pharmaceutically acceptable salt according to claim 1, wherein $L_1$ is a bond, $W_1$ is thiophene-2,5-diyl, thiophene-2,4-diyl, phenylene-1,4-diyl, phenylene-1,3-diyl, or phenylene-1,2-diyl, $L_2$ is —$(CH_2)$—, and $R_7$ is H.

5. A compound, or pharmaceutically acceptable salt according to claim 1, wherein $R_7$ is H or methyl.

6. A compound, or pharmaceutically acceptable salt according to claim 1, wherein $L_1$ is a bond and $W_1$ is a divalent saturated monocyclic heterocycloalkylene group.

7. A compound or pharmaceutically acceptable salt according claim 1, represented by formula (I)' which has the absolute configuration of carbon (1) which is shown below:

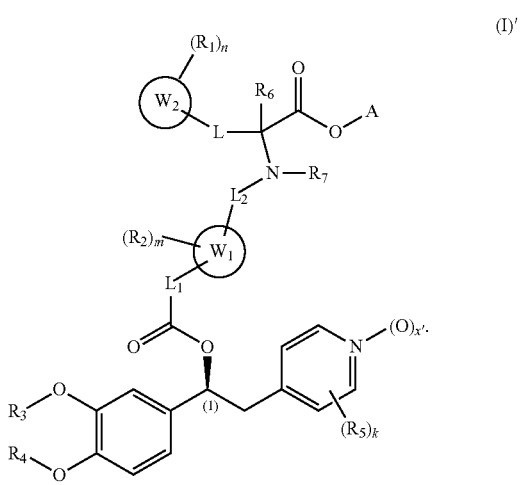

(I)'

8. A compound, which is selected from the group consisting of:
- [(3R)-quinuclidin-3-yl]-1-[[4-[(1S)-2-(3,5-dichloro-1-oxido-pyridin-1-ium-4-yl)-1-(3,4-dimethoxyphenyl)ethoxy]carbonylphenyl]methylamino]indane-1-carboxylate;
- [(1S)-2-(3,5-dichloro-1-oxido-pyridin-1-ium-4-yl)-1-(3,4-dimethoxyphenyl)-ethyl]-5-[[[1-[(3R)-quinuclidin-3-yl]oxycarbonylindan-1-yl]amino]methyl]thiophene-2-carboxylate;
- [(1S)-2-(3,5-dichloro-1-oxido-pyridin-1-ium-4-yl)-1-(3,4-dimethoxyphenyl)-ethyl]-5-[[[1-(2-dimethylaminoethyloxycarbonyl)indan-1-yl]amino]methyl]thiophene-2-carboxylate;
- [(1S)-2-(3,5-dichloro-1-oxido-pyridin-1-ium-4-yl)-1-(3,4-dimethoxyphenyl)-ethyl]-5-[[[1-[(1-methyl-4-piperidyl)oxycarbonyl]indan-1-yl]amino]methyl]thiophene-2-carboxylate;

or a pharmaceutically acceptable salt of said compound.

9. A pharmaceutical composition, comprising a compound or pharmaceutically acceptable salt according to claim 1 in admixture with one or more pharmaceutically acceptable carriers.

10. A pharmaceutical composition according to claim 9, further comprising another active ingredient.

11. A method for the treatment of a disease selected from the group consisting of asthma and COPD, said method comprising administering to a subject in need thereof an effective amount of a compound or pharmaceutically acceptable salt according to claim 1.

12. A method according to claim 11, wherein said disease is asthma.

13. A method according to claim 11, wherein said disease is COPD.

14. An inhalation device, which contains a pharmaceutical composition according to claim 9.

15. An inhalation device, which contains a pharmaceutical composition according to claim 10.

16. A kit, comprising a pharmaceutical composition according to claim 9 and a device which is a single- or multi-dose dry powder inhaler, a metered dose inhaler or a nebulizer.

17. A kit, comprising a pharmaceutical composition according to claim 10 and a device which is a single- or multi-dose dry powder inhaler, a metered dose inhaler or a nebulizer.

* * * * *